US012672803B2

(12) United States Patent
Oja et al.

(10) Patent No.: US 12,672,803 B2
(45) Date of Patent: Jul. 7, 2026

(54) ANALYTE SENSORS EMPLOYING MULTIPLE ENZYMES AND METHODS ASSOCIATED THEREWITH

(71) Applicant: Abbott Diabetes Care Inc., Alameda, CA (US)

(72) Inventors: Stephen Oja, Reno, NV (US); Tianmei Ouyang, Saratoga, CA (US); Hyun Cho, Berkeley, CA (US); Lam N. Tran, Danville, CA (US); Benjamin J. Feldman, Berkeley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 19/340,421

(22) Filed: Sep. 25, 2025

(65) Prior Publication Data

US 2026/0020797 A1 Jan. 22, 2026

Related U.S. Application Data

(63) Continuation of application No. 18/910,782, filed on Oct. 9, 2024, which is a continuation of application
(Continued)

(51) Int. Cl.
*A61B 5/1486* (2006.01)
*A61B 5/145* (2006.01)
(Continued)

(52) U.S. Cl.
CPC ...... *A61B 5/14865* (2013.01); *A61B 5/14532* (2013.01); *C12Q 1/002* (2013.01);
(Continued)

(58) Field of Classification Search
None
See application file for complete search history.

(56) References Cited

U.S. PATENT DOCUMENTS 4,321,123 A 3/1982 Nakamura et al.
4,721,677 A 1/1988 Clark, Jr.
(Continued)

FOREIGN PATENT DOCUMENTS

CN 1735375 A 2/2006
CN 101849180 B 8/2017
(Continued)

OTHER PUBLICATIONS

Alva, S., et al., "Feasibility of Continuous Ketone Monitoring in Subcutaneous Tissue Using a Ketone Sensor," Journal of Diabetes Science and Technology 15(4):768-774, Sage, United States (Jul. 2021).
(Continued)

*Primary Examiner* — J. Christopher Ball
(74) *Attorney, Agent, or Firm* — Sterne, Kessler, Goldstein & Fox P.L.L.C.

(57) ABSTRACT

Methods and analyte sensors including at least a first working electrode having a first active area thereon, and performing a dip coating operation to deposit a bilayer membrane upon the first working electrode and the first active area. The bilayer may include an inner layer having a first membrane polymer and an outer layer having a second membrane polymer, the first membrane polymer and the second membrane polymer differing from one another. The dip coating operation may comprise one or more first dips in a first membrane formulation to form the inner layer of the bilayer membrane and one or more second dips in a second membrane formulation to form the outer layer of the bilayer membrane upon the inner layer.

27 Claims, 24 Drawing Sheets

Related U.S. Application Data

No. 17/819,099, filed on Aug. 11, 2022, now Pat. No. 12,150,761, which is a continuation of application No. 17/151,274, filed on Jan. 18, 2021, now Pat. No. 12,004,858, which is a continuation of application No. 16/774,841, filed on Jan. 28, 2020, now Pat. No. 12,048,539.

(60) Provisional application No. 62/797,566, filed on Jan. 28, 2019.

(51) Int. Cl.
*C12Q 1/00* (2006.01)
*G01N 27/327* (2006.01)

(52) U.S. Cl.
CPC ......... *G01N 27/3271* (2013.01); *C12Q 1/005* (2013.01); *G01N 2333/9029* (2013.01); *G01N 2333/904* (2013.01); *G01N 2333/908* (2013.01)

(56) References Cited

U.S. PATENT DOCUMENTS

| | | | |
|---|---|---|---|
| 5,262,035 | A | 11/1993 | Gregg et al. |
| 5,264,105 | A | 11/1993 | Gregg et al. |
| 5,322,063 | A | 6/1994 | Allen et al. |
| 5,356,786 | A | 10/1994 | Heller et al. |
| 5,593,852 | A | 1/1997 | Heller et al. |
| 5,696,314 | A | 12/1997 | McCaffrey et al. |
| 5,783,056 | A | 7/1998 | Hampp et al. |
| 5,792,621 | A | 8/1998 | Verostko et al. |
| 5,793,621 | A | 8/1998 | Yamada |
| 5,820,551 | A | 10/1998 | Hill et al. |
| 5,965,105 | A | 10/1999 | Rayalu et al. |
| 5,965,106 | A | 10/1999 | Pomato et al. |
| 6,071,391 | A | 6/2000 | Gotoh et al. |
| 6,121,009 | A | 9/2000 | Heller et al. |
| 6,134,461 | A | 10/2000 | Say et al. |
| 6,175,752 | B1 | 1/2001 | Say et al. |
| 6,241,863 | B1 | 6/2001 | Monbouquette |
| 6,284,478 | B1 | 9/2001 | Heller et al. |
| 6,377,894 | B1 | 4/2002 | Deweese et al. |
| 6,503,381 | B1 | 1/2003 | Gotoh et al. |
| 6,514,460 | B1 | 2/2003 | Fendrock |
| 6,514,718 | B2 | 2/2003 | Heller et al. |
| 6,541,216 | B1 | 4/2003 | Wilsey et al. |
| 6,560,471 | B1 | 5/2003 | Heller et al. |
| 6,579,690 | B1 | 6/2003 | Bonnecaze et al. |
| 6,600,997 | B2 | 7/2003 | Deweese et al. |
| 6,605,200 | B1 | 8/2003 | Mao et al. |
| 6,605,201 | B1 | 8/2003 | Mao et al. |
| 6,654,625 | B1 | 11/2003 | Say et al. |
| 6,676,816 | B2 | 1/2004 | Mao et al. |
| 6,736,957 | B1 | 5/2004 | Forrow et al. |
| 6,746,582 | B2 | 6/2004 | Heller et al. |
| 6,881,551 | B2 | 4/2005 | Heller et al. |
| 6,932,894 | B2 | 8/2005 | Mao et al. |
| 6,946,299 | B2 | 9/2005 | Neel et al. |
| 7,090,756 | B2 | 8/2006 | Mao et al. |
| 7,299,082 | B2 | 11/2007 | Feldman et al. |
| 7,501,053 | B2 | 3/2009 | Karinka et al. |
| 7,520,970 | B2 | 4/2009 | Sato et al. |
| 7,563,588 | B2 | 7/2009 | Gao et al. |
| 7,754,093 | B2 | 7/2010 | Forrow et al. |
| 7,811,231 | B2 | 10/2010 | Jin et al. |
| 7,822,557 | B2 | 10/2010 | Chen et al. |
| 8,106,780 | B2 | 1/2012 | Goodnow |
| 8,268,143 | B2 | 9/2012 | Liu et al. |
| 8,435,682 | B2 | 5/2013 | Heller |
| 8,444,834 | B2 | 5/2013 | Liu et al. |
| 8,545,693 | B2 | 10/2013 | McColl et al. |
| 8,761,857 | B2 | 6/2014 | Feldman et al. |
| 8,911,908 | B2 | 12/2014 | Sakai et al. |
| 9,290,839 | B2 | 3/2016 | Wang et al. |
| 9,775,549 | B2 | 10/2017 | Ouyang et al. |
| 9,914,952 | B2 | 3/2018 | Ouyang et al. |
| 9,927,386 | B2 | 3/2018 | Wang et al. |
| 9,983,161 | B2 | 5/2018 | Feldman et al. |
| 10,022,076 | B2 | 7/2018 | Hoss et al. |
| 10,136,816 | B2 | 11/2018 | Bernstein et al. |
| 10,201,301 | B2 | 2/2019 | Heller et al. |
| 10,702,193 | B2 | 7/2020 | Simpson et al. |
| 11,091,788 | B2 | 8/2021 | Ouyang et al. |
| 2001/0003045 | A1 | 6/2001 | Davis et al. |
| 2003/0042137 | A1 | 3/2003 | Mao et al. |
| 2003/0050547 | A1 | 3/2003 | Lebel et al. |
| 2003/0068666 | A1 | 4/2003 | Zweig |
| 2003/0100821 | A1 | 5/2003 | Heller et al. |
| 2004/0061232 | A1 | 4/2004 | Shah et al. |
| 2005/0148832 | A1 | 7/2005 | Reghabi et al. |
| 2005/0215871 | A1 | 9/2005 | Feldman et al. |
| 2006/0004272 | A1 | 1/2006 | Shah et al. |
| 2006/0076236 | A1 | 4/2006 | Shah et al. |
| 2006/0257996 | A1 | 11/2006 | Simpson et al. |
| 2007/0007132 | A1 | 1/2007 | Mao et al. |
| 2007/0027385 | A1 | 2/2007 | Brister et al. |
| 2007/0042377 | A1 | 2/2007 | Gao et al. |
| 2007/0095661 | A1 | 5/2007 | Wang et al. |
| 2007/0131547 | A1 | 6/2007 | Nomoto et al. |
| 2007/0213611 | A1 | 9/2007 | Simpson et al. |
| 2007/0235331 | A1 | 10/2007 | Simpson et al. |
| 2007/0270672 | A1 | 11/2007 | Hayter |
| 2008/0179187 | A1 | 7/2008 | Ouyang et al. |
| 2008/0319295 | A1 | 12/2008 | Bernstein et al. |
| 2009/0099434 | A1* | 4/2009 | Liu ...................... A61B 5/4839 600/347 |
| 2009/0166194 | A1 | 7/2009 | Sato et al. |
| 2009/0242425 | A1 | 10/2009 | Kamath et al. |
| 2009/0294306 | A1 | 12/2009 | Feldman et al. |
| 2010/0185070 | A1 | 7/2010 | Brister et al. |
| 2010/0198034 | A1 | 8/2010 | Thomas et al. |
| 2010/0213057 | A1 | 8/2010 | Feldman et al. |
| 2010/0230285 | A1 | 9/2010 | Hoss et al. |
| 2010/0267161 | A1 | 10/2010 | Wu et al. |
| 2010/0268043 | A1 | 10/2010 | Yodfat et al. |
| 2010/0324392 | A1 | 12/2010 | Yee et al. |
| 2010/0326842 | A1 | 12/2010 | Mazza et al. |
| 2011/0039165 | A1 | 2/2011 | Sugiyama et al. |
| 2011/0046467 | A1 | 2/2011 | Simpson et al. |
| 2011/0065008 | A1 | 3/2011 | Nakagawa et al. |
| 2011/0120865 | A1 | 5/2011 | Bommakanti et al. |
| 2011/0124993 | A1 | 5/2011 | Bommakanti et al. |
| 2011/0124994 | A1 | 5/2011 | Bommakanti et al. |
| 2011/0126188 | A1 | 5/2011 | Bernstein et al. |
| 2011/0213057 | A1 | 9/2011 | Fenn et al. |
| 2011/0213225 | A1 | 9/2011 | Bernstein et al. |
| 2011/0256024 | A1 | 10/2011 | Cole et al. |
| 2011/0257495 | A1 | 10/2011 | Hoss et al. |
| 2012/0132525 | A1 | 5/2012 | Liu et al. |
| 2012/0138484 | A1 | 6/2012 | Bommakanti et al. |
| 2012/0150005 | A1 | 6/2012 | Hoss et al. |
| 2012/0157801 | A1 | 6/2012 | Hoss et al. |
| 2012/0181189 | A1 | 7/2012 | Merchant |
| 2012/0186997 | A1 | 7/2012 | Li et al. |
| 2012/0245447 | A1 | 9/2012 | Karan et al. |
| 2012/0283537 | A1 | 11/2012 | Petisce et al. |
| 2012/0296186 | A1 | 11/2012 | Ouyang et al. |
| 2012/0323098 | A1 | 12/2012 | Moein et al. |
| 2013/0059212 | A1 | 3/2013 | Kusumegi et al. |
| 2013/0116524 | A1 | 5/2013 | Cole et al. |
| 2013/0131478 | A1 | 5/2013 | Simpson et al. |
| 2013/0211219 | A1 | 8/2013 | Coppeta et al. |
| 2013/0231542 | A1 | 9/2013 | Simpson et al. |
| 2013/0245412 | A1 | 9/2013 | Rong et al. |
| 2013/0324820 | A1 | 12/2013 | Petillo et al. |
| 2014/0054171 | A1 | 2/2014 | Feldman et al. |
| 2014/0088389 | A1* | 3/2014 | Simpson ................ C12Q 1/002 600/345 |
| 2014/0127728 | A1 | 5/2014 | Wilsey |
| 2014/0176338 | A1 | 6/2014 | He et al. |
| 2014/0262776 | A1 | 9/2014 | Martin et al. |
| 2014/0262777 | A1 | 9/2014 | Zhao et al. |
| 2015/0038814 | A1 | 2/2015 | Staib et al. |

(56) References Cited

U.S. PATENT DOCUMENTS

| | | | |
|---|---|---|---|
| 2015/0076004 | A1 | 3/2015 | Gerber et al. |
| 2015/0207796 | A1 | 7/2015 | Love et al. |
| 2016/0045147 | A1 | 2/2016 | Ouyang et al. |
| 2016/0319232 | A1 | 11/2016 | Noritomi et al. |
| 2016/0328991 | A1 | 11/2016 | Simpson et al. |
| 2016/0345882 | A1 | 12/2016 | Wu et al. |
| 2016/0354542 | A1 | 12/2016 | Ward et al. |
| 2016/0355862 | A1 | 12/2016 | Deng et al. |
| 2017/0156652 | A1 | 6/2017 | Qiang et al. |
| 2017/0191958 | A1 | 7/2017 | Gerber et al. |
| 2017/0202491 | A1 | 7/2017 | Heller et al. |
| 2017/0315077 | A1 | 11/2017 | Rao et al. |
| 2017/0319111 | A1 | 11/2017 | Simpson et al. |
| 2018/0014766 | A1 | 1/2018 | Ouyang et al. |
| 2018/0116604 | A1 | 5/2018 | Newberry |
| 2018/0275088 | A1 | 9/2018 | Huff et al. |
| 2019/0004005 | A1 | 1/2019 | Oja et al. |
| 2019/0024130 | A1 | 1/2019 | Ouyang et al. |
| 2019/0125230 | A1 | 5/2019 | Feldman |
| 2019/0271658 | A1 | 9/2019 | Haneda et al. |
| 2019/0274598 | A1 | 9/2019 | Scott et al. |
| 2019/0320947 | A1 | 10/2019 | Chen et al. |
| 2020/0069226 | A1 | 3/2020 | Hahn et al. |
| 2020/0237275 | A1 | 7/2020 | Feldman et al. |
| 2020/0237276 | A1 | 7/2020 | Oja et al. |
| 2020/0237277 | A1 | 7/2020 | Ouyang et al. |
| 2020/0241015 | A1 | 7/2020 | Ouyang et al. |
| 2021/0137431 | A1 | 5/2021 | Oja et al. |
| 2022/0056500 | A1 | 2/2022 | Ouyang et al. |
| 2022/0168727 | A1 | 6/2022 | Baldwa |
| 2022/0386910 | A1 | 12/2022 | Oja et al. |
| 2022/0389475 | A1 | 12/2022 | Ouyang et al. |
| 2022/0395202 | A1 | 12/2022 | Ouyang et al. |
| 2022/0396820 | A1 | 12/2022 | Ouyang et al. |
| 2023/0054564 | A1 | 2/2023 | Ouyang et al. |
| 2023/0080107 | A1 | 3/2023 | Ouyang et al. |
| 2023/0118818 | A1 | 4/2023 | Feldman et al. |
| 2023/0119512 | A1 | 4/2023 | Feldman et al. |
| 2023/0121101 | A1 | 4/2023 | Feldman et al. |
| 2023/0121367 | A1 | 4/2023 | Feldman et al. |
| 2023/0121769 | A1 | 4/2023 | Feldman et al. |
| 2023/0122702 | A1 | 4/2023 | Feldman et al. |
| 2023/0123384 | A1 | 4/2023 | Feldman et al. |
| 2023/0128038 | A1 | 4/2023 | Feldman et al. |
| 2024/0247297 | A1 | 7/2024 | Ouyang et al. |
| 2024/0350047 | A1 | 10/2024 | Oja et al. |
| 2025/0221643 | A1 | 7/2025 | Ouyang et al. |
| 2025/0261884 | A1 | 8/2025 | Oja et al. |
| 2026/0002188 | A1 | 1/2026 | Ouyang et al. |
| 2026/0002189 | A1 | 1/2026 | Ouyang et al. |
| 2026/0002190 | A1 | 1/2026 | Ouyang et al. |
| 2026/0002191 | A1 | 1/2026 | Ouyang et al. |
| 2026/0002192 | A1 | 1/2026 | Ouyang et al. |
| 2026/0002193 | A1 | 1/2026 | Ouyang et al. |
| 2026/0020798 | A1 | 1/2026 | Oja et al. |
| 2026/0020799 | A1 | 1/2026 | Oja et al. |

FOREIGN PATENT DOCUMENTS

| | | | |
|---|---|---|---|
| CN | 113164106 | A | 7/2021 |
| EP | 0990706 | A1 | 4/2000 |
| EP | 3394252 | A1 | 10/2018 |
| EP | 3414325 | A1 | 12/2018 |
| EP | 3597765 | A1 | 1/2020 |
| EP | 4084689 | A1 | 11/2022 |
| GB | 2067764 | A | 7/1981 |
| JP | 2001506742 | A | 5/2001 |
| JP | 2007510155 | A | 4/2007 |
| JP | 2007290504 | A | 11/2007 |
| JP | 2010517054 | A | 5/2010 |
| JP | 2010530790 | A | 9/2010 |
| JP | 2011136186 | A | 7/2011 |
| JP | 2013504053 | A | 2/2013 |
| JP | 2014503080 | A | 2/2014 |
| JP | 2014160024 | A | 9/2014 |
| JP | 2015198960 | A | 11/2015 |
| JP | 2018029983 | A | 3/2018 |
| JP | 2022172249 | A | 11/2022 |
| WO | WO-03056319 | A2 | 7/2003 |
| WO | WO-2005040404 | A1 | 5/2005 |
| WO | WO-2008041984 | A1 | 4/2008 |
| WO | WO-2009105337 | A2 | 8/2009 |
| WO | WO-2010030912 | A1 | 3/2010 |
| WO | WO-2011030093 | A1 | 3/2011 |
| WO | WO-2012100130 | A1 | 7/2012 |
| WO | WO-2015150263 | A1 | 10/2015 |
| WO | WO-2015195352 | A1 | 12/2015 |
| WO | WO-2016025064 | A1 | 2/2016 |
| WO | WO-2016174456 | A1 | 11/2016 |
| WO | WO-2016174458 | A1 | 11/2016 |
| WO | WO-2017151952 | A1 | 9/2017 |
| WO | WO-2018067235 | A1 | 4/2018 |
| WO | WO-2018106129 | A1 | 6/2018 |
| WO | WO-2019006413 | A1 | 1/2019 |

OTHER PUBLICATIONS

Burmeister, J.J., and Gerhardt, G.A., "Self-referencing Ceramic-based Multisite Microelectrodes for the Detection and Elimination of Interferences from the Measurement of L-glutamate and Other Analytes," Analytical Chemistry, 73(5):1037-1042, American Chemical Society, United States (Mar. 2001).

Cardosi, M., and Liu, Z., "Amperometric Glucose Sensors for Whole Blood Measurement Based on Dehydrogenase Enzymes," Chapter 13 in Dehydrogenases, pp. 319-354, Canuto, R. A., ed., InTechOpen, Croatia, 36 pages (Nov. 2012).

Co-pending Application, U.S. Appl. No. 19/320,168, filed Sep. 5, 2025.

Co-pending Application, U.S. Appl. No. 19/320,172, filed Sep. 5, 2025.

Co-pending Application, U.S. Appl. No. 19/320,176, filed Sep. 5, 2025.

Co-pending Application, U.S. Appl. No. 19/320,180, filed Sep. 5, 2025.

Co-pending Application, U.S. Appl. No. 19/321,772, filed Sep. 8, 2025.

Co-pending Application, U.S. Appl. No. 19/321,781, filed Sep. 8, 2025.

D'Allegro, J., "Soon your car will know when you are having a heart attack and know how to react," Modem Medicine, CNBC, Accessed at https://www.cnbc.com/2017/11/17/cars-will-know-when-youre-having-a-heart-attack-and-how-to-react.html, Accessed on Oct. 10, 2023, (Nov. 17, 2017), 4 Pages.

Del Cano, R., et al., Ketone Bodies Detection: Wearable and Mobile Sensors for Personalized Medicine an Nutrition, Trends in Analytical Chemistry 159:116938, (Feb. 2023), 11 pages.

English Language Translation of JP2014160024A, 22 Pages.

Final Office Action for U.S. Appl. No. 16/582,583 mailed on Apr. 19, 2023, 18 pages.

Final Office Action for U.S. Appl. No. 16/582,583 mailed on May 16, 2024, 21 pages.

Final Office Action for U.S. Appl. No. 16/774,835 mailed on Apr. 18, 2022, 24 pages.

Final Office Action for U.S. Appl. No. 16/774,835 mailed on Dec. 24, 2024, 25 pages.

Final Office Action for U.S. Appl. No. 16/774,909 mailed on Apr. 9, 2024, 13 pages.

Final Office Action for U.S. Appl. No. 17/138,477, mailed on Apr. 3, 2024, 12 pages.

Final Office Action for U.S. Appl. No. 17/138,477, mailed on Mar. 17, 2023, 12 pages.

Final Office Action for U.S. Appl. No. 17/403,258, mailed on Nov. 13, 2024, 11 pages.

Final Office Action for U.S. Appl. No. 18/068,019 mailed on Oct. 17, 2024, 17 pages.

Final Office Action for U.S. Appl. No. 18/068,072 mailed on Oct. 18, 2024, 13 pages.

(56) References Cited

OTHER PUBLICATIONS

Final Office Action for U.S. Appl. No. 18/068,077 mailed on Jan. 28, 2025, 26 pages.
Final Office Action for U.S. Appl. No. 18/068,704 mailed on Jan. 24, 2025, 16 pages.
Final Office Action for U.S. Appl. No. 18/068,714, mailed on Oct. 18, 2024, 15 pages.
Final Office Action for U.S. Appl. No. 18/068,860 mailed on Oct. 18, 2024, 15 pages.
Final Office Action for U.S. Appl. No. 16/774,835, mailed on Sep. 12, 2023, 16 pages.
Final Office Action for U.S. Appl. No. 16/774,909, mailed on Dec. 21, 2022, 13 pages.
Final Office Action for U.S. Appl. No. 17/818,912, mailed on Oct. 25, 2024, 11 pages.
Final Office Action for U.S. Appl. No. 17/819,038, mailed on Aug. 26, 2024, 10 pages.
Final Office Action mailed Dec. 30, 2020, in U.S. Appl. No. 16/081,162, Ouyang, T., et al., filed Aug. 30, 2018, 12 pages.
Final Office Action mailed Jul. 30, 2024, in U.S. Appl. No. 17/818,143, Ouyang, T., et al., filed Aug. 8, 2022, 11 pages.
Final Office Action mailed Jul. 30, 2024, in U.S. Appl. No. 17/818,770, Ouyang, T., et al., filed Aug. 10, 2022, 13 pages.
Guiseppi-Elie, A., et al., "Design of a subcutaneous implantable biochip for monitoring of glucose and lactate," IEEE Sensors Journal 5(3):345-355, Institute of Electrical and Electronics Engineers, United States (Jun. 2005).
International Search Report and Written Opinion for International Application No. PCT/US2019/052942, dated on Nov. 28, 2019, 17 pages.
International Search Report and Written Opinion for International Application No. PCT/US2020/015365, mailed May 28, 2020, 14 pages.
International Search Report and Written Opinion for International Application No. PCT/US2020/015400. mailed on Apr. 9, 2020, 14 pages.
International Search Report and Written Opinion for International Application No. PCT/US2020/015321, mailed on Apr. 9, 2020, 14 pages.
International Search Report and Written Opinion for PCT/US2017/020495, mailed on Jul. 10, 2017, 23 pages.
Monteiro, T et al., "Construction of Effective Disposable Biosensors for Point of Care Testing of Nitrite." Talanta 142:246-251, Elsevier, Netherlands (Sep. 2015).
Mueller. S., et al.. The GOX/CAT system: A Novel Enzymatic Method to Independently Control Hydrogen Peroxide and Hypoxia in Cell Culture Advances in Medical Sciences 54(2): 121-135, Elsevier, Netherlands (Dec. 2009).
Nakabayashi, Y., et al., "Evaluation of Osmium(II) Complexes as Electron Transfer Mediators Accessible for Amperometric Glucose Sensors," Analytical Sciences 17(8):945-950, Springer, Switzerland (Aug. 2001).
Nikitina, O., et al., "Bi-enzyme Biosensor Based on NAD+—and Glutathione-dependent Recombinant Formaldehyde Dehydrogenase and Diaphorase for Formaldehyde Assay," Sensors and Actuators 125(1):1-9, (Jul. 2007).
Non-Final Office Action for U.S. Appl. No. 16/582,583, mailed on Oct. 3, 2023, 21 pages.
Non-Final Office Action for U.S. Appl. No. 16/582,583 mailed on Sep. 1, 2022, 20 pages.
Non-Final Office Action for U.S. Appl. No. 16/774,835 mailed on Apr. 15, 2024, 16 pages.
Non-Final Office Action for U.S. Appl. No. 16/774,835 mailed on Sep. 17, 2021, Feldman, B. J., et al., filed Jan. 28, 2020, 21 pages.
Non-Final Office Action for U.S. Appl. No. 16/774,841, mailed on Jun. 24, 2022, 10 pages.
Non-Final Office Action for U.S. Appl. No. 16/774,841, mailed on Nov. 16, 2022,10 pages.
Non-Final Office Action for U.S. Appl. No. 16/774,909, mailed on Aug. 8, 2023, 14 pages.
Non-Final Office Action for U.S. Appl. No. 16/774,909, mailed on Jun. 2, 2022, 13 pages.
Non-Final Office Action for U.S. Appl. No. 17/138,477. mailed on Aug. 21, 2023, 12 pages.
Non-Final Office Action for U.S. Appl. No. 17/138,477, mailed on Sep. 12, 2022, 10 pages.
Non-Final Office Action for U.S. Appl. No. 17/151,274, mailed on Nov. 25, 2022, 13 pages.
Non-Final Office Action for U.S. Appl. No. 17/151,274, mailed on Sep. 7, 2023, 13 pages.
Non-Final Office Action for U.S. Appl. No. 17/818,143, mailed on Nov. 14, 2024, 12 pages.
Non-Final Office Action for U.S. Appl. No. 17/818,770, mailed on Nov. 5, 2024, 14 pages.
Non-Final Office Action for U.S. Appl. No. 17/819,099 mailed on Mar. 5, 2024. 14 pages.
Non-Final Office Action for U.S. Appl. No. 17/819,099, mailed on Sep. 22, 2023, 24 pages.
Non-Final Office Action for U.S. Appl. No. 18/068,019, dated on Feb. 29, 2024, 12 Pages.
Non-Final Office Action for U.S. Appl. No. 18/068,072 mailed on Feb. 15, 2024, 13 pages.
Non-Final Office Action for U.S. Appl. No. 18/068,077 mailed on Jul. 30, 2024, 14 pages.
Non-Final Office Action for U.S. Appl. No. 18/068,704 mailed on Jun. 18, 2024, 14 pages.
Non-Final Office Action for U.S. Appl. No. 18/068,714, mailed on Mar. 5, 2024, 14 Pages.
Non-Final Office Action for U.S. Appl. No. 18/068,807, mailed on Jan. 29, 2025, 25 pages.
Non-Final Office Action for U.S. Appl. No. 18/068,834 mailed on Jan. 31, 2024, 10 pages.
Non-Final Office Action for U.S. Appl. No. 18/068,834 mailed on Oct. 18, 2024, 15 pages.
Non-Final Office Action for U.S. Appl. No. 18/068,860 mailed on Jul. 15, 2024, 13 pages.
Non-Final Office Action for U.S. Appl. No. 16/774,835, mailed on Mar. 2, 2023, 14 pages.
Non-Final Office Action mailed Apr. 26, 2024, in U.S. Appl. No. 17/818,912, Ouyang, T., et al., filed Aug. 10, 2022, 13 pages.
Non-Final Office Action mailed Jan. 24, 2024, in U.S. Appl. No. 17/818,143, Ouyang, T., et al., filed Aug. 8, 2022, 14 pages.
Non-Final Office Action mailed Jan. 31, 2024, in U.S. Appl. No. 17/819,038, Ouyang, T., et al., filed Aug. 11, 2022, 11 pages.
Non-Final Office Action mailed Jul. 22, 2020, in U.S. Appl. No. 16/081,162, Ouyang, T., et al., filed Aug. 30, 2018, 10 pages.
Non-Final Office Action mailed Mar. 12, 2024, in U.S. Appl. No. 17/818,770, Ouyang, T., et al., filed Aug. 10, 2022, 14 pages.
Non-Final Office Action mailed Mar. 25, 2024, in U.S. Appl. No. 17/403,258, Ouyang, T., et al., filed Aug. 16, 2021, 9 pages.
Non-Final Office Action mailed May 7, 2024, in U.S. Appl. No. 17/819,151, Ouyang, T., et al., filed Aug. 11, 2022, 13 pages.
Non-Final Office Action mailed Sep. 16, 2024, in U.S. Appl. No. 18/597,704, Ouyang, T., et al., filed Mar. 6, 2024, 9 pages.
Notice of Allowance for U.S. Appl. No. 16/774,841 mailed on Aug. 16, 2023, 8 pages.
Notice of Allowance for U.S. Appl. No. 16/774,841 mailed on Feb. 9, 2024, 3 pages.
Notice of Allowance for U.S. Appl. No. 17/151,274 mailed on Feb. 7, 2024. 8 pages.
Notice of Allowance for U.S. Appl. No. 17/819,099, dated on Jul. 9, 2024, 8 pages.
Notice of Allowance for U.S. Appl. No. 17/819,151, mailed on Oct. 22, 2024, 7 pages.
Notice of Allowance mailed Apr. 13, 2021 in U.S. Appl. No. 16/081,162, Ouyang, T., et al., Filed Aug. 30, 2018, 7 pages.
Pickup, J.C., "Glucose Sensors: Present and Future," International Textbook of Diabetes Mellitus, Third Edition, Defronzo, R.A., eds., 2:1686-1694, John Wiley & Sons Inc., United States (2004), 13 Pages.
Pundir, C.S., et al., "Biosensing Methods for Determination of Creatinine: A Review," Biosensors and Bioelectronics Journal 126:707-724, Elsevier Advanced Technology, United Kingdom (Feb. 2019).

(56) References Cited

OTHER PUBLICATIONS

Shi, G., et al., "The Study of Nafion/xanthine Oxidase/au Colloid Chemically Modified Biosensor and Its Application in the Determination of Hypoxanthine in Myocardial Cells in Vivo," The Analyst 127(3):396-400, Royal Society of Chemistry, United Kingdom (Mar. 2002).

Zhang, J.Y., et al., "Continuous Ketone Monitoring: A New Paradigm for Physiologic Monitoring," Journal of Diabetes Science and Technology 15(4):775-780, Sage, United States (Jul. 2021).

Co-pending application, U.S. Appl. No. 19/340,445, filed Sep. 25, 2025.

Co-pending application, U.S. Appl. No. 19/340,458, filed Sep. 25, 2025.

Franco, J.H., et al., "Product Analysis of Operating an Ethanol/O2 Biofuel Cell Shows the Synergy between Enzymes within an Enzymatic Cascade," Journal of The Electrochemical Society 165(9):H575-H579, (2018).

Kowalewska, B., and Kulesza, P.J., "Toward More Efficient Bioelectrocatalytic Oxidation of Ethanol for Amperometric Sensing and Biofuel Cell Technology," Analytical Chemistry 84(21):9564-9571, American Chemical Society, United States (Nov. 2012).

Non-Final Office Action for U.S. Appl. No. 18/068,704 mailed on Dec. 16, 2025; 49 pages.

Non-Final Office Action for U.S. Appl. No. 19/320,168, mailed on Dec. 15, 2025, 8 pages.

Non-Final Office Action for U.S. Appl. No. 19/320,172 mailed on Dec. 4, 2025; 10 pages.

Non-Final Office Action for U.S. Appl. No. 19/320,176 mailed on Dec. 3, 2025, 15 pages.

Non-Final Office Action for U.S. Appl. No. 19/320,180 mailed on Dec. 16, 2025; 17 pages.

Non-Final Office Action for U.S. Appl. No. 19/340,445 mailed on Nov. 28, 2025, 20 pages.

Non-Final Office Action for U.S. Appl. No. 19/340,458 mailed on Nov. 28, 2025, 22 pages.

Notice of Allowance for U.S. Appl. No. 16/774,835 mailed on Jan. 20, 2026, 9 pages.

Notice of Allowance for U.S. Appl. No. 17/818,143, mailed on Jan. 21, 2026, 8 pages.

Notice of Allowance for U.S. Appl. No. 17/818,143 mailed on Oct. 28, 2025; 7 pages.

Notice of Allowance for U.S. Appl. No. 18/068,072, mailed on Jan. 23, 2026, 5 pages.

Notice of Allowance for U.S. Appl. No. 18/068,860, mailed on Jan. 22, 2026, 5 pages.

Notice of Allowance for U.S. Appl. No. 18/596,447, mailed on Jan. 21, 2026, 8 pages.

Notice of Allowance for U.S. Appl. No. 18/597,704 mailed on Jan. 27, 2026, 7 pages.

* cited by examiner

ANALYTE SENSORS EMPLOYING MULTIPLE ENZYMES AND METHODS ASSOCIATED THEREWITH

BACKGROUND

The detection of various analytes within an individual can sometimes be vital for monitoring the condition of their health and well-being. Deviation from normal analyte levels can often be indicative of an underlying physiological condition, such as a metabolic condition or illness, or exposure to particular environmental conditions.

Any analyte may be suitable for a physiological analysis provided that a suitable chemistry can be identified for sensing the analyte. To this end, amperometric sensors configured for assaying glucose in vivo have been developed and refined over recent years. Other analytes commonly subject to physiological dysregulation that may similarly be desirable to monitor either ex vivo or in vivo include, but are not limited to, lactate, oxygen, pH, A1c, ketones, drug levels, and the like.

Analyte monitoring in an individual may take place periodically or continuously over a period of time. Periodic analyte monitoring may take place by withdrawing a sample of bodily fluid, such as blood, at set time intervals and analyzing ex vivo. Continuous analyte monitoring may be conducted using one or more sensors that remain at least partially implanted within a tissue of an individual, such as dermally, subcutaneously or intravenously, so that analyses may be conducted in vivo. Implanted sensors may collect analyte data at any dictated rate, depending on an individual's particular health needs and/or previously measured analyte levels.

Periodic, ex vivo analyte monitoring can be sufficient to determine the physiological condition of many individuals. However, ex vivo analyte monitoring may be inconvenient or painful for some persons. Moreover, there is no way to recover lost data if an analyte measurement is not obtained at an appropriate time.

Continuous analyte monitoring with an in vivo implanted sensor may be a more desirable approach for individuals having severe analyte dysregulation an/or rapidly fluctuating analyte levels, although it can also be beneficial for other individuals as well. While continuous analyte monitoring with an implanted sensor can be advantageous, there are challenges associated with these types of measurements. Intravenous analyte sensors have the advantage of providing analyte concentrations directly from blood, but they are invasive and can sometimes be painful for an individual to wear, particularly over an extended period. Subcutaneous, interstitial, or dermal analyte sensors can often be less painful for an individual to wear and can provide sufficient measurement accuracy in many cases.

In vivo analyte sensors typically are configured to analyze for a single analyte in order to provide specific analyses, often employing an enzyme to provide the analytical specificity. However, the physiological interplay between various combinations of analytes can make multi-analyte analyses desirable in certain instances as well. At present, in vivo analysis of multiple analytes may necessitate using a corresponding number of analyte sensors configured for analyzing each analyte. This approach may be inconvenient due to the requirement for an individual to wear multiple analyte sensors. In addition, multiple analyte sensors may represent an unacceptable cost burden for an individual or an insurance provider. There is also an increased opportunity for one of the independent analyte sensors to fail during such sensing protocols.

In vivo analyte sensors may also include a membrane disposed over at least the implanted portion of the analyte sensor. In one aspect, the membrane may improve biocompatibility of the analyte sensor. In another aspect, the membrane may be permeable or semi-permeable to an analyte of interest and limit the overall analyte flux to the active area of the analyte sensor. That is, the membrane may function as a mass transport limiting membrane. Limiting analyte access to the active area of the sensor with a mass transport limiting membrane can aid in avoiding sensor overload (saturation), thereby improving detection performance and accuracy. Such membranes may be highly specific toward limiting mass transport of a particular analyte, with other substances permeating through the membrane at significantly different rates. The differing membrane permeability of various potential analytes represents a significant hurdle for developing analyte sensors configured for assaying multiple analytes. Namely, the differing membrane permeability values may lead to significantly different sensitivities for the multiple analytes, thereby complicating analyses. The differing sensitivities for multiple analytes may sometimes be partially compensated for by using active areas of different sizes (e.g., smaller active areas for analytes having high sensitivity/permeability and larger active areas for analytes having lower sensitivity/permeability), but this approach may present significant manufacturing challenges and may not be applicable in all cases.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
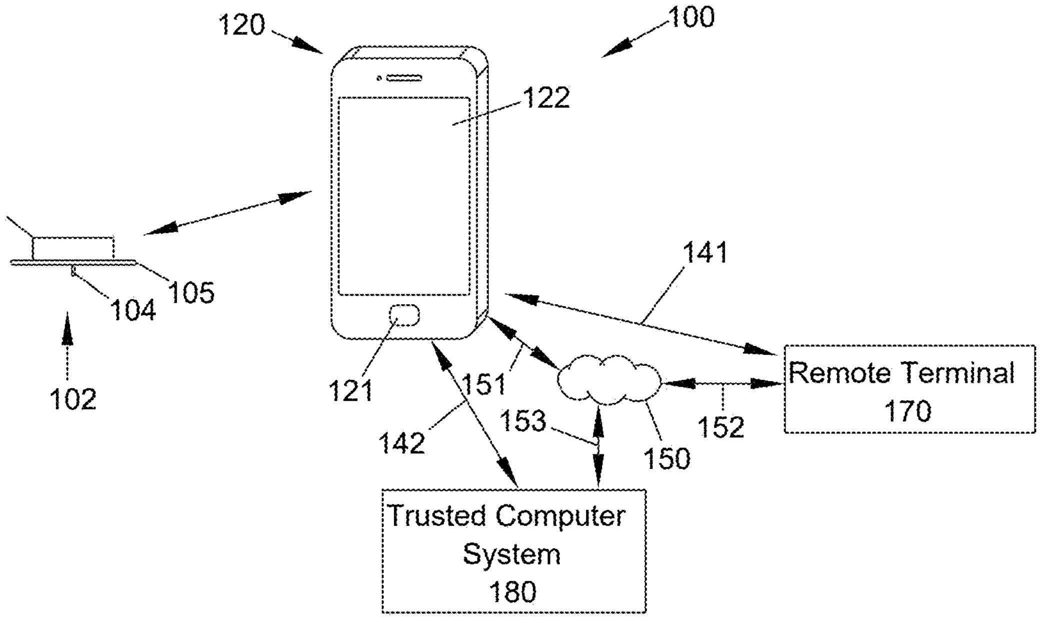
FIG. 1 shows a diagram of an illustrative sensing system that may incorporate an analyte sensor of the present disclosure.

The present disclosure generally describes analyte sensors and methods employing multiple enzymes for detection and, more specifically, analyte sensors and methods in which multiple enzymes may function independently or in concert to detect one or more analytes.

As discussed above, analyte sensors are commonly used to detect a single analyte. If detection of multiple analytes is desired, a corresponding number of analyte sensors may be employed. This approach may be undesirable due to, among other things, cost concerns, the necessity for an individual to wear multiple analyte sensors, and an increased likelihood of individual sensor failure.

Some analyte sensors utilize an enzymatic reaction as the basis for detecting an analyte of interest. Since enzymes often display reaction specificity toward a particular substrate or related class of substrates, they may provide analyte sensors having detection chemistry configured to analyze for a single analyte of interest. As such, analyte sensors for analyzing a single analyte usually incorporate only a corresponding single enzyme to promote a suitable enzymatic reaction for facilitating detection. At present, it can be rather difficult to incorporate multiple enzymes in an analyte sensor in order to provide detection capabilities for multiple analytes. Reasons include differences in analyte sensitivity and potential incompatibility of one or more of the enzymes to a given set of analysis conditions.

In contrast to analyte sensors featuring a single enzyme, the present disclosure describes analyte sensors in which multiple enzymes are present in the active area(s) of the sensors. A number of advantages may be realized by incorporating multiple enzymes in an analyte sensor in the various manners described herein. In some sensor configurations of the present disclosure, the multiple enzymes may facilitate independent detection of multiple analytes, such as glucose and lactate. Membranes configured to provide tailored permeability for multiple analytes are also described herein, which may facilitate analyte detection with a single analyte sensor by levelizing the sensor's sensitivity toward each analyte. In other sensor configurations of the present disclosure, multiple enzymes may be chosen to function in concert to facilitate detection of a single analyte of interest, which may otherwise be problematic or impossible to assay using a single enzyme. In any event, fewer electrodes may be needed to detect a given analyte or set of analytes than would otherwise be feasible. Moreover, the present disclosure may afford sensors having a reduced size and a decreased complexity of their measurement electronics than would otherwise be possible. Thus, analyte sensors employing multiple enzymes in various configurations may facilitate efficient detection of one or more analytes according to the disclosure herein.

Analyte sensors containing multiple enzymes, whether operating independently or in concert, may function with enhanced stability in the presence of an appropriate stabilizer. Stabilizers that may be used include, for example, catalase or albumin (e.g., bovine serum albumin or human serum albumin). Catalase is known for its ability to clear reactive species, such as peroxide, from biological environments. Albumins, in contrast, are not believed to exhibit functionality to clear reactive species, and their ability to stabilize the response of the analyte sensors of the present disclosure is surprising as a result.

Before describing the analyte sensors of the present disclosure in more detail, a brief overview of suitable in vivo analyte sensor configurations and sensor systems employing the analyte sensors will first be provided so that the embodiments of the present disclosure may be better understood. It is to be understood that any of the sensor systems and analyte sensor configurations described hereinafter may feature multiple enzymes, in accordance with the various embodiments of the present disclosure.

FIG. 1 shows a diagram of an illustrative sensing system that may incorporate an analyte sensor of the present disclosure. As shown, sensing system 100 includes sensor control device 102 and reader device 120 that are configured to communicate with one another over a local communication path or link, which may be wired or wireless, uni- or bi-directional, and encrypted or non-encrypted. Reader device 120 may constitute an output medium for viewing analyte concentrations and alerts or notifications determined by sensor 104 or a processor associated therewith, as well as allowing for one or more user inputs, according to some embodiments. Reader device 120 may be a multi-purpose smartphone or a dedicated electronic reader instrument. While only one reader device 120 is shown, multiple reader devices 120 may be present in certain instances. Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Reader device 120 may also or alternately be in communication with network 150 (e.g., a mobile telephone network, the internet, or a cloud server) via communication path/link 151. Network 150 may be further communicatively coupled to remote terminal 170 via communication path/link 152 and/or trusted computer system 180 via communication path/link 153. Alternately, sensor 104 may communicate directly with remote terminal 170 and/or trusted computer systems 180 without an intervening reader device 120 being present. For example, sensor 104 may communicate with remote terminal 170 and/or trusted computer system 180 through a direct communication link to network 150, according to some embodiments, as described in U.S. Patent Application Publication 2011/0213225 an incorporated herein by reference in its entirety. Any suitable electronic communication protocol may be used for each of the communication paths or links, such as near field communication (NFC), radio frequency identification (RFID), BLUETOOTH® or BLUETOOTH® Low Energy protocols, WiFi, or the like. Remote terminal 170 and/or trusted computer system 180 may be accessible, according to some embodiments, by individuals other than a primary user who have an interest in the user's analyte levels. Reader device 120 may comprise display 122 and optional input component 121. Display 122 may comprise a touch-screen interface, according to some embodiments.

Sensor control device 102 includes sensor housing 103, which may house circuitry and a power source for operating sensor 104. Optionally, the power source and/or active circuitry may be omitted. A processor (not shown) may be communicatively coupled to sensor 104, with the processor being physically located within sensor housing 103 or reader device 120. Sensor 104 protrudes from the underside of sensor housing 103 and extends through adhesive layer 105, which is adapted for adhering sensor housing 103 to a tissue surface, such as skin, according to some embodiments.

Sensor 104 is adapted to be at least partially inserted into a tissue of interest, such as within the dermal or subcutaneous layer of the skin. Sensor 104 may comprise a sensor tail of sufficient length for insertion to a desired depth in a given tissue. The sensor tail may comprise at least one working electrode and one or more active areas (sensing regions/spots or sensing layers) located upon the at least one working electrode and that are active for sensing one or more analytes of interest. Collectively, the one or more active areas may comprise multiple enzymes, according to one or more embodiments of the present disclosure. The active areas may include a polymeric material to which at least some of the enzymes are covalently bonded, according to some embodiments. In various embodiments of the present disclosure, analytes may be monitored in any biological fluid of interest such as dermal fluid, interstitial fluid, plasma, blood, lymph, synovial fluid, cerebrospinal fluid, saliva, bronchoalveolar lavage, amniotic fluid, or the like. In particular embodiments, analyte sensors of the present disclosure may be adapted for assaying dermal fluid or interstitial fluid.

In some embodiments, sensor 104 may automatically forward data to reader device 120. For example, analyte concentration data may be communicated automatically and periodically, such as at a certain frequency as data is obtained or after a certain time period has passed, with the data being stored in a memory until transmittal (e.g., every minute, five minutes, or other predetermined time period). In other embodiments, sensor 104 may communicate with reader device 120 in a non-automatic manner and not according to a set schedule. For example, data may be communicated from sensor 104 using RFID technology when the sensor electronics are brought into communication range of reader device 120. Until communicated to reader device 120, data may remain stored in a memory of sensor 104. Thus, a patient does not have to maintain close proximity to reader device 120 at all times, and can instead upload data at a convenient time. In yet other embodiments, a combination of automatic and non-automatic data transfer may be implemented. For example, data transfer may continue on an automatic basis until reader device 120 is no longer in communication range of sensor 104.

An introducer may be present transiently to promote introduction of sensor 104 into a tissue. In illustrative embodiments, the introducer may comprise a needle or similar sharp. It is to be recognized that other types of introducers, such as sheaths or blades, may be present in alternative embodiments. More specifically, the needle or other introducer may transiently reside in proximity to sensor 104 prior to tissue insertion and then be withdrawn afterward. While present, the needle or other introducer may facilitate insertion of sensor 104 into a tissue by opening an access pathway for sensor 104 to follow. For example, the needle may facilitate penetration of the epidermis as an access pathway to the dermis to allow implantation of sensor 104 to take place, according to one or more embodiments. After opening the access pathway, the needle or other introducer may be withdrawn so that it does not represent a sharps hazard. In illustrative embodiments, suitable needles may be solid or hollow, beveled or non-beveled, and/or circular or non-circular in cross-section. In more particular embodiments, suitable needles may be comparable in cross-sectional diameter and/or tip design to an acupuncture needle, which may have a cross-sectional diameter of about 250 microns. It is to be recognized, however, that suitable needles may have a larger or smaller cross-sectional diameter if needed for particular applications.

In some embodiments, a tip of the needle (while present) may be angled over the terminus of sensor 104, such that the needle penetrates a tissue first and opens an access pathway for sensor 104. In other illustrative embodiments, sensor 104 may reside within a lumen or groove of the needle, with the needle similarly opening an access pathway for sensor 104. In either case, the needle is subsequently withdrawn after facilitating sensor insertion.

The analyte sensors described herein may feature multiple enzymes upon the active area(s) of a single working electrode or upon two or more separate working electrodes. Single working electrode configurations for an analyte sensor may employ two-electrode or three-electrode detection motifs, according to various embodiments of the present disclosure. Sensor configurations featuring a single working electrode are described hereinafter in reference to FIGS. 2A-2C. Sensor configurations featuring multiple working electrodes are described separately thereafter in reference to FIG. 3. Multiple enzymes may be incorporated in any of the sensor configurations described hereinafter, with specific configurations suitable for incorporating the multiple enzymes being described in further detail hereinbelow.

When a single working electrode is present in an analyte sensor, three-electrode detection motifs may comprise a working electrode, a counter electrode, and a reference electrode. Related two-electrode detection motifs may comprise a working electrode and a second electrode, in which the second electrode functions as both a counter electrode and a reference electrode (i.e., a counter/reference electrode). In both two-electrode and three-electrode detection motifs, one or more active areas of the analyte sensor may be in contact with the working electrode. The one or more active areas may comprise multiple enzymes according to the embodiments of the present disclosure, with the multiple enzymes being present in a single active area and/or in multiple active areas. In some embodiments, the various electrodes may be at least partially stacked (layered) upon one another, as described in further detail hereinafter. In some or other embodiments, the various electrodes may be laterally spaced apart from one another upon the sensor tail. Similarly, the associated active areas upon each electrode may be stacked vertically upon top of one another or be laterally spaced apart. In either case, the various electrodes may be electrically isolated from one another by a dielectric material or similar insulator.

Figure 2A:
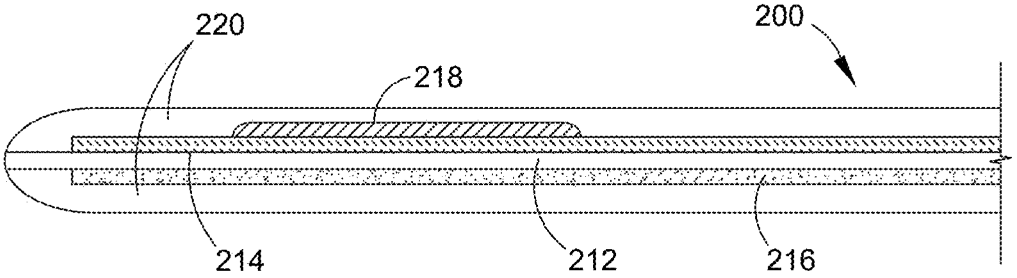
FIG. 2A shows a diagram of an illustrative two-electrode analyte sensor configuration having a single working electrode, which is compatible for use in some embodiments of the disclosure herein.

FIG. 2A shows a diagram of an illustrative two-electrode analyte sensor configuration having a single working electrode, which is compatible for use in some embodiments of the disclosure herein. As shown, analyte sensor 200 comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). Active area 218 is disposed as at least one layer upon at least a portion of working electrode 214. In various embodiments, active area 218 may comprise multiple spots or a single spot configured for detection of one or more analytes of interest. Collectively, multiple enzymes may be present in active area 218 (i.e., in a single spot or in multiple spots).

Referring still to FIG. 2A, membrane 220 overcoats at least active area 218 and may optionally overcoat some or all of working electrode 214 and/or counter/reference electrode 216, or the entirety of analyte sensor 200, according to some embodiments. One or both faces of analyte sensor 200 may be overcoated with membrane 220. Membrane 220 may comprise one or more polymeric membrane materials having capabilities of limiting analyte flux to active area 218. Depending on the identity of the analyte(s), the composition of membrane 220 may vary, as described further herein. Analyte sensor 200 may be operable for assaying the one or more analytes by any of coulometric, amperometric, voltammetric, or potentiometric electrochemical detection techniques.

Figure 2B:
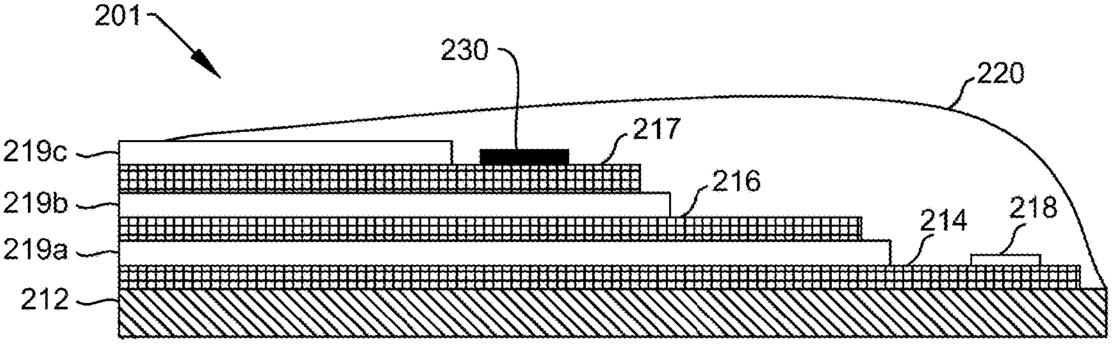
FIGS. 2B and 2C show diagrams of illustrative three-electrode analyte sensor configurations having a single working electrode, which are compatible for use in some embodiments of the disclosure herein.
Figure 2C:
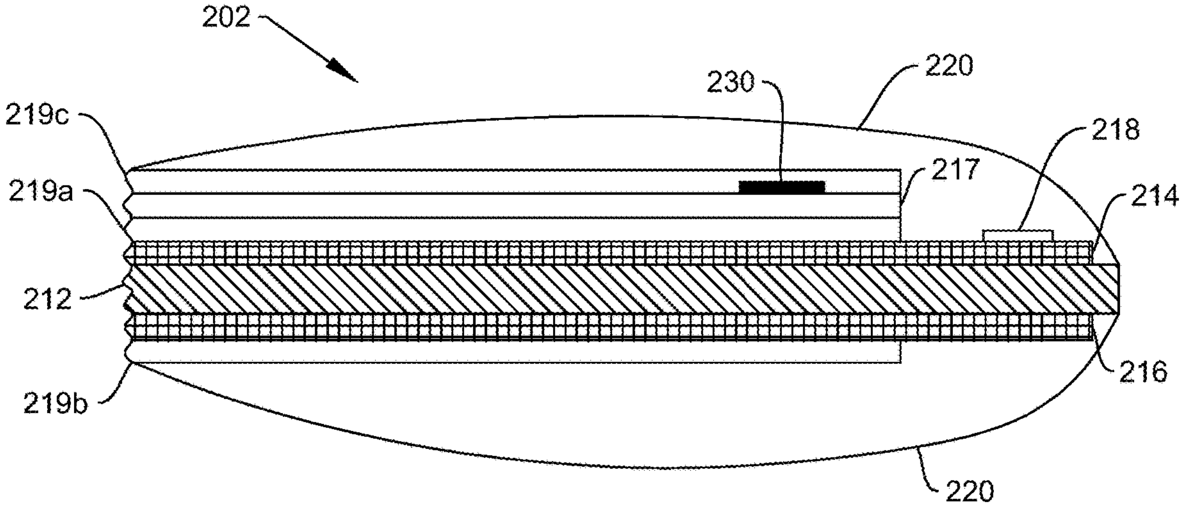

FIGS. 2B and 2C show diagrams of illustrative three-electrode analyte sensor configurations having a single working electrode, which are compatible for use in some embodiments of the disclosure herein. Three-electrode analyte sensor configurations employing a single working electrode may be similar to that shown for analyte sensor 200 in FIG. 2A, except for the inclusion of additional electrode 217 in analyte sensors 201 and 202 (FIGS. 2B and 2C). With additional electrode 217, counter/reference electrode 216 may then function as either a counter electrode or a reference electrode, and additional electrode 217 fulfills the other electrode function not otherwise accounted for. Working electrode 214 continues to fulfill its original function. Additional electrode 217 may be disposed upon either working electrode 214 or electrode 216, with a separating layer of dielectric material in between. For example, as depicted in FIG. 2B, dielectric layers 219*a*, 219*b* and 219*c* separate electrodes 214, 216 and 217 from one another and provide electrical isolation. Alternately, at least one of electrodes 214, 216 and 217 may be located upon opposite faces of substrate 212, as shown in FIG. 2C. Thus, in some embodiments, electrode 214 (working electrode) and electrode 216 (counter electrode) may be located upon opposite faces of substrate 212, with electrode 217 (reference electrode) being located upon one of electrodes 214 or 216 and spaced apart therefrom with a dielectric material. Reference material layer 230 (e.g., Ag/AgCl) may be present upon electrode 217, with the location of reference material layer 230 not being limited to that depicted in FIGS. 2B and 2C. As with sensor 200 shown in FIG. 2A, active area 218 in analyte sensors 201 and 202 may comprise multiple spots or a single spot configured for detection of one or more analytes of interest. Collectively, multiple enzymes may be present in active area 218 of analyte sensors 201 and 202. Additionally, analyte sensors 201 and 202 may be operable for assaying the one or more analytes by any of coulometric, amperometric, voltammetric, or potentiometric electrochemical detection techniques.

Like analyte sensor 200, membrane 220 may also overcoat active area 218, as well as other sensor components, in analyte sensors 201 and 202. Additional electrode 217 may be overcoated with membrane 220 in some embodiments. Although FIGS. 2B and 2C have depicted all of electrodes 214, 216 and 217 as being overcoated with membrane 220, it is to be recognized that only working electrode 214 may be overcoated in some embodiments. Moreover, the thickness of membrane 220 at each of electrodes 214, 216 and 217 may be the same or different. As in two-electrode analyte sensor configurations (FIG. 2A), one or both faces of analyte sensors 201 and 202 may be overcoated with membrane 220 in the sensor configurations of FIGS. 2B and 2C, or the entirety of analyte sensors 201 and 202 may be overcoated. Accordingly, the three-electrode sensor configurations shown in FIGS. 2B and 2C should be understood as being non-limiting of the embodiments disclosed herein, with alternative electrode and/or layer configurations remaining within the scope of the present disclosure.

Analyte sensor configurations having multiple working electrodes will now be described in further detail. Although the following description is primarily directed to analyte sensor configurations having two working electrodes, it is to be appreciated that more than two working electrodes may be successfully incorporated through an extension of the disclosure herein. Additional working electrodes may allow additional active area(s) and corresponding sensing capabilities to be imparted to analyte sensors having such features.

Figure 3:
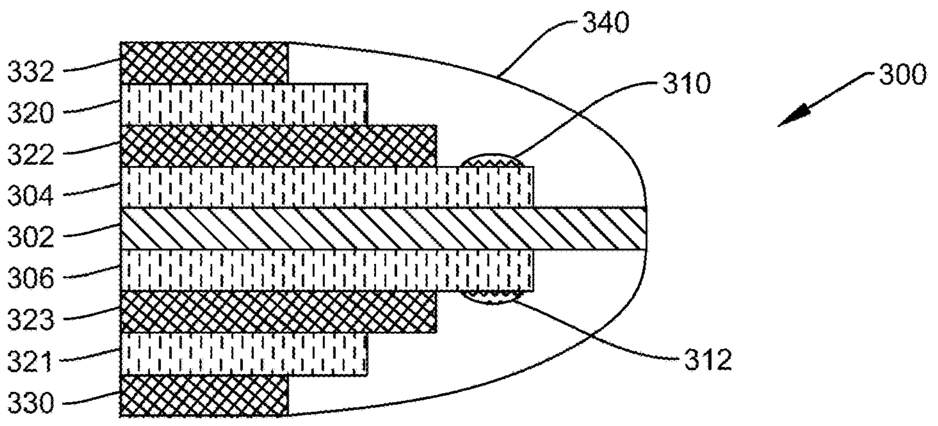
FIG. 3 shows a diagram of an illustrative analyte sensor configuration having two working electrodes, a reference electrode and a counter electrode, which is compatible for use in some embodiments of the disclosure herein.

FIG. 3 shows a diagram of an illustrative analyte sensor configuration having two working electrodes, a reference electrode and a counter electrode, which is compatible for use in some embodiments of the disclosure herein. As shown in FIG. 3, analyte sensor 300 includes working electrodes 304 and 306 disposed upon opposite faces of substrate 302. Active area 310 is disposed upon the surface of working electrode 304, and active area 312 is disposed upon the surface of working electrode 306. Collectively, multiple enzymes may be present in active areas 310 and 312, with each active area 310,312 containing one or more enzymes. For example, a glucose-responsive enzyme may be present in active area 310 and a lactate-responsive enzyme may be present in active area 312 in particular embodiments. Counter electrode 320 is electrically isolated from working electrode 304 by dielectric layer 322, and reference electrode 321 is electrically isolated from working electrode 306 by dielectric layer 323. Outer dielectric layers 330 and 332 are positioned upon reference electrode 321 and counter electrode 320, respectively. Membrane 340 may overcoat at least active areas 310 and 312, according to various embodiments. Other components of analyte sensor 300 may be overcoated with membrane 340 as well, and as above, one or both faces of analyte sensor 300, or a portion thereof, may be overcoated with membrane 340. Like analyte sensors 200, 201 and 202, analyte sensor 300 may be operable for assaying one or more analytes by any of coulometric, amperometric, voltammetric, or potentiometric electrochemical detection techniques.

Alternative analyte sensor configurations having multiple working electrodes and differing from that shown in FIG. 3 may feature a counter/reference electrode instead of separate counter and reference electrodes 320,321, and/or feature layer and/or membrane arrangements varying from those expressly depicted. For example, the positioning of counter electrode 320 and reference electrode 321 may be reversed from that depicted in FIG. 3. In addition, working electrodes 304 and 306 need not necessarily reside upon opposing faces of substrate 302 in the manner shown in FIG. 3.

Figure 6A:
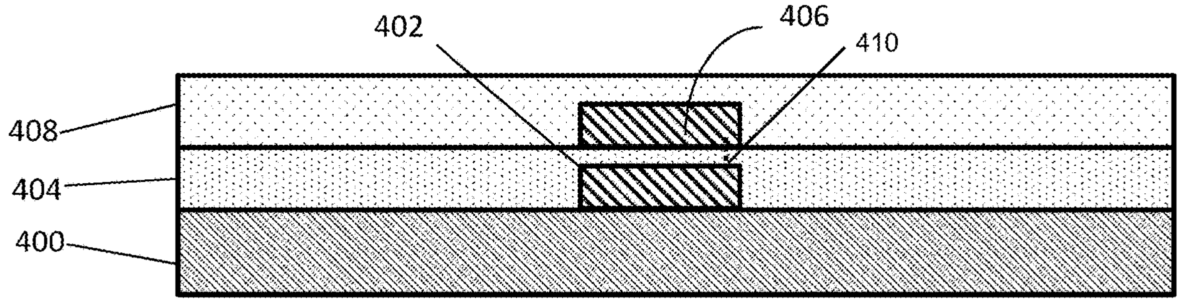
FIGS. 6A and 6B show diagrams of illustrative working electrodes in which a first active area is disposed directly upon a surface of the working electrode and a second active area is separated from the working electrode by a membrane, and which is compatible for use in some embodiments of the disclosure herein.
Figure 6B:
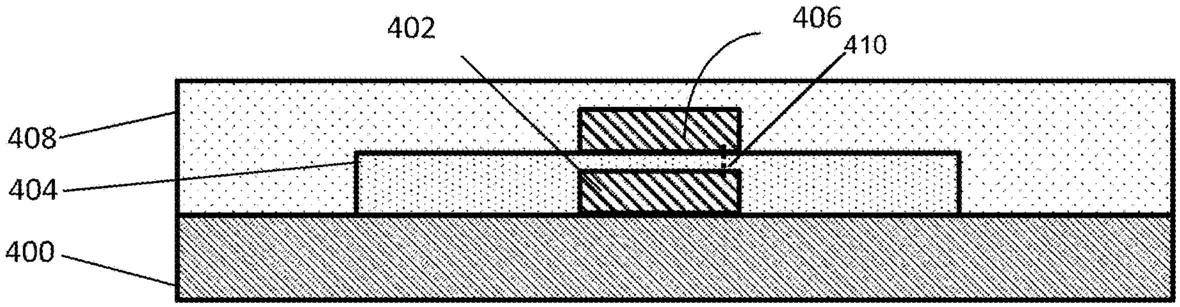

Analyte sensor configurations featuring a working electrode having an active area remote therefrom are shown in FIGS. 6A and 6B and discussed further below.

According to various embodiments of the present disclosure, an electron transfer agent may be present in one or more of the active areas of any of the analyte sensors or analyte sensor configurations disclosed herein. Suitable electron transfer agents may facilitate conveyance of electrons to the working electrode when an analyte (enzyme substrate) undergoes an oxidation-reduction reaction. Choice of the electron transfer agent within each active area may dictate the oxidation-reduction potential observed for each. When multiple active areas are present, the electron transfer agent within each active area may be the same or different.

Suitable electron transfer agents may include electroreducible and electrooxidizable ions, complexes or molecules (e.g., quinones) having oxidation-reduction potentials that are a few hundred millivolts above or below the oxidation-reduction potential of the standard calomel electrode (SCE).

According to some embodiments, suitable electron transfer agents may include low-potential osmium complexes, such as those described in U.S. Pat. Nos. 6,134,461 and 6,605,200, which are incorporated herein by reference in their entirety. Additional examples include those described in U.S. Pat. Nos. 6,736,957, 7,501,053 and 7,754,093, the disclosures of each of which are incorporated herein by reference in their entirety. Other suitable electron transfer agents may comprise metal compounds or complexes of ruthenium, osmium, iron (e.g., polyvinylferrocene or hexacyanoferrate), or cobalt, including metallocene compounds thereof, for example. Suitable examples of electron transfer mediators and polymer-bound electron transfer mediators may include those described in U.S. Pat. Nos. 8,444,834, 8,268,143 and 6,605,201, the disclosures of which are incorporated herein by reference in their entirety. Suitable ligands for the metal complexes may also include, for example, bidentate or higher denticity ligands such as, for example, bipyridine, biimidazole, phenanthroline, or pyridyl (imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in a metal complex to achieve a full coordination sphere.

According to various embodiments of the present disclosure, a polymer may be present in each active area of any of the analyte sensors or analyte sensor configurations disclosed herein. Suitable polymers for inclusion in the active areas may include, but are not limited to, polyvinylpyridines (e.g., poly(4-vinylpyridine)), polyvinylimidazoles (e.g., poly(1-vinylimidazole)), or any copolymer thereof. Illustrative copolymers that may be suitable for inclusion in the active areas include those containing monomer units such as styrene, acrylamide, methacrylamide, or acrylonitrile, for example. When multiple active areas are present, the polymer within each active area may be the same or different.

According to various embodiments of the present disclosure, the electron transfer agent may be covalently bonded to the polymer in each active area. The manner of covalent bonding is not considered to be particularly limited. Covalent bonding of the electron transfer agent to the polymer may take place by polymerizing a monomer unit bearing a covalently bound electron transfer agent, or the electron transfer agent may be reacted with the polymer separately after the polymer has already been synthesized. According to some embodiments, a bifunctional spacer may covalently bond the electron transfer agent to the polymer within the active area, with a first functional group being reactive with the polymer (e.g., a functional group capable of quaternizing a pyridine nitrogen atom or an imidazole nitrogen atom) and a second functional group being reactive with the electron transfer agent (e.g., a functional group that is reactive with a ligand coordinating a metal ion).

Similarly, according to some or other various embodiments of the present disclosure, the enzyme within one or more of the active areas may be covalently bonded to the polymer. When multiple enzymes are present in a single active area, all of the multiple enzymes may be covalently bonded to the polymer in some embodiments, and in other embodiments, only a portion of the multiple enzymes may be covalently bonded to the polymer. For example, a first enzyme may be covalently bonded to the polymer and a second enzyme may be non-covalently associated with the polymer. According to more specific embodiments, covalent bonding of the enzyme to the polymer may take place via a crosslinker introduced with a suitable crosslinking agent. Suitable crosslinking agents for reaction with free amino groups in the enzyme (e.g., with the free amine in lysine) may include crosslinking agents such as, for example, polyethylene glycol diglycidylether (PEGDGE) or other polyepoxides, cyanuric chloride, N-hydroxysuccinimide, imidoesters, epichlorohydrin, or derivatized variants thereof. Suitable crosslinking agents for reaction with free carboxylic acid groups in the enzyme may include, for example, carbodiimides. The crosslinking is generally intermolecular, but can be intramolecular in some embodiments.

The electron transfer agent and/or the enzyme may be associated with the polymer in the active area through means other than covalent bonding as well. In some embodiments, the electron transfer agent and/or the enzyme may be ionically or coordinatively associated with the polymer. For example, a charged polymer may be ionically associated with an oppositely charged electron transfer agent or enzyme. In still other embodiments, the electron transfer agent and/or the enzyme may be physically entrained within the polymer without being bonded thereto.

Various configurations suitable for arranging multiple enzymes in analyte sensors of the present disclosure will now be described in further detail. The multiple enzymes may be deposited within one or more active areas of the sensors. The active areas may range in size from about 0.01 $mm^2$ to about 1 $mm^2$, although larger or smaller active areas are also contemplated herein.

In some embodiments, multiple enzymes may be arranged within separate active areas upon a single working electrode. When the multiple enzymes are arranged in this manner, each active area may facilitate detection of separate analytes, as described hereinafter. At least one of the active areas may produce a signal independently of the other active areas.

According to some embodiments, analyte sensors of the present disclosure having multiple active areas upon a single working electrode may comprise: a sensor tail comprising at least a working electrode, and at least two active areas disposed upon a surface of the working electrode. Each active area comprises an analyte-responsive enzyme and a polymer, with the analyte-responsive enzyme in each active area being different. Each active area has an oxidation-reduction potential, and the oxidation-reduction potential of a first active area is sufficiently separated from the oxidation-reduction potential of a second active area to allow production of a signal from the first active area independent of a signal from the second active area. In more specific embodiments, such analyte sensors may comprise a single working electrode having the at least two active areas. An electron-transfer agent may be incorporated within each active area to promote electron transfer.

Alternative sensor configurations may comprise a single active area containing both the first analyte-responsive enzyme and the second analyte-responsive enzyme, along with an electron transfer agent. Each enzyme may be covalently bonded to separate portions of the polymer in the single active area. Provided that the sensing chemistries for promoting electron transfer for each analyte are not overly diluted in the single active area, the single active area may facilitate analyte detection in a manner similar to that described below for separate active areas. Such sensor configurations may be particularly feasible when the analytes to be assayed with the first and second analyte-responsive enzymes have comparable membrane permeability values.

In more specific embodiments, the sensor tail may be configured for insertion into a tissue. Suitable tissues are not considered to be particularly limited and are addressed in more detail above. Similarly, considerations for deploying a sensor tail at a particular position within a tissue are addressed above.

In more specific embodiments, the oxidation-reduction potential associated with the first active area may be separated from the oxidation-reduction potential of the second active area by at least about 100 mV, or by at least about 150 mV, or by at least about 200 mV. The upper limit of the separation between the oxidation-reduction potentials is dictated by the working electrochemical window in vivo. By having the oxidation-reduction potentials of the active areas sufficiently separated in magnitude from one another, an electrochemical reaction may take place within the first active area without substantially inducing an electrochemical reaction within the second active area. Thus, a signal from the first active area may be independently produced at or above its corresponding oxidation-reduction potential. At or above the oxidation-reduction potential of the second active area, in contrast, electrochemical reactions may occur within both active areas. As such, the resulting signal at or above the oxidation-reduction potential of the second active area may include a signal contribution from both the first active area and the second active area, and the signal is a composite signal. The signal contribution from the second active area at or above its oxidation-reduction potential may then be determined by subtracting from the composite signal the signal obtained solely from the first active area at or above its corresponding oxidation-reduction potential. Similar considerations apply to analyzing the signal contributions from a single active area containing two different enzymes that produce signals at different oxidation-reduction potentials.

In more specific embodiments, the first and second active areas may contain different electron transfer agents when the active areas are located upon the same working electrode, so as to afford oxidation-reduction potentials that are sufficiently separated in magnitude. More specifically, the first active area may comprise a first electron transfer agent and the second active area may comprise a second electron transfer agent, with the first and second electron transfer agents being different. The metal center and/or the ligands present in a given electron transfer agent may be varied to provide sufficient separation of the oxidation-reduction potentials of the first and second active areas, according to various embodiments of the present disclosure. According to still more specific embodiments, the first electron transfer agent may be covalently bonded to the polymer in the first active area, and the second electron transfer agent may be covalently bonded to the polymer in the second active area. The manner of covalent bonding for the first electron transfer agent and the second electron transfer agent may be the same or different. Similar considerations apply to choosing electron transfer agents suitable for use in conjunction with a first analyte-responsive enzyme and a second analyte-responsive enzyme contained within a single active area, in accordance with the disclosure above.

In more specific embodiments of the present disclosure, the analyte-responsive enzyme in each active area may be covalently bonded (or otherwise immobilized) to the polymer within each active area. In still more specific embodiments, the analyte-responsive enzyme and the electron transfer agent in each active area may be covalently bonded to the polymer within each active area. When contained in a single active area, the first analyte-responsive enzyme and a first electron transfer agent may be covalently bonded to a first portion of polymer, and the second analyte-responsive enzyme and a second electron transfer agent may be covalently bonded to a second portion of polymer. The polymer in the first portion and the second portion may be the same or different.

Ideally, first and second active areas located upon a single working electrode may be configured to attain a steady state current rapidly upon operating the analyte sensor at a given potential. Rapid attainment of a steady state current may be promoted by choosing an electron transfer agent for each active area that changes its oxidation state quickly upon being exposed to a potential at or above its oxidation-reduction potential. Making the active areas as thin as possible may also facilitate rapid attainment of a steady state current. For example, suitable thicknesses for the first and second active areas may range from about 0.1 microns to about 10 microns. In some or other embodiments, combining a conductive material such as, for example, carbon nanotubes, graphene, or metal nanoparticles within one or more of the active areas may promote rapid attainment of a steady state current. Suitable amounts of conductive particles may range from about 0.1% to about 50% by weight of the active area, or from about 1% to about 50% by weight, or from about 0.1% to about 10% by weight, or from about 1% to about 10% by weight. Stabilizers may also be employed to promote response stability.

It is also to be appreciated that the sensitivity (output current) of the analyte sensors toward each analyte may be varied by changing the coverage (area or size) of the active areas, the areal ratio of the active areas with respect to one another, the identity and thickness of the mass transport limiting membrane overcoating the active areas, and any combination thereof. Variation of these parameters may be conducted readily by one having ordinary skill in the art once granted the benefit of the disclosure herein.

Although the foregoing description is primarily directed to analyte sensors configured for detecting two different analytes, it is to be appreciated that the concepts above may be extended for detecting more than two analytes using a corresponding number of active areas located upon a single working electrode. Specifically, analyte sensors employing more than two active areas and a corresponding number of different enzymes (and electron transfer agents) therein may be employed to detect a like number of different analytes in further embodiments of the present disclosure. Provided that the oxidation-reduction potential of each active area is sufficiently separated from that of other active areas, the signal contribution from each active area may be analyzed in a manner related to that described above to provide the concentration of each analyte.

In more particular embodiments, the first active area may comprise a glucose-responsive enzyme, such as glucose oxidase, and the second active area may comprise a lactate-responsive enzyme, such as lactate oxidase, in addition to the suitable electron transfer agents and polymers discussed in more detail above. According to particular embodiments, analyte sensors suitable for detecting glucose and lactate may comprise a working electrode having a first active area and a second active area disposed thereon, and a mass transport limiting membrane overcoating the first and second active areas upon the working electrode, in which the second active area comprises a polymer, an albumin, and a lactate-responsive enzyme (e.g., lactate oxidase) covalently bonded to the polymer and the first active area comprises a glucose-responsive enzyme (e.g., glucose oxidase) covalently bonded to a polymer. First and second electron transfer agents differing from one another may be present in each active area. In more specific embodiments, the mass transport limiting membrane may comprise at least a crosslinked polyvinylpyridine homopolymer or copolymer. The composition of the mass transport limiting membrane may be the same or different where the mass transport limiting membrane overcoats each active area. In particular embodiments, the mass transport limiting membrane overcoating the first active area may be single-component (contain a single membrane polymer) and the mass transport limiting membrane overcoating the second active area may be multi-component (contain two or more different membrane polymers, one of which is a polyvinylpyridine homopolymer or copolymer), either as a bilayer or homogeneous admixture.

Similarly, it is also to be appreciated that some analyte sensors of the present disclosure having two or more active areas located upon a given working electrode may comprise two or more analyte-responsive enzymes in at least one of the active areas. According to more specific embodiments, the two or more analyte-responsive enzymes in a given active area may interact in concert to generate a signal proportional to the concentration of a single analyte. Thus, analyte-responsive enzymes need not necessarily be present in a 1:1 ratio with a given selection of analytes. Analyte sensors containing in concert interacting enzymes are described in further detail hereinbelow.

Accordingly, multi-analyte detection methods employing analyte sensors featuring multiple enzymes arranged upon a single working electrode are also described herein. In various embodiments, such methods may comprise: exposing an analyte sensor to a fluid comprising at least one analyte. The analyte sensor comprises a sensor tail comprising at least a working electrode, particularly a single working electrode, and at least two active areas disposed upon a surface of the working electrode. Each active area comprises an analyte-responsive enzyme and a polymer, and the analyte-responsive enzyme in each active area is different. Each active area has an oxidation-reduction potential, and the oxidation-reduction potential of a first active area is sufficiently separated from the oxidation-reduction potential of a second active area to allow production of a signal from the first active area independent of production of a signal from the second active area. The methods additionally comprise: obtaining a first signal at or above the oxidation-reduction potential of the first active area, such that the first signal is proportional to a concentration of a first analyte; obtaining a second signal at or above the oxidation-reduction potential of the second active area, such that the second signal is a composite signal comprising a signal contribution from the first active area and a signal contribution from the second active area; and subtracting the first signal from the second signal to obtain a difference signal, the difference signal being proportional to a concentration of the second analyte.

In more specific embodiments, the oxidation-reduction potential associated with the first active area may be separated from the oxidation-reduction potential of the second active area by at least about 100 mV, or by at least about 150 mV, or by at least about 200 mV in order to provide sufficient separation for independent production of a signal from the first active area.

In some or other more specific embodiments, the fluid is a biological fluid and the analyte sensor is exposed to the biological fluid in vivo within an individual. Suitable biological fluids for analysis with analyte sensors having at least two different active areas located upon a given working electrode may include any of the biological fluids discussed in more detail above.

In some embodiments, the signals associated with each active area may be correlated to a corresponding analyte concentration by consulting a lookup table or calibration curve for each analyte. A lookup table for each analyte may be populated by assaying multiple samples having known analyte concentrations and recording the sensor response at each concentration for each analyte. Similarly, a calibration curve for each analyte may be determined by plotting the analyte sensor response for each analyte as a function of the concentration. According to some embodiments, the calibration curve for analyte sensors of the present disclosure may be linear.

A processor may determine which sensor response value in a lookup table is closest to that measured for a sample having an unknown analyte concentration and then report the analyte concentration accordingly. In some or other embodiments, if the sensor response value for a sample having an unknown analyte concentration is between the recorded values in the lookup table, the processor may interpolate between two lookup table values to estimate the analyte concentration. Interpolation may assume a linear concentration variation between the two values reported in the lookup table. Interpolation may be employed when the sensor response differs a sufficient amount from a given value in the lookup table, such as variation of about 10% or greater.

Likewise, according to some or other various embodiments, a processor may input the sensor response value for a sample having an unknown analyte concentration into a corresponding calibration curve. The sensor may then report the analyte concentration accordingly.

Embodiments of analyte sensors having two different active areas disposed upon a given working electrode may employ sensor configurations related to those depicted in FIGS. 2A-2C and described above. It is to be appreciated, however, that suitable analyte sensors may also feature multiple working electrodes, such as the sensor configuration shown in FIG. 3, with at least one of the working electrodes having at least two active areas that differ from one another. It is also to be appreciated that other analyte sensor configurations having two or more different active areas disposed upon the surface of a given working electrode also reside within the scope of the present disclosure. For example, the location, orientation or functionality of the working electrode and the counter and/or reference electrodes may differ from that shown in the figures herein.

Figure 4:
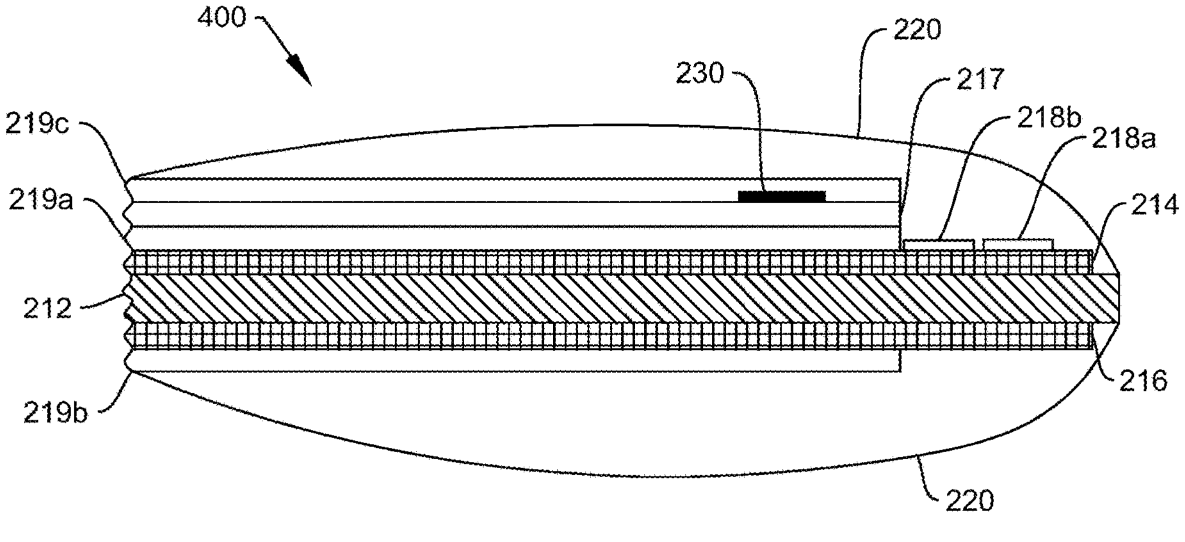
FIG. 4 shows an illustrative analyte sensor configuration compatible for use in some embodiments of the disclosure herein, in which two different active areas are disposed upon the surface of a single working electrode.

FIG. 4 shows an illustrative analyte sensor configuration compatible for use in some embodiments of the disclosure herein, in which two different active areas are disposed upon the surface of a single working electrode. The analyte sensor configuration of FIG. 4 bears most similarity to that of FIG. 2C and may be better understood by reference thereto. Where appropriate, common reference characters from FIG. 2C are used in FIG. 4 in the interest of clarity, and features having a common structure and/or function are not described again in further detail in the interest of brevity. Again, it is to be appreciated that other analyte sensor configurations may similarly incorporate the features described below for FIG. 4.

Referring to FIG. 4, analyte sensor 400 includes active areas 218*a* and 218*b* upon the surface of working electrode 214. Active area 218*a* includes a first electron transfer agent and a first analyte-responsive enzyme that may be covalently bonded to a polymer comprising active area 218*a*. Active area 218*b* similarly includes a second electron transfer agent and a second analyte-responsive enzyme that may be covalently bonded to a polymer comprising active area 218*b*. The first electron transfer agent and the second electron transfer agent may differ in composition so as to provide separation of the oxidation-reduction potentials of first active area 218*a* and second active area 218*b*. In particular embodiments, active area 218*b* may comprise a lactate-responsive enzyme, such as lactate oxidase, and active area 218*a* may comprise a glucose-responsive enzyme, such as glucose oxidase.

The oxidation-reduction potentials of first active area 218*a* and second active area 218*b* may be sufficiently separated from one another to allow production of a signal from first active area 218*a* independent of signal production from second active area 218*b*. As such, analyte sensor 400 may be operated at a first potential at which an oxidation-reduction reaction occurs within first active area 218*a* but not within second active area 218*b*. Thus, a first analyte (e.g., glucose) may be selectively detected at or above the oxidation-reduction potential of first active area 218*a*, provided that the applied potential is not high enough to promote an oxidation-reduction reaction with second active area 218*b*. A concentration of the first analyte may be determined from the sensor response of first active area 218*a* by referring to a lookup table or calibration curve.

At or above the oxidation-reduction potential of second active area 218*b*, separate oxidation-reduction reactions may take place simultaneously or near simultaneously within both first active area 218*a* and second active area 218*b*. As a result, the signal produced at or above the oxidation-reduction potential of second active area 218*b* may comprise a composite signal having signal contributions from both first active area 218*a* and second active area 218*b*. To determine the concentration of the second analyte (e.g., lactate) from the composite signal, the signal from first active area 218*a* at or above its corresponding oxidation-reduction potential may be subtracted from the composite signal to provide a difference signal associated with second active area 218*b* alone. Once the difference signal has been determined, the concentration of a second analyte may be determined by reference to a lookup table or calibration curve.

As mentioned previously, similar considerations also apply to separating a first signal and a second signal from a single active area containing two different analyte-responsive enzymes in order to determine the concentrations of first and second analytes that differ from one another.

In some or other embodiments of the present disclosure, multiple enzymes may be present in a single active area. Unlike sensor configurations in which multiple enzymes function independently to detect different analytes, particularly spaced apart in separate active areas upon the surface of a working electrode, multiple enzymes arranged in a single active area may function in concert to facilitate detection of a single analyte, according to some embodiments of the present disclosure, particularly in the presence of a stabilizer. As used herein, the term "in concert" and grammatical variants thereof refer to a coupled enzyme reaction, in which the product of a first enzymatic reaction becomes the substrate for a second enzymatic reaction, and the second enzymatic reaction serves as the basis for measuring the concentration of the substrate (analyte) reacted during the first enzymatic reaction. It may be desirable to utilize two enzymes acting in concert with one another to detect a given analyte of interest when a single enzyme is unable to facilitate detection. Situations in which a single enzyme may be ineffective for promoting analyte detection include, for example, those in which the enzyme is inhibited by one or more products of the enzymatic reaction or is unable to cycle between an oxidized state and reduced state when disposed within an analyte sensor.

As also disclosed herein, multiple enzymes disposed in separate active areas may likewise interact in concert to promote detection of a single analyte. When the multiple enzymes are located in separate active areas, one of the active areas may be isolated from the working electrode so that electron transfer to and from the working electrode takes place from only one of the active areas.

In more specific embodiments, analyte sensors featuring at least two enzymes interacting in concert with one another may comprise: a sensor tail comprising at least a working electrode; and at least one active area disposed upon a surface of the working electrode. The at least one active area comprises a first enzyme, a second enzyme, and a polymer. The first and second enzymes are capable of interacting in concert, such that the first enzyme is capable of converting an analyte into a first product, and the second enzyme is capable of converting the first product into a second product to generate a signal at the working electrode. The second enzyme is unreactive with the analyte. At least the second enzyme is covalently bonded to the polymer in the at least one active area. Analysis of a signal (e.g., the current measured at a fixed input voltage) resulting from the reaction of the first product into the second product may provide a basis for detecting an analyte and measuring its concentration, as explained in further detail hereinafter.

More specifically, the active area may comprise an electron transfer agent, such as those described above, and only the second enzyme is capable of exchanging electrons with the electron transfer agent, in which case the first enzyme may indirectly convey electrons to the second enzyme, as explained hereinafter. Accordingly, more specific embodiments of the present disclosure may feature a first enzyme that is not covalently bonded to the polymer (so that it is less likely to exchange electrons with the electron transfer agent) and a second enzyme that is covalently bonded to the polymer (to promote exchange of electrons with the electron transfer agent). The electron transfer agent may be covalently bonded to the polymer in the active area in either case. Coordinative bonding is also included within the scope of covalent bonding in accordance with the disclosure herein.

A stabilizer may be present in the active area, according to some embodiments. Particularly suitable stabilizers for analyte sensors containing in concert interacting enzymes include catalase and albumin, for example.

According to some embodiments, the sensor tail may be configured for insertion into a tissue of interest. As such, according to some embodiments, analyte sensors containing enzymes capable of interacting in concert with one another in a given active area may be adapted to analyze the concentration of an analyte in a biological fluid in vivo. The identity of the biological fluid is again not particularly limited.

As above, sensor configurations incorporating two enzymes that are capable of interacting in concert may include those in which the at least one active area comprises an electron transfer agent that is covalently bonded to the polymer. Again, coordinative bonding is also included within the scope of covalent bonding in accordance with the disclosure herein. In such embodiments, at least the second enzyme may also be covalently bonded to the polymer. In some embodiments, the first enzyme is not covalently bonded to the polymer. In other embodiments, both the first enzyme and the second enzyme may be covalently bonded to the polymer in the at least one active area. Covalent bonding of the first enzyme to the polymer may be desirable, for example, to lessen the likelihood of leaching the first enzyme from the at least one active area.

Analyte sensor configurations suitable for incorporating two enzymes interacting in concert with one another in one or more active areas upon a working electrode may be similar to those shown in FIGS. 2A-2C and described in more detail above. Enzymes capable of interacting in concert with one another (i.e., concerted enzymes or concerted enzyme pairs) may also be incorporated in analyte sensor configurations having multiple working electrodes (FIG. 3) or having multiple active areas arranged on a given working electrode (FIG. 4). Any of the analyte sensors disclosed herein with a concerted enzyme pair located directly upon the surface of a working electrode may employ any of the foregoing analyte sensor configurations. Analyte sensor configurations having two or more enzymes interacting in concert with one another in multiple active areas, in which one of the active areas is remote from the working electrode, are discussed further below in reference to FIGS. 6A and 6B.

In more specific configurations of analyte sensors containing concerted enzymes both disposed directly on a working electrode, the first enzyme may be alcohol oxidase (AOX) and the second enzyme may be xanthine oxidase (XOX). With this pair of enzymes, the analyte sensor may be functional to detect an alcohol, particularly ethanol, according to one or more embodiments. Cooperativity between alcohol oxidase and xanthine oxidase for detecting ethanol and other alcohols with both enzymes disposed upon a working electrode is explained in further detail hereinafter (see FIG. 5A). In more specific embodiments of the present disclosure, the xanthine oxidase may be covalently bonded to the polymer in the active area, and the alcohol oxidase is not covalently bonded to the polymer. In still more specific embodiments, both xanthine oxidase and an electron transfer agent may be covalently bonded to the polymer, and the alcohol oxidase is not covalently bonded to the polymer. Catalase may be present as a stabilizer with this pair of enzymes.

Another pair of concerted enzymes that may be suitable for use in the disclosure herein with both enzymes disposed directly on the surface of a working electrode is β-hydroxybutyrate dehydrogenase and diaphorase. This concerted enzyme pair may be used for ketone body detection, with β-hydroxybutyrate being a representative molecule indicative of the presence of ketones. In sensor configurations containing this pair of concerted enzymes, β-hydroxybutyrate dehydrogenase may convert β-hydroxybutyrate and oxidized nicotinamide adenine dinucleotide ($NAD^+$) into acetoacetate and reduced nicotinamide adenine dinucleotide (NADH). The NADH may then undergo oxidation under diaphorase mediation, with the electrons transferred during this process providing the basis for ketone detection at the working electrode. The concerted reaction between β-hydroxybutyrate and diaphorase (mediated by $NAD^+$ cofactor) for detecting ketones is shown in FIG. 5B. Albumin may be present as a stabilizer with this pair of concerted enzymes.

Figure 5A:
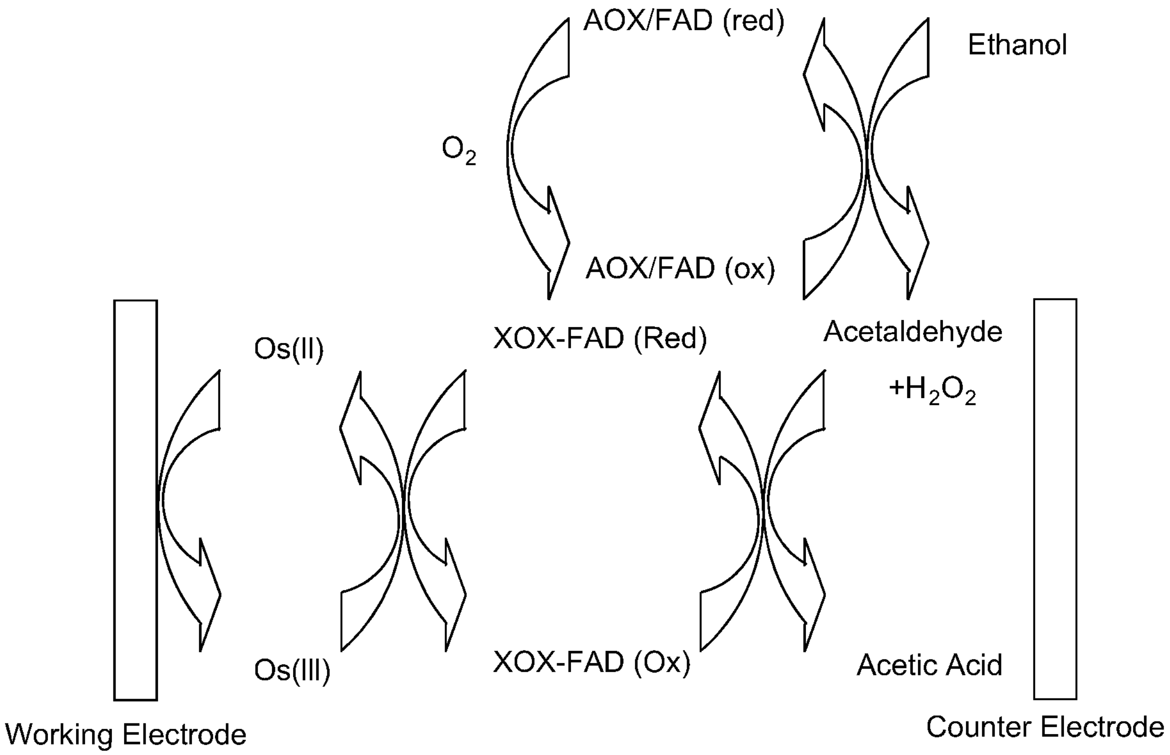
FIG. 5A shows the concerted enzymatic reaction cycle associated with ethanol detection using alcohol oxidase and xanthine oxidase located directly upon a working electrode, according to various embodiments of the present disclosure.
Figure 5B:
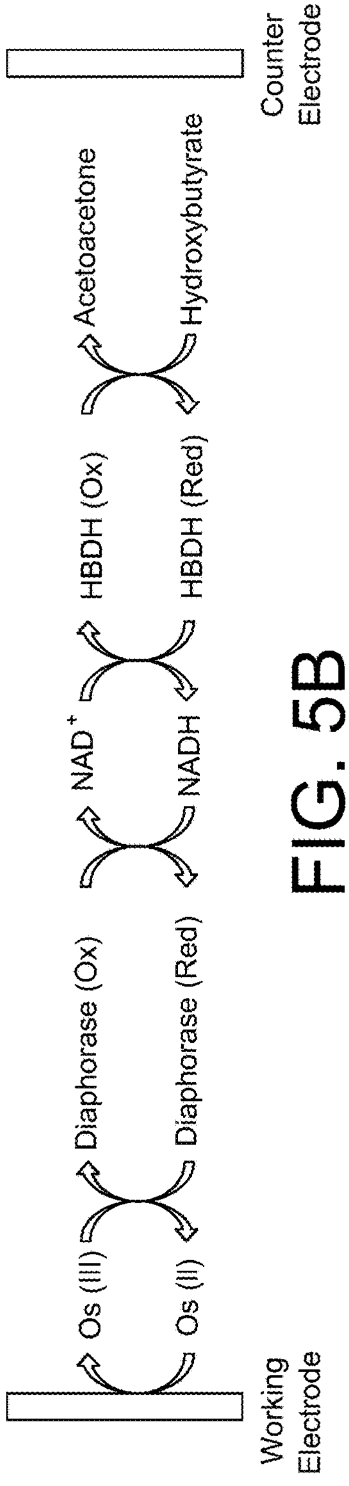
FIG. 5B shows the concerted enzymatic reaction cycle associated with ketone detection using β-hydroxybutyrate dehydrogenase, nicotinamide adenine dinucleotide, and diaphorase located directly upon a working electrode, according to various embodiments of the present disclosure.
Figure 5C:
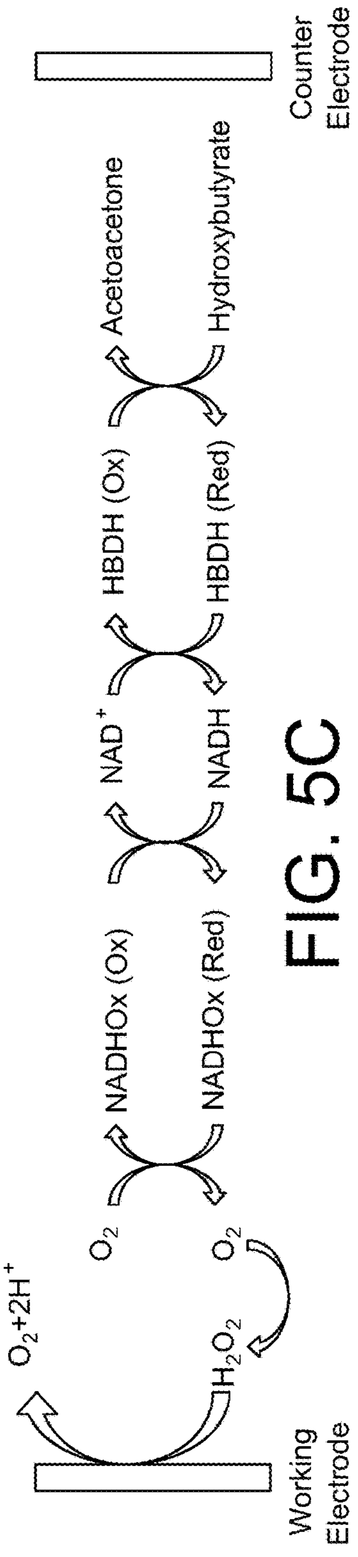
FIG. 5C shows the concerted enzymatic reaction cycle associated with ketone detection using β-hydroxybutyrate dehydrogenase, nicotinamide adenine dinucleotide, NADH oxidase, and superoxide dismutase located directly upon a working electrode, according to various embodiments of the present disclosure
Figure 5D:
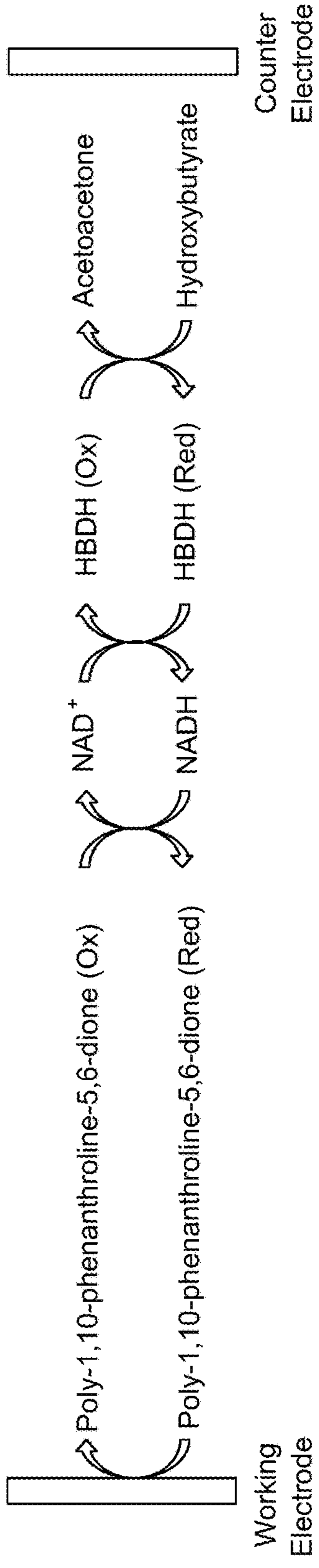
FIG. 5D shows the concerted enzymatic reaction cycle associated with ketone detection using β-hydroxybutyrate dehydrogenase, nicotinamide adenine dinucleotide, and poly-1,10-phenanthroline-5,6-dione located directly upon a working electrode, according to various embodiments of the present disclosure.

Still other alternative enzymatic detection chemistries for ketones are shown in FIGS. 5C and 5D. As shown in FIG. 5C, β-hydroxybutyrate dehydrogenase may convert β-hydroxybutyrate and $NAD^+$ into acetoacetate and NADH. Instead of electron transfer to the working electrode being completed by diaphorase (see FIG. 5B), the reduced form of NADH oxidase (NADHOx (Red)) undergoes a reaction to form the corresponding oxidized form (NADHOx (Ox)). NADHOx (Red) may then be reformed by a reaction with molecular oxygen to produce superoxide, which may undergo subsequent conversion to hydrogen peroxide under superoxide dismutase (SOD) mediation. The SOD may be covalently bonded to the polymer in the active area, according to various embodiments. The hydrogen peroxide may then undergo a reaction at the working electrode to provide a signal that may be correlated to the amount of ketones that are present. FIG. 5D shows another alternative enzymatic detection chemistry in which β-hydroxybutyrate dehydrogenase again may convert β-hydroxybutyrate and $NAD^+$ into acetoacetate and NADH. The detection cycle in this case is completed by oxidation of poly-1,10-phenanthroline-5,6-dione at the working electrode. Like other sensing chemistries disclosed herein, inclusion of an albumin in the active area may provide a surprising improvement in response stability.

Creatine amidohydrolase and sarcosine oxidase are another pair of concerted enzymes that may be suitable for use in the disclosure herein when both enzymes are disposed directly upon a working electrode. Creatine amidohydrolase generates sarcosine and urea from creatine. The sarosine oxidase, in turn, may catalyze the reaction of sarcosine to form glycine, formaldehyde, and hydrogen peroxide. Accordingly, detection of the hydrogen peroxide at the working electrode may serve as the basis for quantifying creatine and/or sarcosine.

The detection of ethanol and other alcohols using alcohol oxidase and xanthine oxidase via a concerted enzymatic reaction will now be described in further detail. Alcohol oxidase interacts with ethanol to form acetaldehyde and hydrogen peroxide. Other alcohols react to form aldehydes with a corresponding higher or lower carbon count. Advantageously, alcohol oxidase only catalyzes the forward conversion of ethanol into acetaldehyde (as opposed to performing the reaction reversibly, such as is the case for alcohol dehydrogenase), which may be favorable for use of this enzyme in an analyte sensor. Moreover, alcohol oxidase contains a strongly bound flavin co-factor, such that exogenous co-factors need not necessarily be combined with alcohol oxidase to render the enzyme active for promoting alcohol oxidation.

In principle, alcohol oxidase alone could be employed for ethanol detection in an analyte sensor by assaying either the acetaldehyde or hydrogen peroxide products produced in the enzymatic reaction. There are two issues with this approach, however. First, both acetaldehyde and hydrogen peroxide are inhibitory toward alcohol oxidase. Thus, if these compounds are not cleared from the sensor environment, the alcohol oxidase becomes inactive for promoting ethanol oxidation, thereby leaving the analyte sensor non-functional for assaying ethanol. Moreover, if acetaldehyde and hydrogen peroxide become sequestered or undergo quenching with other agents, there is no longer a species available for electrochemical detection. Second, alcohol oxidase does not freely exchange electrons with oxidation-reduction mediators, other than molecular oxygen. As such, electron transfer agents associated with a polymer in the active area of an analyte sensor, such as the osmium and other transition metal complexes discussed herein, are ineffective for cycling alcohol oxidase from an inactive reduced state into an oxidized state that is reactive with ethanol. Thus, although alcohol oxidase may be optionally covalently bonded to the polymer, there are no particular benefits to the electron transfer process in doing so. That is, covalent bonding of alcohol oxidase to the polymer does not aid in promoting electron transfer with the electron transfer agent.

The concerted combination of alcohol oxidase and xanthine oxidase directly upon a working electrode, particularly together in a given active area, may overcome at least some of the foregoing challenges associated with ethanol detection using an analyte sensor employing alcohol oxidase. Acetaldehyde and other aldehydes may serve as a substrate for xanthine oxidase, with the acetaldehyde being enzymatically converted to acetic acid. Thus, xanthine oxidase may clear acetaldehyde from the sensor environment, thereby precluding acetaldehyde-based inactivation of the alcohol oxidase. Catalase may be present in the active area to clear hydrogen peroxide (e.g., as a catalase-hydrogen peroxide complex), thereby precluding inactivation of the alcohol oxidase with this species. In addition, unlike alcohol oxidase, xanthine oxidase may exchange electrons with osmium and other transition metal complexes associated with the polymer in the active area of the analyte sensor. As such, xanthine oxidase may cycle between its oxidized and reduced forms, thereby allowing the analyte sensor to maintain an active sensing state. Detection of ethanol in the foregoing analyte sensors is therefore based upon the enzymatic reaction of xanthine oxidase with acetaldehyde, the enzymatic reaction product of ethanol. Moreover, by configuring the enzymes in the analyte sensor in the foregoing manner, the alcohol oxidase may undergo re-oxidation with molecular oxygen to maintain its activity.

FIG. 5A shows the concerted enzymatic reaction cycle associated with ethanol detection using alcohol oxidase and xanthine oxidase disposed directly upon a working electrode, according to various embodiments of the present disclosure. Xanthine oxidase is covalently bonded to a polymer in the active area of the analyte sensor, and alcohol oxidase is non-covalently associated with the polymer in the active area. In addition to xanthine oxidase, an osmium complex or other transition metal complex capable of exchanging electrons with this enzyme is also covalently bonded to the polymer. As shown in FIG. 5A, ethanol reacts with oxidized (active) alcohol oxidase in the presence of a flavin co-factor (FAD-already bonded with the alcohol oxidase), thereby forming reduced alcohol oxidase, acetaldehyde, and hydrogen peroxide. The reduced alcohol oxidase may be re-oxidized with molecular oxygen as shown to return the alcohol oxidase to its catalytically active oxidized form.

Referring still to FIG. 5A, the acetaldehyde enzymatically formed from ethanol then undergoes a subsequent reaction with the oxidized form of xanthine oxidase in the presence of a flavin co-factor that is present natively with the enzyme. Acetic acid is formed in this process and the xanthine oxidase is transformed into a reduced state. The reduced xanthine oxidase may then react with the transition metal electron transfer agent associated with the polymer to transfer electrons to the working electrode, thereby producing a current and regenerating the oxidized form of xanthine oxidase. Although not shown in FIG. 5A, hydrogen peroxide is separately cleared from the sensor environment by catalase that is present in the active area.

As can be appreciated from FIG. 5A, the amount of enzymatically formed acetaldehyde is proportional to the amount of ethanol originally present. As such, the current produced at the working electrode during the xanthine oxidase oxidation of the acetaldehyde may be proportional to the amount of acetaldehyde present, and, by extension, the amount of ethanol. Correlation of the working electrode current to the ethanol concentration may take place by referring to a lookup table of currents at known ethanol concentrations or by utilizing a calibration curve, the concepts of which are described in more detail hereinabove.

Similarly, the current produced at the working electrode when analyzing for ketones may be proportional to the amount of β-hydroxybutyrate that is oxidized to form acetoacetone (FIGS. 5B-5D). Correlation of the current at the working electrode may therefore take place in a manner related to that provided above for ethanol (e.g., using a calibration curve or lookup table).

Accordingly, in more specific embodiments, the present disclosure provides alcohol sensors based upon a concerted enzymatic reaction of alcohol oxidase and xanthine oxidase. More specifically, the alcohol sensors may comprise a sensor tail comprising at least a working electrode, and at least one active area disposed upon a surface of the working electrode, wherein the at least one active area comprises alcohol oxidase, xanthine oxidase, catalase, a polymer, and an electron transfer agent. The electron transfer agent and the xanthine oxidase may be covalently bonded to the polymer, and the alcohol oxidase is not covalently bonded to the polymer, according to particular embodiments. The alcohol oxidase and the xanthine oxidase are capable of interacting in concert to generate a signal at the working electrode that is proportional to an alcohol concentration. More specifically, the alcohol oxidase and the xanthine oxidase are both disposed directly upon the working electrode in order to accomplish the foregoing.

According to more specific embodiments, the catalase in the at least one active area of the alcohol sensors is not covalently bonded to the polymer. The catalase may be present in an amount ranging from about 1% to about 50% by weight of the polymer, more particularly from about 1% to about 10% by weight of the polymer, or from about 1% to about 5% by weight of the polymer.

As such, the present disclosure also provides detection methods based upon a concerted enzymatic reaction, in which a concerted enzyme pair is disposed directly upon the surface of a working electrode. According to various embodiments, the detection methods may comprise: exposing an analyte sensor to a fluid comprising an analyte, the analyte sensor comprising a sensor tail comprising at least a working electrode and at least one active area disposed upon a surface of the working electrode, the at least one active area comprising a first enzyme, a second enzyme, and a polymer. The first enzyme and the second enzyme are capable of interacting in concert, with the second enzyme being covalently bonded to the polymer and unreactive with the analyte. The methods further include: reacting the analyte with the first enzyme to form a first product; reacting the first product with the second enzyme to form a second product to generate a signal at the working electrode; and correlating the signal to a concentration of the analyte in the fluid.

According to more specific embodiments, an electron transfer agent may also be covalently bonded to the polymer when performing the foregoing methods. Suitable electron transfer agents are described in more detail above. In some or other embodiments, the first enzyme is not covalently bonded to the polymer in the at least one active area, particularly when a covalently bonded electron transfer agent is present.

In more specific embodiments, ethanol detection methods of the present disclosure may comprise: exposing an analyte sensor to a fluid, particularly a biological fluid, comprising ethanol, the analyte sensor comprising a sensor tail comprising at least a working electrode and at least one active area disposed upon a surface of the working electrode and comprising alcohol oxidase, xanthine oxidase, catalase, a polymer, and an electron transfer agent. The electron transfer agent and the xanthine oxidase are covalently bonded to the polymer, and the alcohol oxidase is not covalently bonded to the polymer. The alcohol oxidase and the xanthine oxidase are capable of interacting in concert. The methods further comprise: reacting the ethanol with the alcohol oxidase to form acetaldehyde; reacting the acetaldehyde with the xanthine oxidase to form acetic acid to generate a signal at the working electrode; and correlating the signal to a concentration of the ethanol in the fluid. According to some embodiments, the fluid may be a biological fluid and the analyte sensor may be exposed to the biological fluid in vivo.

Although two different enzymes in a single active area of an analyte sensor may interact in concert with one another to determine an analyte concentration, it is to be appreciated that the enzymes may also function independently of one another to detect alternative analytes in other embodiments. For example, in the case of xanthine oxidase as the second enzyme in the analyte sensors described above, instead of using the analyte sensor to detect ethanol, the analyte sensor may alternatively be used to detect any of the wide array of substrates compatible with xanthine oxidase. Alternative substrates for xanthine oxidase may include, for example, hypoxanthine, xanthine, uric acid, purines, pterins, and similar compounds. When the analyte sensors are used in this manner, the alcohol oxidase may remain unused if no alcohol is present, and/or become inactivated by acetaldehyde/hydrogen peroxide, if these species are not cleared by the xanthine oxidase or another species. Thus, sensors containing concerted enzymes may also be considered capable of detecting multiple analytes, one analyte from the concerted enzyme pair and at least a second analyte from one of the members of the concerted enzyme pair acting independently. Whether such sensors assay a single analyte or multiple analytes may be determined based upon the environment to which the sensor is exposed.

As referenced above, multiple enzymes disposed in separate active areas may also interact in concert to promote detection of a single analyte. In some instances, the multiple enzymes may both be located directly upon the surface of a working electrode, as discussed in more detail above. In alternative analyte sensor configurations containing multiple enzymes in separate active areas, one of the active areas may be isolated from the working electrode so that electron transfer to the working electrode takes place from only one of the active areas. Namely, as discussed in further detail hereinbelow, the active area isolated from the working electrode may promote an enzymatic reaction of an analyte of interest to produce a reaction product (substrate) that is itself reactive with the enzyme in an active area in direct contact with the working electrode. A signal associated with the enzymatic reaction taking place in the active area in direct contact with the working electrode then provides a basis for detecting the analyte. Correlation of the signal to the analyte concentration may be accomplished in a manner similar to that discussed in more detail above.

Figure 5E:
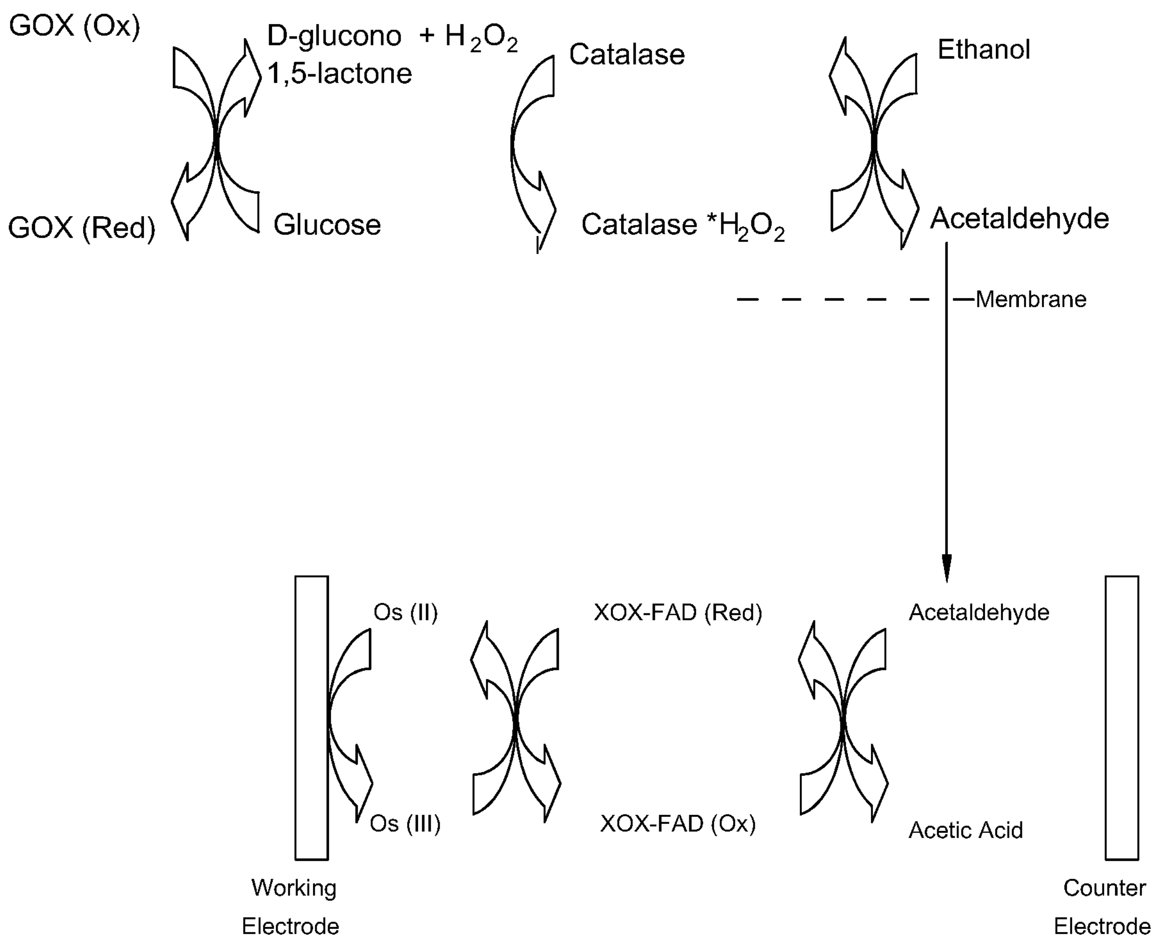
FIG. 5E shows the concerted enzymatic reaction cycle associated with ethanol detection using glucose oxidase, catalase, and xanthine oxidase, in which glucose oxidase is remote from a working electrode and xanthine oxidase is located directly upon the working electrode, according to various embodiments of the present disclosure.

More specifically, FIG. 5E shows the concerted enzymatic reaction cycle associated with ethanol detection using glucose oxidase and xanthine oxidase, as further mediated by catalase, when only the xanthine oxidase or xanthine oxidase and catalase is disposed upon the surface of a working electrode, according to various embodiments of the present disclosure. The concerted enzymatic reaction cycle shown in FIG. 5E is dependent upon glucose and ethanol being co-present with one another in a fluid during analysis, as explained hereinafter. Since glucose is a ubiquitous biological nutrient, it is frequently found co-present with other analytes when assaying a biological fluid. Should a particular fluid undergoing analysis be deficient in glucose, however, certain embodiments of the present disclosure may feature adding glucose to the fluid to promote detection of ethanol or another alcohol using the concerted enzymatic reaction of glucose oxidase and xanthine oxidase.

Figure 6C:
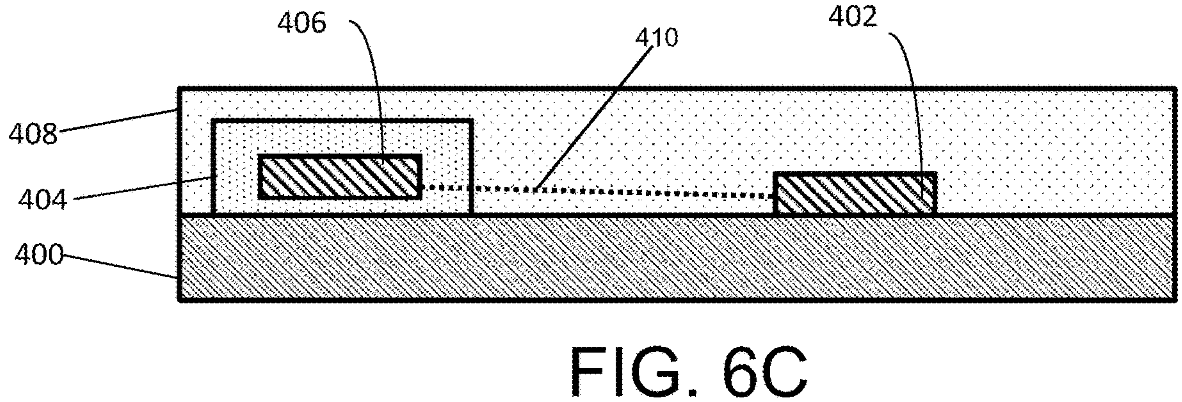
FIG. 6C shows a diagram an illustrative working electrode in which a first active area and a second active area are laterally spaced apart from one another upon a working electrode, and one of the active areas is separated from the working electrode by a membrane.

Before further discussing the concerted enzymatic reaction depicted in FIG. 5E, illustrative analyte sensor configurations featuring at least one active area isolated from a working electrode will first be described in further detail. As mentioned previously, the analyte sensor configurations shown in FIGS. 2A-4 all feature one or more working electrodes having one or more active areas disposed directly upon a surface of each working electrode. In contrast, FIGS. 6A, 6B and 6C show diagrams of a working electrode in which a first active area is disposed directly upon a surface of the working electrode and a second active area is separated from (spaced apart from or remote from) the working electrode by a membrane. The working electrode configurations depicted in FIGS. 6A, 6B and 6C may be substituted for any of the particular working electrode configurations depicted in FIGS. 2A-4. That is, the working electrode configurations depicted in FIGS. 6A, 6B and 6C may be combined in any suitable way with a counter electrode and/or a reference electrode, membrane, substrates, and similar structures in an analyte sensor.

As shown in FIG. 6A, working electrode 400 has active area 402 disposed directly upon a surface thereof. Active area 402 comprises a first enzyme covalently bound to a first polymer. Typically, an electron transfer agent is also present in active area 402, with the electron transfer agent also being covalently bound to the polymer. Active area 402 is overcoated with membrane 404. Membrane 404 may also overcoat the surface of working electrode 400, as depicted, as well as other portions of an analyte sensor in which working electrode 400 is present. Membrane 404 isolates active area 406 from working electrode 400, such that electron exchange between the two is precluded. Active area 406 comprises a second enzyme covalently bound to a second polymer, but without a separate electron transfer agent being present. Although FIG. 6A shows active area 406 disposed directly over active area 402, it is to be appreciated that they may be laterally spaced apart from one another in alternative configurations also compatible with the present disclosure. Membrane 408 overcoats active area 406, and optionally other sensor components, to provide mass transport limiting properties. Similarly, as shown in FIG. 6B, membrane 404 need not necessarily extend the same lateral distance as does membrane 408 upon working electrode 400. Indeed, membrane 404 in FIG. 6B overcoats active area 402 but only a portion of the surface of working electrode 400, with membrane 408 overcoating active area 406, the surface of membrane 404 and the remainder of the surface of working electrode 400 not overcoated by membrane 404. Active areas 402 and 406 may also be laterally offset from one another in some embodiments, as shown in FIG. 6C, wherein active area 406 is again isolated from working electrode 400 by membrane 404.

Membrane 408 is permeable to an analyte and any additional components needed to promote an enzymatic reaction in active area 406. Membrane 404, in contrast, is permeable to a product formed in active area 406. That is, an analyte reacts in active area 406 to form a first product, which then diffuses through membrane 404 and is subsequently reacted further in active area 402 to form a second product or products. The second product is subsequently detectable based on electron exchange with working electrode 400.

Optionally, lead 410 may extend between active areas 402 and 406 if glucose detection is desired.

In an alcohol sensor featuring detection based upon a concerted enzymatic reaction of glucose oxidase and xanthine oxidase, the glucose oxidase is present in active area 406 and the xanthine oxidase is present in active area 402. Referring again to FIG. 5E, with continued reference to FIGS. 6A, 6B and 6C, glucose oxidase is present in active area 406 and converts exogenous glucose into D-glucono-lactone-1,5-dione and hydrogen peroxide. Unlike alcohol sensors featuring detection based upon a concerted enzymatic reaction between alcohol oxidase and xanthine oxide (FIG. 5A), the catalase plays a more active role in the concerted enzymatic reaction depicted in FIG. 5E. Namely, catalase reacts with the hydrogen peroxide to form a catalase-hydrogen peroxide complex (the same peroxide-clearing function exhibited by catalase in the concerted enzymatic reaction of alcohol oxidase and xanthine oxidase), with the complex subsequently reacting with ethanol to form acetaldehyde. The acetaldehyde formed in active area 406 upon reacting ethanol with catalase-hydrogen peroxide complex diffuses through membrane 404, which separates active area 406 from active area 402. Alternately, the catalase may be present in active area 402, in which case the hydrogen peroxide formed in active area 406 may diffuse through membrane 404 into active area 402, form the catalase-hydrogen peroxide complex in active area 402, and oxidize ethanol to acetaldehyde in active area 402. Once acetaldehyde has been formed in active area 402, the concerted enzymatic reaction may continue as depicted in FIG. 5E. Membrane 404 may comprise crosslinked polyvinylpyridine, which is permeable to acetaldehyde. The acetaldehyde then reacts with xanthine oxidase in active area 402 to form acetic acid in a manner similar to that described above for FIG. 5A.

Accordingly, alcohol sensors of the present disclosure may comprise: a sensor tail comprising at least a working electrode; a first active area disposed upon a surface of the working electrode, the first active area comprising xanthine oxidase, catalase, a first polymer, and an electron transfer agent; wherein the xanthine oxidase and the electron transfer agent are covalently bonded to the first polymer; a first membrane overcoating the first active area, the first membrane comprising a first membrane polymer and being permeable to acetaldehyde; a second active area disposed upon the first membrane, the second active area comprising glucose oxidase, catalase, and a second polymer; wherein the glucose oxidase is covalently bonded to the second polymer; and a second membrane overcoating the second active area, the second membrane comprising a second membrane polymer and being permeable to glucose and alcohol; wherein the glucose oxidase and the xanthine oxidase are capable of interacting in concert to generate a signal at the working electrode proportional to an alcohol concentration. The alcohol may be ethanol in more specific embodiments.

The first membrane polymer and the second membrane polymer may differ from one another, according to some embodiments. The first membrane polymer may be crosslinked polyvinylpyridine, according to some embodiments. Crosslinked polyvinylpyridine is readily permeable to acetaldehyde in the embodiments of the present disclosure. The second membrane polymer may be a crosslinked polyvinylpyridine-co-styrene polymer, in which a portion of the pyridine nitrogen atoms were functionalized with a non-crosslinked poly(ethylene glycol) tail and a portion of the pyridine nitrogen atoms were functionalized with an alkylsulfonic acid group. Such second membrane polymers are readily permeable to both glucose and ethanol.

According to some embodiments, the catalase is not covalently bonded to the first polymer or the second polymer in the first active area or the second active area. The catalase may be physically constrained within the first active area and the second active area by any of the first polymer, the second polymer, the first membrane polymer, or the second membrane polymer.

Similarly, methods for analyzing for ethanol or another alcohol using the foregoing analyte sensors comprising in concert interacting glucose oxidase and xanthine oxidase may comprise: exposing an analyte sensor to a fluid comprising ethanol and glucose; oxidizing the glucose with the glucose oxidase to generate hydrogen peroxide; forming a catalase-hydrogen peroxide complex; oxidizing the alcohol with the catalase-hydrogen peroxide complex to form acetaldehyde; reacting the acetaldehyde with the xanthine oxidase to form acetic acid to generate a signal at the working electrode; and correlating the signal to a concentration of the alcohol in the fluid. The fluid may comprise a biological fluid, according to various embodiments of the present disclosure. Correlation of the signal to the concentration of alcohol in the fluid may take place using any suitable correlation technique outlined in more detail above.

In still other embodiments of the present disclosure, multiple enzymes may be arranged within the active areas of separate working electrodes. As such, the signals associated with the enzymatic reaction occurring within each active area may be measured separately by interrogating each working electrode at the same time or at different times. The signal associated with each active area may then be correlated to the concentration of separate analytes.

As discussed above, a membrane (i.e., a mass transport limiting membrane) may overcoat one or more of the active areas in an analyte sensor in order to increase biocompatibility and to alter the analyte flux to the active areas. Such membranes may be present in any of the analyte sensors disclosed herein. Because different analytes may exhibit varying permeability values within a given membrane, an analyte sensor configured to analyze for multiple analytes may exhibit dissimilar sensitivities for each analyte. One approach for addressing differing sensitivity values may involve utilizing different membrane thicknesses over each active area. Although feasible, this approach may be difficult to put into practice from a manufacturing standpoint. Namely, it can be difficult to vary the membrane thickness at different locations using typical dip coating techniques that are used for membrane deposition. Another possible approach is to use active areas with different sizes for each analyte.

Analyte sensors having active areas configured for assaying different analytes upon separate working electrodes may address the foregoing issue associated with dissimilar analyte sensitivity. Namely, the disclosure hereinafter provides various ways in which the membrane permeability may be altered upon each working electrode to levelize the analyte membrane permeability at each location. That is, the disclosure herein allows the analyte permeability and sensitivity at each working electrode to be independently varied. According to the disclosure herein, mass transport limiting membranes comprising two or more different membrane polymers may afford more levelized analyte permeability at each working electrode. Particular membrane configurations that may be suitable for levelizing the analyte permeability upon one or more of the working electrodes include bilayer membranes and mixed membranes, each comprising two or more different membrane polymers. Surprisingly, bilayer membranes and mixed membranes comprising a membrane polymer that is individually unsuitable for promoting permeability of a given analyte may provide satisfactory performance when located in a bilayer membrane or mixed membrane, as discussed hereinafter. This approach may be advantageous compared to varying the size of the active areas upon each working electrode to provide comparable sensitivity values for each analyte.

Accordingly, in some embodiments, analyte sensors featuring two or more enzymes arranged upon separate working electrodes may comprise: a sensor tail comprising at least a first working electrode and a second working electrode, a first active area located upon a surface of the first working electrode, a second active area located upon a surface of the second working electrode, a multi-component membrane overcoating the first active area, and a homogenous membrane overcoating the second active area. The first active area comprises a first polymer and a first analyte-responsive enzyme that is reactive with a first analyte, and the second active area comprises a second polymer and a second analyte-responsive enzyme that is reactive with a second analyte. The first analyte-responsive enzyme and the second analyte-responsive enzyme are different and are reactive with different analytes. The multi-component membrane comprises at least a first membrane polymer and a second membrane polymer that differ from one another. The homogeneous membrane comprises one of the first membrane polymer and the second membrane polymer.

Particular configurations of the multi-component membranes described above may comprise a bilayer membrane in some embodiments or an admixture of the membrane polymers in other embodiments. Surprisingly, bilayer membranes and admixed membranes may function to levelize the analyte permeability, as explained in further detail below.

Analyte sensors of the present disclosure having two different active areas located upon separate working electrodes may employ a sensor configuration similar to that described above in FIG. 3 or a variant thereof. For example, in some embodiments, a counter/reference electrode may replace separate counter and reference electrodes in an analyte sensor bearing two or more working electrodes. Similarly, the layer configuration and arrangement within analyte sensors having two different active areas located upon separate working electrodes may differ from that depicted in FIG. 3. Further details concerning the membrane disposition upon each active area is provided below in reference to FIG. 7.

According to more specific embodiments of the present disclosure, analyte sensors having multiple working electrodes may comprise active areas in which an electron transfer agent is covalently bonded to the polymer in each active area. In some or other embodiments, such analyte sensors may feature the first analyte-responsive enzyme covalently bonded to the polymer in the first active area and the second analyte-responsive covalently bonded to the polymer in the second active area. Again, in particular embodiments, the first analyte-responsive enzyme may be a glucose-responsive enzyme, such as glucose oxidase, and the second analyte-responsive enzyme may be a lactate-responsive enzyme, such as lactate oxidase.

In still other more specific embodiments, analyte sensors having multiple working electrodes may comprise a sensor tail configured for insertion into a tissue.

In some embodiments, a bilayer membrane may overcoat the first active area upon one of the working electrodes. The bilayer membrane comprises a first membrane polymer and a second membrane polymer that are layered upon one another over the active area. In more specific embodiments, the first membrane polymer may be disposed directly upon the active area of a first working electrode, and the second membrane polymer may be disposed upon the first membrane polymer to define the bilayer membrane. In such embodiments, the second membrane polymer is present in the homogenous membrane located upon the second working electrode. Such bilayer configurations may be prepared, in some embodiments, by coating the first membrane polymer only upon the first working electrode (e.g., by spray coating, painting, inkjet printing, roller coating, or the like) and then coating the second membrane polymer upon both working electrodes at the same time (e.g., by dip coating or a similar technique). In other embodiments, the bilayer membrane may be configured as above, with the first membrane polymer being located upon the second working electrode.

Figure 7:
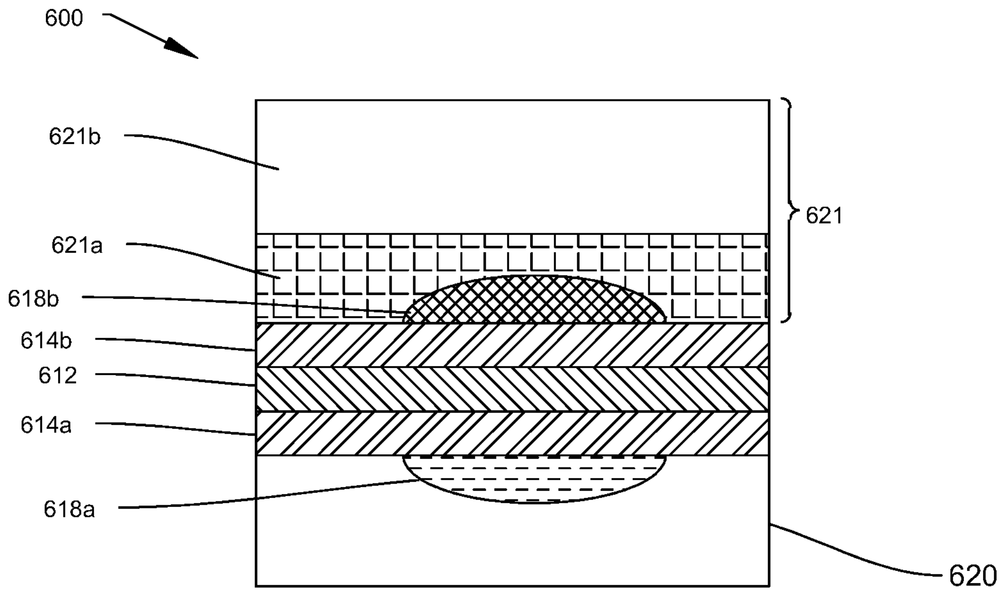
FIG. 7 shows an illustrative schematic of a portion of an analyte sensor having two working electrodes and featuring a bilayer membrane overcoating one of the two working electrodes, which is compatible for use in some embodiments of the disclosure herein.

FIG. 7 shows an illustrative schematic of a portion of an analyte sensor having two working electrodes and featuring a bilayer membrane overcoating one of the two working electrodes, which is compatible for use in some embodiments of the disclosure herein. As shown in FIG. 7, the analyte sensor features sensor tail 600 having working electrodes **614*a* and 614*b* disposed on opposite faces of substrate 612. Active area 618*a* is disposed upon working electrode 614*a*, and active area 618*b* is disposed upon working electrode 614*b*. Active areas 618*a* and 618*b* contain different analyte-responsive enzymes and are configured to assay for different analytes, in accordance with the disclosure herein. Although FIG. 7 has shown active areas 618*a* and 618*b* to be disposed generally opposite on another with respect to substrate 612, it is to be appreciate that active areas 618*a* and 618*b* may be laterally spaced apart (offset) from one another upon opposite faces of substrate 612. Laterally spaced-apart configurations for active areas 618*a* and 618*b* may be particularly advantageous for overcoating each active areas 618*a* and 618*b*** with mass transport limiting membranes, as discussed hereinafter.

As further shown in FIG. 7, active area **618*a* is overcoated with membrane layer 620. Membrane layer 620 is a homogenous membrane comprising a single membrane polymer. Active area 618*b* is overcoated with bilayer membrane 621, which comprises membrane layer 621*a* in direct contact with active area 618*b* and membrane layer 621*b* overlaying membrane layer 621*a*. Membrane layers 621*a* and 621*b* comprise different membrane polymers. As described above, in particular embodiments, membrane layer 620 and membrane layer 621*b*** may comprise the same membrane polymer.

Analyte sensors having multiple active areas upon separate working electrodes, in which one of the active areas is overcoated with a bilayer membrane, may display levelized or independently variable analyte permeability, according to one or more embodiments. That is, the analyte sensors may have sensitivities for two different analytes that are closer to one another than if the bilayer membrane were not present. In such analyte sensor configurations, the active area overcoated with the homogeneous membrane (e.g., membrane layer 620 in FIG. 7), may exhibit analyte permeability for a first analyte that is characteristic of its particular membrane polymer. Surprisingly, a bilayer membrane (e.g., bilayer membrane 621 in FIG. 7) may contain a membrane polymer that does not negatively impact the permeability of a second analyte (i.e., a membrane polymer having neutral permeability influence), thereby allowing the other membrane polymer comprising the bilayer membrane to exhibit its characteristic permeability for the second analyte as if the first membrane polymer was not present. Thus, according to various embodiments, the membrane polymer having neutral permeability influence and the membrane polymer comprising the homogeneous membrane may constitute the same polymer.

In some or other specific embodiments, the membrane polymer having neutral permeability influence may comprise the inner layer of the bilayer membrane. Thus, according to such embodiments, the inner layer of the bilayer membrane and the homogeneous membrane may constitute the same membrane polymer. In other specific embodiments, the outer layer of the bilayer membrane and the homogeneous membrane may constitute the same membrane polymer.

In particular embodiments, the first active area may comprise a glucose-responsive enzyme, such as glucose oxidase, and the second active area may comprise a lactate-responsive enzyme, such as lactate oxidase. Thus, according to such embodiments, the first active area containing the glucose-responsive enzyme may be overcoated with the bilayer membrane, and the second active area containing the lactate-responsive enzyme may be overacted with the homogeneous (single-component membrane polymer) membrane. In still more specific embodiments, the second active area may comprise a polymer, an albumin, and a lactate-responsive enzyme covalently bonded to the polymer. In yet still more specific embodiments, the homogenous membrane overcoating the second active area may comprise at least a crosslinked polyvinylpyridine homopolymer or copolymer, and the bilayer membrane overcoating the first active area may also comprise the polyvinylpyridine homopolymer or copolymer.

In other embodiments of the present disclosure, the multi-component membrane may comprise an admixture (homogeneous blend) of the first membrane polymer and the second membrane polymer. Such analyte sensor configurations may be similar in appearance to that shown in FIG. 7, except for replacement of bilayer membrane 621 with an admixed membrane comprising the two different membrane polymers in a homogeneous blend. As with analyte sensors comprising a bilayer membrane disposed upon one of the active areas, a homogeneous membrane comprising one of the first membrane polymer or the second membrane polymer of the admixed membrane may overcoat the other active area upon the second working electrode.

Similar to a bilayer membrane, an admixed membrane containing a membrane polymer that neutrally influences the permeability of a second analyte may allow the admixed membrane to exhibit permeability for the second analyte that is largely characteristic of the other membrane polymer in the admixture. Thus, according to various embodiments of the present disclosure, the membrane polymer of the homogeneous membrane and one of the membrane polymers of the admixed membrane may be chosen such that the permeability of the second analyte through the admixed membrane is not substantially altered by the membrane polymer. In particular embodiments, the first active area may comprise a glucose-responsive enzyme, such as glucose oxidase, and the second active area may comprise a lactate-responsive enzyme, such as lactate oxidase. Thus, according to such embodiments, the first active area containing the glucose-responsive enzyme may be overcoated with the admixed membrane, and the second active area containing the lactate-responsive enzyme may be overacted with the homogeneous (single-component membrane polymer) membrane. In still more specific embodiments, the second active area may comprise a polymer, an albumin, and a lactate-responsive enzyme covalently bonded to the polymer. In yet still more specific embodiments, the homogenous membrane overcoating the second active area may comprise at least a crosslinked polyvinylpyridine homopolymer or copolymer, and the admixed membrane overcoating the first active area may also comprise the polyvinylpyridine homopolymer or copolymer.

As referenced above, bilayer membranes and admixed membranes may levelize analyte permeability in analyte sensors of the present disclosure, wherein two or more active areas are spatially separated from one another and can be overcoated with different mass transport limiting membranes. Specifically, bilayer membranes and admixed membranes of the present disclosure may levelize analyte permeability in analyte sensors having separate working electrodes and comprising two or more active areas with different enzymes, with at least one active area being located at each working electrode. Thus, such membranes may advantageously allow the sensor sensitivity to be varied independently for each analyte. The membrane thickness and/or the relative proportion of the first membrane polymer to the second membrane polymer represent other parameters that may be varied to adjust the characteristic permeability of the analytes at each working electrode.

Accordingly, methods for using an analyte sensor containing two working electrodes may comprise exposing an analyte sensor to a fluid comprising at least one analyte. The analyte sensor comprises a sensor tail comprising at least a first working electrode and a second working electrode. A first active area is disposed upon a surface of the first working electrode, and a second active area is disposed upon a surface of the second working electrode. The first active area comprises a first polymer and a first analyte-responsive enzyme reactive with a first analyte, and the second active area comprises a second polymer and a second analyte-responsive enzyme reactive with a second analyte. The first analyte-responsive enzyme and the second analyte-responsive enzyme are different. A multi-component membrane overcoats the first active area, and a homogeneous membrane overcoats the second active area. The multi-component membrane comprises at least a first membrane polymer and a second membrane polymer that differ from one another, and the homogeneous membrane comprises one of the first membrane polymer or the second membrane polymer. The methods further include obtaining a first signal at or above an oxidation-reduction potential of the first active area, obtaining a second signal at or above the oxidation-reduction potential of the second active area, and correlating the first signal to the concentration of the first analyte in the fluid and the second signal to the concentration of the second analyte in the fluid. The first signal is proportional to the concentration of the first analyte in the fluid, and the second signal is proportional to the concentration of the second analyte in the fluid.

According to more specific embodiments, the first signal and the second signal maybe measured at different times. Thus, in such embodiments, a potential may be alternately applied to the first working electrode and the second working electrode. In other embodiments, the first signal and the second signal may be measured simultaneously via a first channel and a second channel, in which case a potential may be applied to both electrodes at the same time.

Embodiments disclosed herein include:

A. Analyte sensors containing two active areas with different analyte-responsive enzymes. The analyte sensors comprise: a sensor tail comprising at least a working electrode; and at least two active areas disposed upon a surface of the working electrode, each active area comprising an analyte-responsive enzyme and a polymer, wherein the analyte-responsive enzyme in each active area is different; and wherein each active area has an oxidation-reduction potential, and the oxidation-reduction potential of a first active area is sufficiently separated from the oxidation-reduction potential of a second active area to allow production of a signal from the first active area independent of production of a signal from the second active area.

B. Methods for assaying two or more analytes using a first active area and a second active area containing different analyte-responsive enzymes. The methods comprise: exposing an analyte sensor to a fluid comprising at least one analyte; wherein the analyte sensor comprises a sensor tail comprising at least a working electrode and at least two active areas disposed upon a surface of the working electrode, each active area comprising an analyte-responsive enzyme and a polymer; wherein the analyte-responsive enzyme in each active area is different; and wherein each active area has an oxidation-reduction potential, and the oxidation-reduction potential of a first active area is sufficiently separated from the oxidation-reduction potential of a second active area to allow production of a signal from the first active area independent of production of a signal from the second active area; obtaining a first signal at or above the oxidation-reduction potential of the first active area, the first signal being proportional to a concentration of a first analyte; obtaining a second signal at or above the oxidation-reduction potential of the second active area, the second signal being a composite signal comprising a signal contribution from the first active area and a signal contribution from the second active area; and subtracting the first signal from the second signal to obtain a difference signal, the difference signal being proportional to a concentration of the second analyte.

C. Analyte sensors containing two or more enzymes that are capable of interacting in concert with one another. The analyte sensors comprise: a sensor tail comprising at least a working electrode; and at least one active area disposed upon a surface of the working electrode, the at least one active area comprising a first enzyme, a second enzyme, and a polymer, the first enzyme and the second enzyme being capable of interacting in concert; wherein the first enzyme is capable of converting an analyte into a first product, and the second enzyme is capable of converting the first product into a second product to generate a signal at the working electrode; and wherein the second enzyme is covalently bonded to the polymer and is unreactive with the analyte.

D. Methods for assaying an analyte using two or more enzymes that are capable of interacting in concert with one another. The methods comprise: exposing an analyte sensor to a fluid comprising an analyte; wherein the analyte sensor comprises a sensor tail comprising at least a working electrode and at least one active area disposed upon a surface of the working electrode, the at least one active area comprising a first enzyme, a second enzyme, and a polymer; wherein the first enzyme and the second enzyme are capable of interacting in concert, and the second enzyme is covalently bonded to the polymer and is unreactive with the analyte; reacting the analyte with the first enzyme to form a first product; reacting the first product with the second enzyme to form a second product to generate a signal at the working electrode; and correlating the signal to a concentration of the analyte in the fluid.

E. Alcohol sensors. The alcohol sensors comprise: a sensor tail comprising at least a working electrode; and at least one active area disposed upon a surface of the working electrode, the at least one active area comprising alcohol oxidase, xanthine oxidase, catalase, a polymer, and an electron transfer agent; wherein the electron transfer agent and the xanthine oxidase are covalently bonded to the polymer, and the alcohol oxidase is not covalently bonded to the polymer; and wherein the alcohol oxidase and the xanthine oxidase are capable of interacting in concert to generate a signal at the working electrode proportional to an alcohol concentration.

F. Methods for detecting an alcohol. The methods comprise: exposing an analyte sensor to a fluid comprising ethanol; wherein the analyte sensor comprises a sensor tail comprising at least a working electrode and at least one active area disposed upon a surface of the working electrode, the at least one active area comprising alcohol oxidase, xanthine oxidase, catalase, a polymer, and an electron transfer agent; wherein the electron transfer agent and the xanthine oxidase are covalently bonded to the polymer, and the alcohol oxidase is not covalently bonded to the polymer; and wherein the alcohol oxidase and the xanthine oxidase are capable of interacting in concert; reacting the ethanol with the alcohol oxidase to form acetaldehyde; reacting the acetaldehyde with the xanthine oxidase to form acetic acid to generate a signal at the working electrode; and correlating the signal to a concentration of the ethanol in the fluid.

G. Analyte sensors comprising two or more working electrodes that are overcoated with different mass transport limiting membranes. The analyte sensors comprise: a sensor tail comprising at least a first working electrode and a second working electrode; a first active area disposed upon a surface of the first working electrode, the first active area comprising a first polymer and a first analyte-responsive enzyme reactive with a first analyte; a second active area disposed upon a surface of the second working electrode, the second active area comprising a second polymer and a second analyte-responsive enzyme reactive with a second analyte; wherein the first analyte-responsive enzyme and the second analyte-responsive enzyme are different; a multi-component membrane overcoating the first active area, the multi-component membrane comprising at least a first membrane polymer and a second membrane polymer that differ from one another; and a homogeneous membrane overcoating the second active area and differing in composition from the multi-component membrane, the homogeneous membrane comprising one of the first membrane polymer and the second membrane polymer.

H. Methods for assaying two or more analytes using two working electrodes overcoated with different mass transport limiting membranes. The methods comprise: exposing an analyte sensor to a fluid comprising at least one analyte; wherein the analyte sensor comprises a sensor tail comprising at least a first working electrode and second working electrode; wherein a first active area is disposed upon a surface of the first working electrode, the first active area comprising a first polymer and a first analyte-responsive enzyme reactive with a first analyte, and a second active area is disposed upon a surface of the second working electrode, the second active area comprising a second polymer and a second analyte-responsive enzyme reactive with a second analyte; wherein the first analyte-responsive enzyme and the second analyte-responsive enzyme are different; and wherein a multi-component membrane overcoats the first active area and a homogeneous membrane overcoats the second active area, the multi-component membrane comprising at least a first membrane polymer and a second membrane polymer that differ from one another, and the homogeneous membrane comprising one of the first membrane polymer or the second membrane polymer and differing in composition from the multi-component membrane; obtaining a first signal at or above an oxidation-reduction potential of the first active area, the first signal being proportional to a concentration of a first analyte in the fluid; obtaining a second signal at or above an oxidation-reduction potential of the second active area, the second signal being proportional to a concentration of the second analyte in the fluid; and correlating the first signal to the concentration of the first analyte in the fluid and the second signal to the concentration of the second analyte in the fluid.

I. Alcohol sensors comprising glucose oxidase and xanthine oxidase interacting in concert. The alcohol sensors comprise: a sensor tail comprising at least a working electrode; a first active area disposed upon a surface of the working electrode, the first active area comprising xanthine oxidase, catalase, a first polymer, and an electron transfer agent; wherein the xanthine oxidase and the electron transfer agent are covalently bonded to the first polymer; a first membrane overcoating the first active area, the first membrane comprising a first membrane polymer and being permeable to acetaldehyde; a second active area disposed upon the first membrane, the second active area comprising glucose oxidase, catalase, and a second polymer; wherein the glucose oxidase is covalently bonded to the second polymer; and a second membrane overcoating the second active area, the second membrane comprising a second membrane polymer and being permeable to glucose and alcohol; wherein the glucose oxidase and the xanthine oxidase are capable of interacting in concert to generate a signal at the working electrode proportional to an alcohol concentration.

J. Methods for detecting an alcohol using a concerted interaction between glucose oxidase and xanthine oxidase. The methods comprise: exposing an analyte sensor to a fluid comprising ethanol and glucose; wherein the analyte sensor comprises a sensor tail comprising: at least a working electrode; a first active area disposed upon a surface of the working electrode, the first active area comprising xanthine oxidase, catalase, a first polymer, and an electron transfer agent, the xanthine oxidase and the electron transfer agent being covalently bonded to the first polymer; a first membrane overcoating the first active area, the first membrane comprising a first membrane polymer and being permeable to acetaldehyde; a second active area disposed upon the first membrane, the second active area comprising glucose oxidase, catalase, and a second polymer, the glucose oxidase being covalently bonded to the second polymer; and a second membrane overcoating the second active area, the second membrane comprising a second membrane polymer and being permeable to glucose and alcohol; wherein the glucose oxidase and the xanthine oxidase are capable of interacting in concert; oxidizing the glucose with the glucose oxidase to generate hydrogen peroxide; forming a catalase-hydrogen peroxide complex; oxidizing the alcohol with the catalase-hydrogen peroxide complex to form acetaldehyde; reacting the acetaldehyde with the xanthine oxidase to form acetic acid to generate a signal at the working electrode; and correlating the signal to a concentration of the alcohol in the fluid.

Each of embodiments A and B may have one or more of the following additional elements in any combination:

Element 1: wherein the sensor tail is configured for insertion into a tissue.

Element 2: wherein the oxidation-reduction potential of the first active area is separated from the oxidation-reduction potential of the second active area by at least about 100 mV.

Element 3: wherein the first active area comprises a first electron transfer agent and the second active area comprises a second electron transfer agent, the first and second electron transfer agents being different.

Element 4: wherein the first electron transfer agent is covalently bonded to the polymer in the first active area and the second electron transfer agent is covalently bonded to the polymer in the second active area.

Element 5: wherein the analyte-responsive enzyme in each active area is covalently bonded to the polymer.

Element 6: wherein the analyte sensor further comprises: a mass transport limiting membrane overcoating at least the at least two active areas.

Element 7: wherein at least one of the at least two active areas comprises two or more analyte-responsive enzymes, the two or more analyte-responsive enzymes interacting in concert to generate a signal proportional to the concentration of a single analyte.

Element 8: wherein the fluid is a biological fluid and the analyte sensor is exposed to the biological fluid in vivo.

Element 9: wherein a mass transport limiting membrane overcoats at least the at least two active areas.

Element 10: wherein the analyte sensor comprises glucose oxidase as a first enzyme and lactate oxidase as a second enzyme.

Each of embodiments C and D may have one or more of the following additional elements in any combination:

Element 11: wherein the first enzyme is alcohol oxidase and the second enzyme is xanthine oxidase.

Element 12: wherein the at least one active area further comprises catalase.

Element 13: wherein the catalase is not covalently bonded to the polymer.

Element 14: wherein the alcohol oxidase is not covalently bonded to the polymer.

Element 15: wherein the first enzyme is not covalently bonded to the polymer.

Element 16: wherein the at least one active area comprises an electron transfer agent that is covalently bonded to the polymer.

Element 17: wherein the sensor tail is configured for insertion into a tissue.

Element 18: wherein the analyte sensor further comprises: a mass transport limiting membrane overcoating at least the at least one active area.

Element 19: wherein the fluid is a biological fluid and the analyte sensor is exposed to the biological fluid in vivo.

Element 20: wherein a mass transport limiting membrane overcoats the at least one active area.

Each of embodiments E and F may have one or more of the following additional elements in any combination:

Element 21: wherein the catalase is not covalently bonded to the polymer.

Element 22: wherein the sensor tail is configured for insertion into a tissue.

Element 23: wherein the alcohol sensor further comprises: a mass transport limiting membrane overcoating at least the at least one active area.

Element 24: wherein the fluid is a biological fluid and the analyte sensor is exposed to the biological fluid in vivo.

Element 25: wherein a mass transport limiting membrane overcoats the at least one active area.

Each of embodiments G and H may have one or more of the following additional elements in any combination:

Element 26: wherein the multi-component membrane comprises a bilayer membrane.

Element 27: wherein the first membrane polymer is disposed directly upon the first active area, and the second membrane polymer is disposed upon the first membrane polymer to define the bilayer membrane, the second membrane polymer also being present in the homogeneous membrane.

Element 28: wherein the multi-component membrane comprises an admixture of the first membrane polymer and the second membrane polymer.

Element 29: wherein the sensor tail is configured for insertion into a tissue.

Element 30: wherein each active area further comprises an electron transfer agent that is covalently bonded to the polymer.

Element 31: wherein the first analyte-responsive enzyme is covalently bonded to the polymer in the first active area, and the second analyte-responsive enzyme is covalently bonded to the polymer in the second active area.

Element 32: wherein an electron transfer agent is covalently bonded to the polymer in each active area.

Element 33: wherein the analyte-responsive enzyme in each active area is covalently bonded to the polymer.

Element 34: wherein the fluid is a biological fluid and the analyte sensor is exposed to the biological fluid in vivo.

Element 35: wherein the first signal and the second signal are measured at different times.

Element 36: wherein the first signal and the second signal are measured simultaneously via a first channel and a second channel.

Each of embodiments I and J may have one or more of the following additional elements in any combination:

Element 37: wherein the catalase is not covalently bonded to the first polymer or the second polymer.

Element 38: wherein the sensor tail is configured for insertion into a tissue.

Element 39: wherein the first membrane polymer and the second membrane polymer differ from one another.

Element 40: wherein the first membrane polymer comprises a crosslinked polyvinylpyridine.

Element 41: wherein the fluid is a biological fluid and the analyte sensor is exposed to the biological fluid in vivo.

By way of non-limiting example, exemplary combinations applicable to A-J include:

The analyte sensor of A in combination with elements 1 and 2; 1 and 3; 1, 3 and 4; 1 and 5; 1 and 6; 1 and 7; 2 and 3; 2-4; 2 and 5; 2 and 6; 2 and 7; 3-5; 3 and 4; 3 and 5; 3 and 6; 3 and 7; 5 and 6; 6 and 7; 2, 3 and 5; 2, 3 and 6; 2-5; and 2, 5 and 6. The method of B in combination with elements 2 and 3; 2-4; 2 and 5; 2 and 6; 2 and 7; 2 and 8; 3-5; 3 and 4; 3 and 5; 3 and 6; 3 and 7; 3 and 8; 5 and 6; 5 and 8; 6 and 7; 6 and 8; 7 and 8; 2, 3 and 5; 2, 3, 5 and 8; 2, 3 and 6; 2, 3, 6 and 8; 2-5; 2-5 and 8; 2, 5 and 6; 2, 5, 6 and 8; 2, 3 and 8; 3, 5 and 8; 2, 6 and 8; 2, 5 and 8; any one of 2-8 and 9; and any one of 2-8 and 10.

The analyte sensor of C in combination with elements 11 and 12; 11, 12 and 13; 12 and 13; 11 and 14; 11 and 15; 11 and 17; 11 and 18; 12 and 13; 12 and 14; 12 and 15; 12 and 16; 12 and 17; 12 and 18; 15 and 16; 15 and 17; 15 and 18; 16 and 17; 16 and 18; 17 and 18; 11, 12 and 13; 11, 12 and 14; 11-14; 11-14 and 16; 11-14 and 17; 11-14 and 18; 15-17; 15-18; and 15, 17 and 18. The method of D in combination with elements 11 and 12; 11, 12 and 13; 12 and 13; 11 and 14; 11 and 15; 11 and 17; 11 and 18; 11 and 19; 11 and 20; 12 and 13; 12 and 14; 12 and 15; 12 and 16; 12 and 17; 12 and 18; 12 and 19; 12 and 20; 15 and 16; 15 and 17; 15 and 18; 15 and 19; 15 and 20; 16 and 17; 16 and 18; 16 and 19; 16 and 20; 17 and 18; 17 and 19; 17 and 20; 18 and 19; 18 and 20; 19 and 20; 11, 12 and 13; 11, 12, 13 and 19; 11, 12, 13 and 20; 11, 12 and 14; 11, 12, 14 and 19; 11, 12, 14 and 20; 11-14; 11-14 and 19; 11-14 and 20; 11-14 and 16; 11-14, 16 and 19; 11-14, 16 and 20; 11-14 and 17; 11-14, 17 and 19; 11-14, 17 and 20; 11-14 and 18; 11-14, 18 and 19; 11-14, 18 and 20; 15-17; 15-17 and 19; 15-17 and 20; 15-18; 15-18 and 19; 15-18 and 20; 15, 17 and 18; 15, 17, 18 and 19; 15, 17, 18 and 20; any one of 11-16 and 19; and any one of 11-16 and 20.

The analyte sensor of E in combination with elements 21 and 22; 21 and 23; 22 and 23; and 21-23. The method of F in combination with elements 21 and 22; 21 and 23; 22 and 23; 21-23; 21 and 24; 21 and 25.

The analyte sensor of G in combination with elements 26 and 27; 26 and 29; 26, 27 and 29; 26 and 30; 26, 27 and 30; 26 and 31; 26, 27 and 31; 28 and 29; 28 and 30; 28-30; 28 and 31; 29 and 30; 29 and 31; and 30 and 31. The method of H in combination with elements 26 and 27; 26 and 29; 26, 27 and 29; 26 and 30; 26, 27 and 30; 26 and 31; 26, 27 and 31; 28 and 29; 28 and 30; 28-30; 28 and 31; 29 and 30; 29 and 31; 30 and 31; 26 and 33; 26, 27 and 33; 26 and 34; 26, 27 and 34; 26 and 35; 26, 27 and 35; 26 and 36; 26, 27 and 36; 28 and 33; 28 and 34; 28 and 35; 28 and 36; 30 and 33; 30 and 34; 30 and 35; 30 and 36; 33 and 34; 33 and 35; 33 and 36; 34 and 35; and 34 and 36.

The analyte sensor of I in combination with elements 37 and 38; 37 and 39; 37 and 40; 38 and 39; 38 and 40; and 39 and 40. The method of J in combination with elements 37 and 39; 37 and 40; 37 and 41; 39 and 40; 39 and 41; and 40 and 41.

Further embodiments disclosed herein include:

A1: Analyte sensors having a multi-component membrane. The analyte sensors comprise: a sensor tail configured for insertion into a tissue, the sensor tail comprising at least a working electrode; and first and second active areas disposed on the sensor tail, the first and second active areas comprising at least two different enzymes for measuring a concentration of at least one analyte; wherein the first active area is overcoated with a first membrane polymer and a second membrane polymer that differ from one another.

B1: Analyte sensors having a two active areas on a working electrode and configured for sensing different analytes. The analyte sensors comprise: a sensor tail configured for insertion into a tissue and comprising at least a working electrode; and at least two active areas disposed on the sensor tail, each active area comprising an enzyme, an electron transfer agent, and a polymer;

wherein the enzyme in each active area is different and responsive to different analytes; and wherein each active area has an oxidation-reduction potential, and the oxidation-reduction potential of a first active area is sufficiently separated from the oxidation-reduction potential of a second active area to allow production of a signal from the first active area independent of production of a signal from the second active area.

Embodiment A1 may have one or more of the following additional elements in any combination:

Element 1': wherein the first active area is overcoated with an admixture of the first membrane polymer and the second membrane polymer, and one of the first membrane polymer and the second membrane polymer overcoats the second active area as a homogenous membrane.

Element 2': wherein the first active area is overcoated with a bilayer membrane comprising the first membrane polymer disposed upon the second membrane polymer, and the second membrane polymer overcoats the second active area as a homogenous membrane.

Element 3': wherein the first active area comprises a first enzyme of the at least two different enzymes and the second active area comprises a second enzyme of the at least two different enzymes.

Element 4': wherein first enzyme is unreactive with the at least one analyte, and the first and second enzymes are capable of interacting in concert to generate a signal proportional to the concentration of the at least one analyte.

Element 5': wherein the second enzyme is capable of converting the at least one analyte into a product reactive with the first enzyme, such that the first enzyme is capable of reacting the product to generate a signal at the working electrode.

Element 6': wherein the first enzyme is xanthine oxidase and the second enzyme is glucose oxidase, at least one of the first active area and the second active area further comprising catalase.

Element 7': wherein the catalase is present in the first active area.

Element 8': wherein the first active area is disposed directly upon the working electrode and further comprises an electron transfer agent.

Element 9': wherein the first membrane polymer is disposed directly upon the first active area, the second active area is disposed directly upon the first membrane polymer, and the second membrane polymer is disposed directly upon the second active area.

Element 10': wherein the sensor tail comprises a first working electrode and a second working electrode, the first active area is disposed on a surface of the first working electrode, the second active area is disposed on a surface of the second working electrode, the first enzyme is reactive with a first analyte to generate a signal proportional to the concentration the first analyte, and the second enzyme is reactive with a second analyte to generate a signal proportional to the concentration the second analyte.

Element 11': wherein each of the first and second active areas has an oxidation-reduction potential, and the oxidation-reduction potential of the first active area is sufficiently separated from the oxidation-reduction potential of the second active area to allow production of a signal from the first active area independent of production of a signal from the second active area.

Element 12': wherein the oxidation-reduction potential of the first active area is separated from the oxidation-reduction potential of the second active area by at least about 100 mV.

Element 13': wherein the signal from the first active area corresponds to the first analyte concentration and the signal from the second active area corresponds to the second analyte concentration.

Element 14': wherein the first active area comprises a first electron transfer agent and the second active area comprises a second electron transfer agent different from the first electron transfer agent.

Embodiment B1 may have one or more of the following additional elements in any combination:

Element 15': wherein the oxidation-reduction potential of the first active area is separated from the oxidation-reduction potential of the second active area by at least about 100 mV.

Element 16': wherein the first active area comprises a first electron transfer agent and the second active area comprises a second electron transfer agent different from the first electron transfer agent.

Element 17': wherein the first and second active areas are overcoated with a mass transport limiting membrane, the first active area being overcoated with a single membrane polymer and the second active area being overcoated with two or more different membrane polymers.

To facilitate a better understanding of the embodiments described herein, the following examples of various representative embodiments are given. In no way should the following examples be read to limit, or to define, the scope of the invention.

EXAMPLES

Example 1: Detection of Glucose and Lactate Using an Analyte Sensor Having Two Different Active Areas on a Single Working Electrode. Two solutions containing different poly(vinylpyridine)-bound transition metal complexes were prepared. The structure of the polymer of the first solution is shown in Formula 1, and the structure of the polymer of the second solution is shown in Formula 2. Further details concerning these polymers is provided in commonly owned U.S. Pat. No. 6,605,200, which was incorporated by reference above. The subscripts for each monomer represent illustrative atomic ratios.

Formula 1

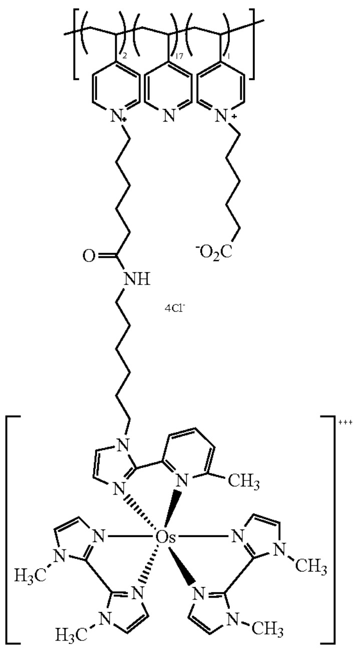

formula 2

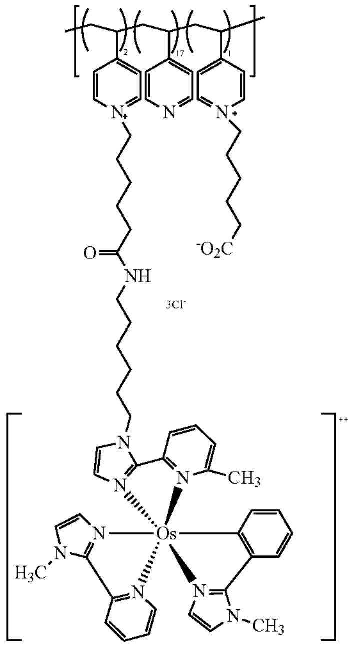

Figure 8:
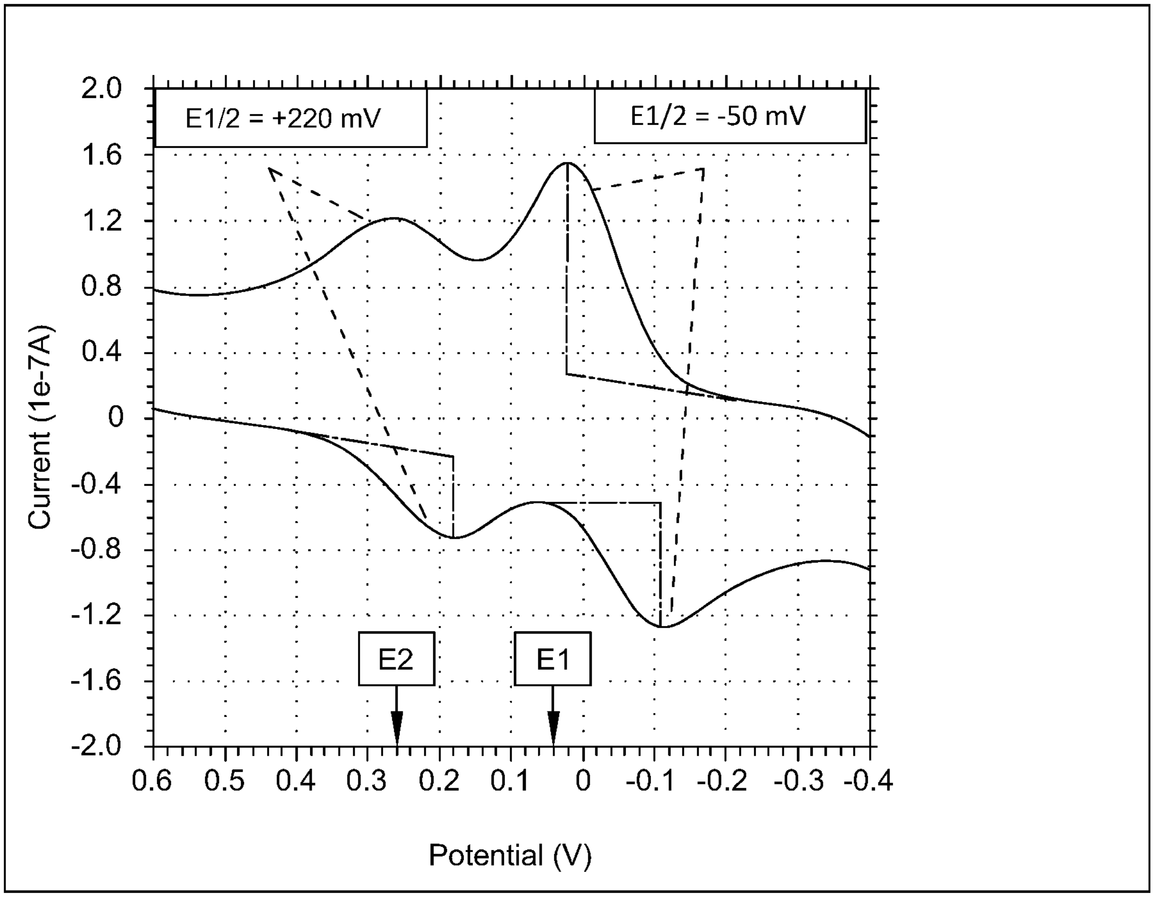
FIG. 8 shows an illustrative cyclic voltammogram obtained for an analyte-free buffer solution using a working electrode containing two different osmium complexes as electron transfer mediators.

The oxidation-reduction potential of the Formula 1 polymer with respect to an Ag/AgCl reference was −50 mV, and the oxidation-reduction potential of the Formula 2 polymer with respect to the same reference was +220 mV (270 mV separation, see FIG. 8). In addition to the transition metal complexes serving as respective electron transfer agents, the Formula 1 polymer included glucose oxidase (GOX) covalently bonded thereto, and the Formula 2 polymer included lactose oxidase (LOX) covalently bonded thereto following deposition on a working electrode and curing. Crosslinking was accomplished with polyethylene glycol diglycidyl ether (PEGDE400). Solutions containing the Formula 1 polymer and the Formula 2 polymer were formulated as specified in Tables 1 and 2 below.

TABLE 1

Glucose Oxidase (GOX) Formulation in 10 mM HEPES Buffer at pH = 8

| Component | Initial Concentration (mg/mL) | Added Volume (mL) | Final Concentration (mg/mL) |
|---|---|---|---|
| GOX | 40 | 0.41 | 16.4 |
| Formula 1 Polymer | 40 | 0.34 | 13.6 |
| PEGDE400 | 40 | 0.25 | 10 |

TABLE 2

Lactate Oxidase (LOX) Formulation in 10 mM MES Buffer at pH = 5.5

| Component | Initial Concentration (mg/mL) | Added Volume (μL) | Final Concentration (mg/mL) |
|---|---|---|---|
| LOX | 80 | 15 | 20 |
| Albumin | 80 | 10 | 13 |
| Formula 2 Polymer | 40 | 20 | 13 |
| PEGDE400 | 40 | 15 | 10 |

To deposit each active area, ~20 nL of each solution was deposited upon a carbon working electrode to form two discrete, separate spots each having an area of approximately 0.1 $mm^2$. One spot contained the glucose oxidase formulation and the other spot contained the lactose oxidase formulation. Following deposition, the working electrode was cured overnight at 25° C.

After curing, a membrane was deposited upon the working electrode. The membrane polymer was a polyvinylpyridine copolymer having amine-free polyether side chain functionalization, as described in U.S. Provisional Patent Application 62/684,438, filed on Jun. 13, 2018 and entitled “Temperature-Insensitive Membrane Materials and Analyte Sensors Containing the Same.” Membrane deposition was accomplished by dip coating the electrode three times in a solution containing 4 mL of the membrane polymer (120 mg/mL) and 0.35 mL PEG1000 (200 mg/mL). Spray coating, screen printing, or similar processes may be alternately used to deposit the membrane. Following deposition, the electrode was cured overnight at 25° C. and then further cured in a desiccated vial at 56° C. for two days.

After fabrication, the electrode was analyzed by cyclic voltammetry in a buffer solution containing neither glucose nor lactate. The resulting cyclic voltammogram is shown in FIG. 8, which shows the anodic and cathodic peaks characteristic of the two osmium complexes, since there was no current contribution from either glucose or lactate. The oxidation-reduction potentials reported above were calculated from the average of the cathodic and anodic peaks for each osmium complex.

To analyze for glucose and lactate, the electrode was placed at a potential above the average oxidation-reduction potential of the first polymer, specifically +40 mV (E1 in FIG. 8). At this potential, oxidation of the osmium complex in the first polymer and glucose may occur, but not oxidation of the osmium complex in the second polymer or lactate. To oxidize both osmium complexes and both glucose and lactate, the electrode was placed at a potential above the average oxidation-reduction potential of the second polymer, specifically +250 mV (E2 in FIG. 8).

Figure 9:
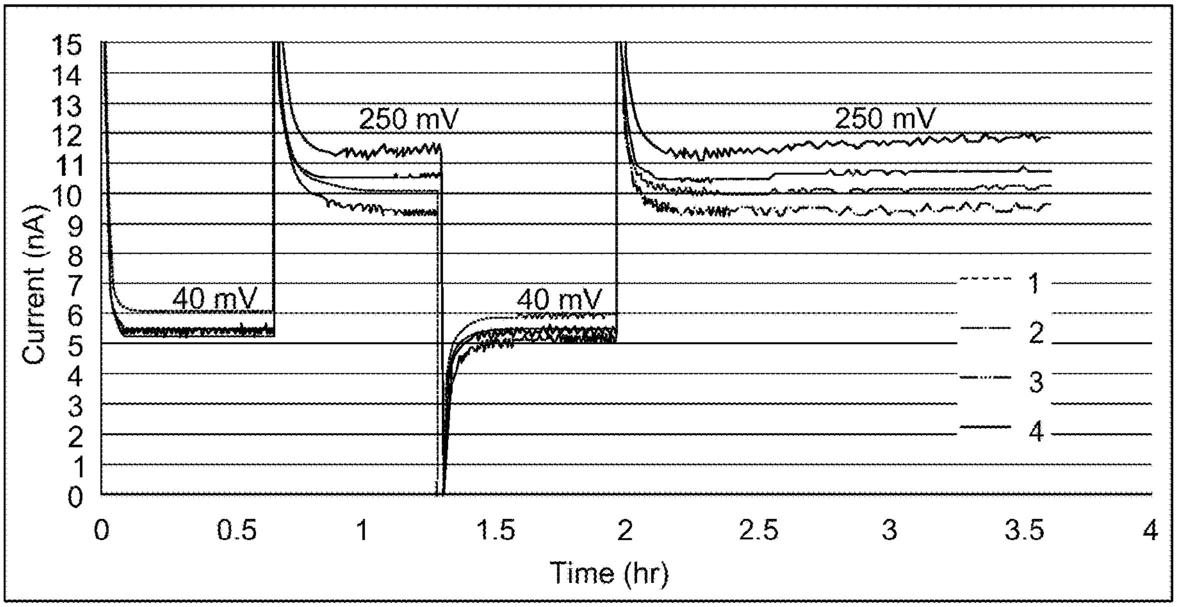
FIG. 9 shows four replicates of the electrode response in a 5 mM glucose/5 mM lactate buffer when cycling the electrode of FIG. 8 between the E1 and E2 potentials.

Glucose and lactate analyses were conducted by immersing the electrode in a buffer solution containing 5 mM glucose and 5 mM lactate, and the E1 and E2 potentials were successively applied. FIG. 9 shows four replicates of the electrode response in 5 mM glucose/5 mM lactate buffer when cycled between E1 and E2. As shown, the current at E1 was about 5 nA, which is due to glucose oxidation, and the current at E2 was about 10.5 nA, which is due to both glucose and lactate oxidation. Taking the difference between the measured currents at E1 and E2 provides a contribution of about 5.5 nA at E2 from lactate oxidation. Unknown glucose and lactate concentrations may be analyzed similarly by comparison to a lookup table or calibration curve.

Example 2A: Detection of Ethanol Using an Analyte Sensor Having Two Different Enzymes Operating In Concert on a Single Working Electrode (XOX/AOX). A spotting solution having the formulation shown in Table 3 was prepared. All of the components were dissolved in 10 mM HEPES buffer at pH 8. Crosslinking was accomplished with polyethylene glycol diglycidyl ether.

TABLE 3

Alcohol Oxidase and Xanthine Oxidase Solution

| Component | Concentration (mg/mL) |
|---|---|
| XOX | 16 |
| AOX | 64 |
| Catalase | 4 |
| PVI (pH = 5.8) | 16 |
| Os complex | 10 |
| PEGDE400 | 10 |

~15 nL of the solution was deposited on a carbon working electrode as a single spot having an area of approximately 0.05 $mm^2$. Following deposition, the working electrode was cured overnight at 25° C.

After curing, a poly(4-vinylpyridine) (PVP) membrane was deposited upon the working electrode from a coating solution containing 100 mg/mL PVP and 100 mg/mL PEGDE400. Membrane deposition was accomplished by dip coating the electrode three times in the coating solution. Following deposition, the electrode was cured overnight at 25° C. and then further cured in desiccated vials at 56° C. for two days. Spray coating, screen printing, or similar processes may be alternately used to deposit the membrane.

Figure 10:
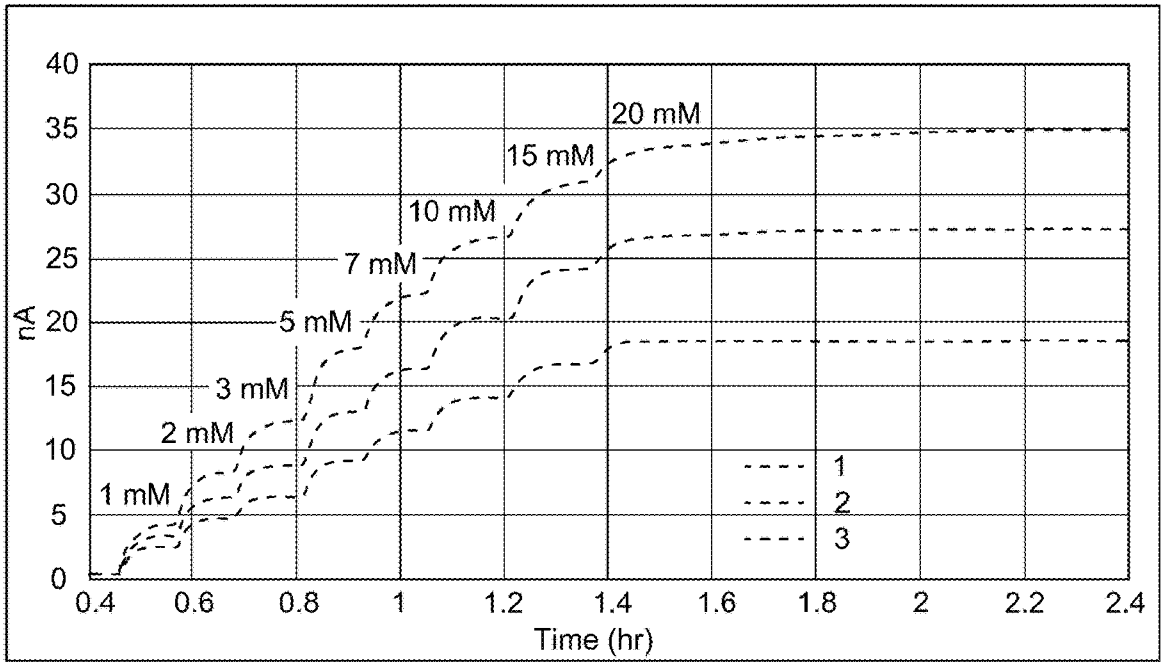
FIG. 10 shows three replicates of the response for an electrode containing alcohol oxidase and xanthine oxidase together in an active area upon exposure to varying ethanol concentrations.
Figure 11A:
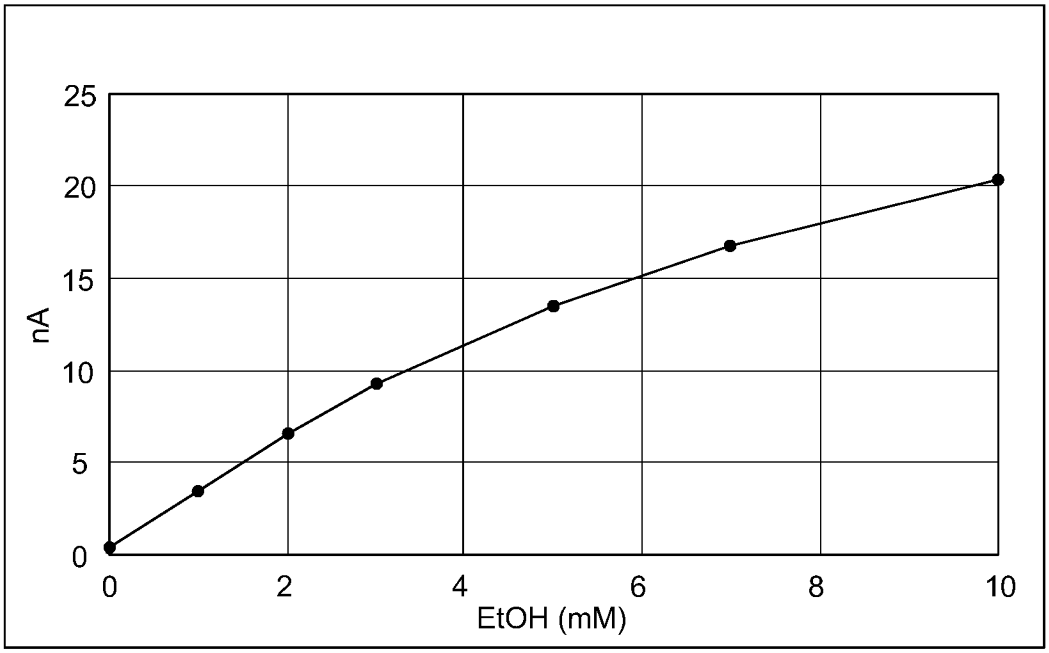
FIG. 11A shows an illustrative plot of average current response versus ethanol concentration for the electrodes of FIG. 10.
Figure 11B:
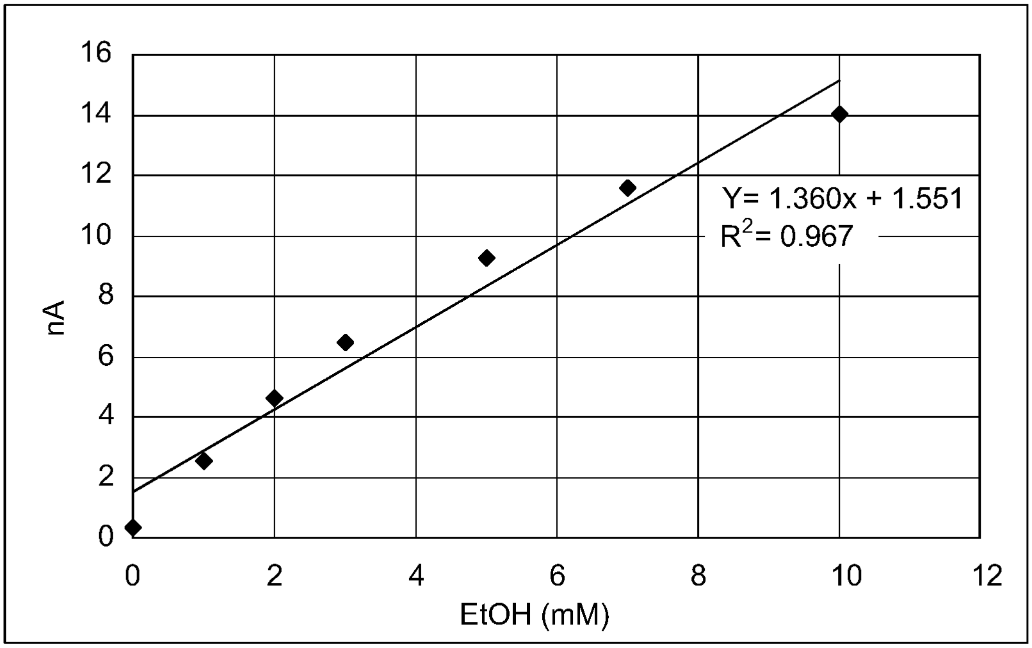
FIG. 11B shows an illustrative plot of current response versus ethanol concentration for a single electrode.

Ethanol analyses were conducted by immersing the electrode in ethanol-containing PBS solutions each containing varying concentrations of ethanol. FIG. 10 shows three replicates of the response for an electrode containing alcohol oxidase and xanthine oxidase together in a sensing spot upon exposure to varying ethanol concentrations. As shown, the current response increased over the course of several minutes following exposure to a new ethanol concentration before stabilizing thereafter. FIG. 11A shows an illustrative plot of average current response versus ethanol concentration. FIG. 11B shows corresponding data for a single sensor. As shown, the sensor response was approximately linear over an ethanol concentration range of 0-10 mM.

Example 2B: Detection of Ethanol Using an Analyte Sensor Having Two Different Enzymes Operating In Concert on a Single Working Electrode (XOX/GOX). A first spotting solution having the formulation shown in Table 4 was prepared. All of the components were dissolved in 10 mM HEPES buffer at pH 8. Crosslinking was accomplished with polyethylene glycol diglycidyl ether.

TABLE 4

Xanthine Oxidase Solution

| Component | Concentration (mg/mL) |
|---|---|
| XOX | 25 |
| Catalase | 12 |
| PVI (pH = 5.8) | 12 |
| Os complex | 8 |
| PEGDE400 | 6 |

~15 nL of the first spotting solution was deposited on a carbon working electrode as a single spot (XOX spot) having an area of approximately 0.05 $mm^2$. Following deposition, the working electrode was cured overnight at 25° C.

After curing, a poly(4-vinylpyridine) (PVP) membrane was deposited upon the working electrode and the XOX spot from a coating solution containing 100 mg/mL PVP and 100 mg/mL PEGDE400. Membrane deposition was accomplished by dip coating the electrode three times in the coating solution. Spray coating, screen printing, or similar processes may be alternately used to deposit the membrane. Following deposition, the electrode was cured overnight at 25° C. and then further cured in desiccated vials at 56° C. for two days.

A second spotting solution having the formulation shown in Table 5 was prepared. All of the components were dissolved in 10 mM HEPES buffer at pH 8. Crosslinking was accomplished with polyethylene glycol diglycidyl ether.

TABLE 5

Glucose Oxidase Solution

| Component | Concentration (mg/mL) |
|---|---|
| GOX | 16 |
| Catalase | 32 |
| PVI (pH = 5.8) | 32 |
| PEGDE400 | 6 |

~15 nL of the second spotting solution was deposited on the PVP membrane from above as a single spot (GOX spot) having an area of approximately 0.05 $mm^2$. Following deposition, curing was performed overnight at 25° C.

After curing, a second membrane was deposited upon the GOX spot and the PVP membrane. The membrane polymer in this case was a crosslinked polyvinylpyridine-co-styrene polymer, in which a portion of the pyridine nitrogen atoms were functionalized with a non-crosslinked poly(ethylene glycol) tail and a portion of the pyridine nitrogen atoms were functionalized with an alkylsulfonic acid group. The membrane at this location was deposited from a coating solution comprising 35 mg/mL of the crosslinked polyvinylpyridine-co-styrene polymer and 100 mg/mL PEGDE400. Membrane deposition was accomplished by dip coating the electrode three times in the coating solution. Spray coating, screen printing, or similar processes may be alternately used to deposit the membrane. Following deposition, the electrode was cured overnight at 25° C. and then further cured in desiccated vials at 56° C. for two days.

Figure 12A:
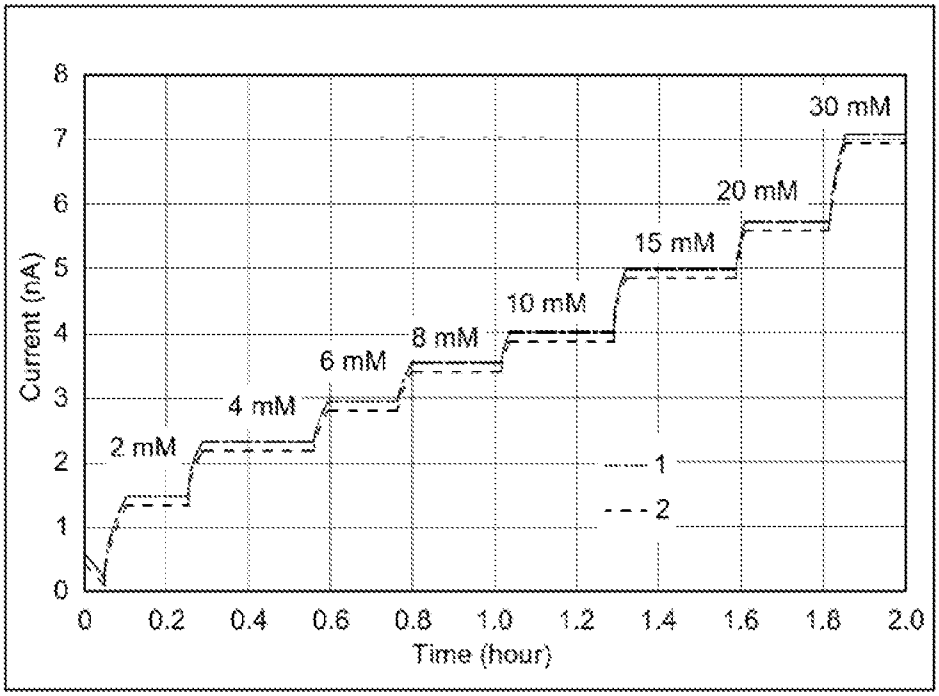
FIG. 12A shows two replicates of the response for an electrode containing glucose oxidase and xanthine oxidase layered in separate active areas and spaced apart by a membrane upon exposure to varying ethanol concentrations, in which catalase is present in the active area containing glucose oxidase.
Figure 13:
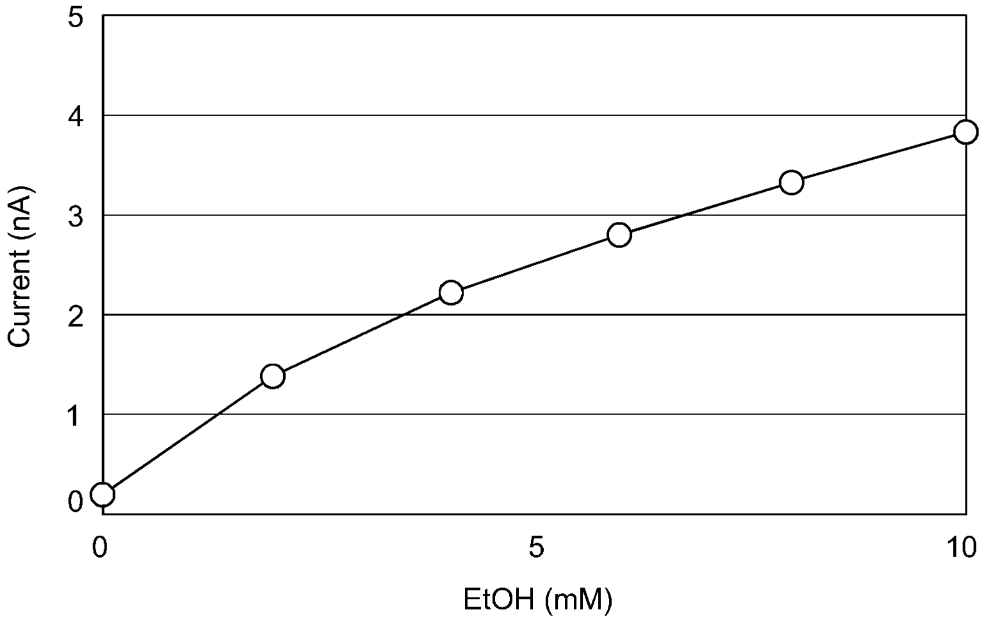
FIG. 13 shows an illustrative plot of average current response versus ethanol concentration for the electrodes of FIG. 12A.

Ethanol analyses were conducted by immersing the electrode in ethanol-containing PBS solutions each containing varying concentrations of ethanol. FIG. 12A shows two replicates of the response for an electrode containing glucose oxidase and xanthine oxidase layered in separate active areas and spaced apart by a membrane upon exposure to varying ethanol concentrations, in which catalase is in the active area with the glucose oxidase. As shown, the current response increased over the course of several minutes following exposure to a new ethanol concentration before stabilizing thereafter. Good reproducibility been the two replicates was observed. FIG. 13 shows an illustrative plot of average current response versus ethanol concentration. The curve shape was similar to that obtained using AOX/XOX (FIG. 11A, Example 2A).

Figure 12B:
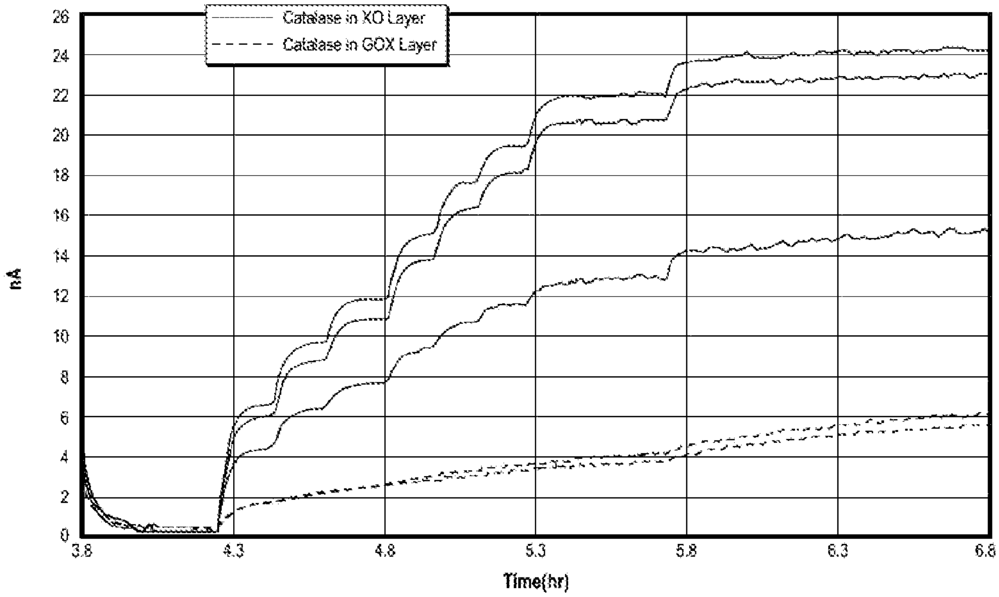
FIG. 12B shows comparative response data between an electrode containing glucose oxidase and xanthine oxidase layered in separate active areas and spaced apart by a membrane upon exposure to varying ethanol concentrations, in which catalase is present in the active areas separately.

FIG. 12B shows comparative response data between an electrode containing glucose oxidase and xanthine oxidase layered in separate active areas and spaced apart by a membrane upon exposure to varying ethanol concentrations, in which catalase is present in the active areas separately. As shown, the sensor response was greater when the catalase was included in the active area containing xanthine oxidase.

Example 3: Comparative Analyte Sensor Response Toward Lactate in the Presence of Various Mass Transport Limiting Membranes. For this example, the membrane formulations below were coated onto a carbon working electrode containing lactate oxidase in an active area thereof. The active area was deposited using the lactate oxidase formulation as described in Example 1, except substituting Formula 1 Polymer for Formula 2 Polymer in the formulation and adjusting the concentrations to those specified in Table 6 below.

TABLE 6

Lactate Oxidase (LOX) in 10 mM MES Buffer at pH = 5.5

| Component | Concentration (mg/mL) |
|---|---|
| LOX | 24.6 |
| Albumin | 24.6 |
| Formula 1 Polymer | 9.2 |
| PEGDGE400 | 6.2 |

Active area deposition and curing was performed as described in Example 1, except for depositing six spots each having an area of 0.01 $mm^2$ instead of the single spot having an area of 0.1 $mm^2$ in Example 1. Unless otherwise indicated below, membrane deposition was performed by dip coating (1-5 dips of the electrode and a wait time of about 10 minutes between dips). Following the completion of dip coating, the membranes were cured for 24 hours at 25° C., followed by 48 hours at 56° C. in desiccated vials.

Electrode response was measured by placing the active area of the electrode in a beaker containing 100 mM pH=7.5 phosphate buffered saline at 37° C. The potential was raised to +40 mV versus Ag/AgCl, and the current was monitored continuously thereafter. To determine the response at various lactate concentrations, sodium lactate was added to the buffer solution in increments of 1 mM up to 5 mM. To determine the response stability, the current was measured in 5 mM sodium lactate over an extended period, such as two weeks.

Membrane Polymers 1A and 1B: The first tested membrane polymer was a crosslinked polyvinylpyridine-co-styrene polymer, in which a portion of the pyridine nitrogen atoms were functionalized with a non-crosslinked poly(ethylene glycol) tail and a portion of the pyridine nitrogen atoms were functionalized with an alkylsulfonic acid group. Two different crosslinking agents were used to affect crosslinking of this membrane polymer: glycerol triglycidyl ether (Gly3-Formulation 1)) and polyethylene glycol diglycidyl ether 400 (PEGDGE400-Formulation 2). Formulation 1 contained 4 mL of the membrane polymer in 80:20 ethanol:HEPES buffer (140 mg/ml), 1 ml of Gly3 in 80:20 ethanol:HEPES buffer (35 mg/mL), and 0.0132 mL of aminopropyl-terminated polydimethylsiloxane (PDMS) in ethanol (100 mg/mL). Formulation 2 contained 4 mL of the membrane polymer in 80:20 ethanol:HEPES buffer (140 mg/mL), 0.2 mL of PEGDGE400 in 80:20 ethanol:HEPES buffer (100 mg/mL), and 0.0132 mL of aminopropyl-terminated polydimethylsiloxane (PDMS) in ethanol (100 mg/mL). The corresponding crosslinked polymers are designated as Polymers 1A and 1B, respectively, herein.

Figure 14:
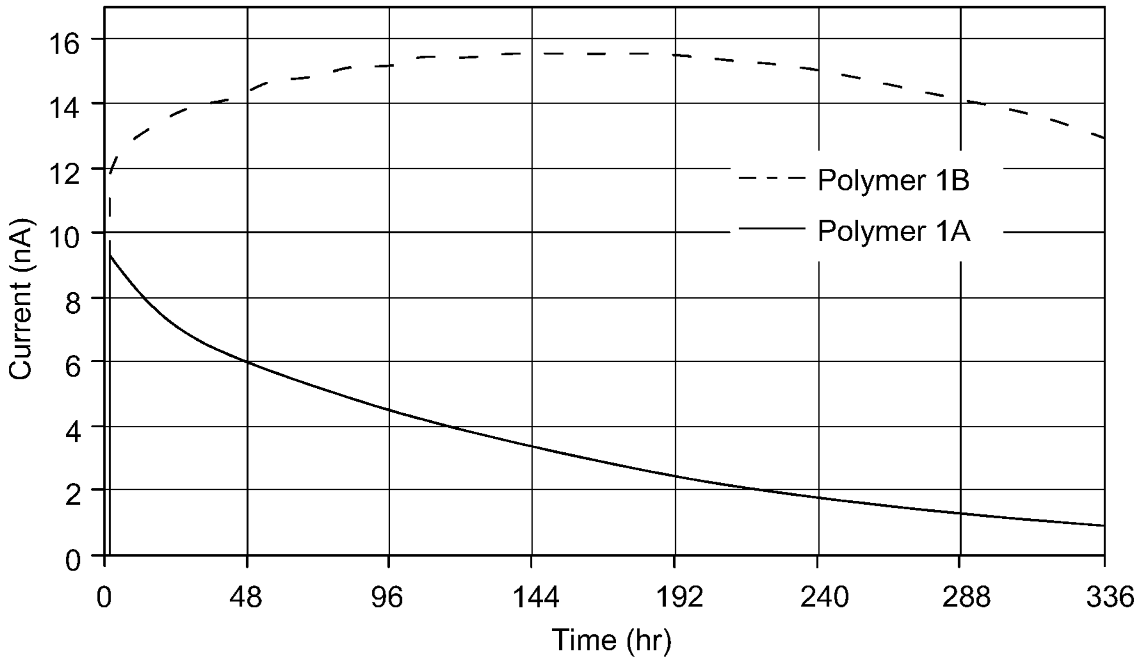
FIG. 14 shows an illustrative plot of the response of an electrode overcoated with Polymers 1A and 1B to a 5 mM lactate solution.

FIG. 14 shows an illustrative plot of the response of an electrode overcoated with Polymers 1A and 1B to a 5 mM lactate solution. As shown, neither formulation afforded a stable sensor response over time. The sensor current afforded by Polymer 1A (Formulation 1) decreased slowly over a two-week measurement time, whereas the sensor current afforded by Polymer 1B (Formulation 2) initially increased over the first week of lactate exposure and then decreased. In contrast, both of these membranes provided a stable response in the presence of glucose analyte (data not shown).

Membrane Polymer 2: The second tested membrane polymer was polyvinylpyridine (PVP) crosslinked with polyethylene glycol diglycidyl ether 1000 (PEGDGE1000). This membrane polymer is designated as Polymer 2 herein. The membrane formulation (Formulation 3) contained 4.3 mL of PVP in 80:20 ethanol:HEPES buffer (100 mg/ml), 0.25 mL of PEGDGE1000 in 80:20 ethanol:HEPES buffer (200 mg/mL), and 0.0132 mL of PDMS in ethanol (100 mg/ml).

Figure 15:
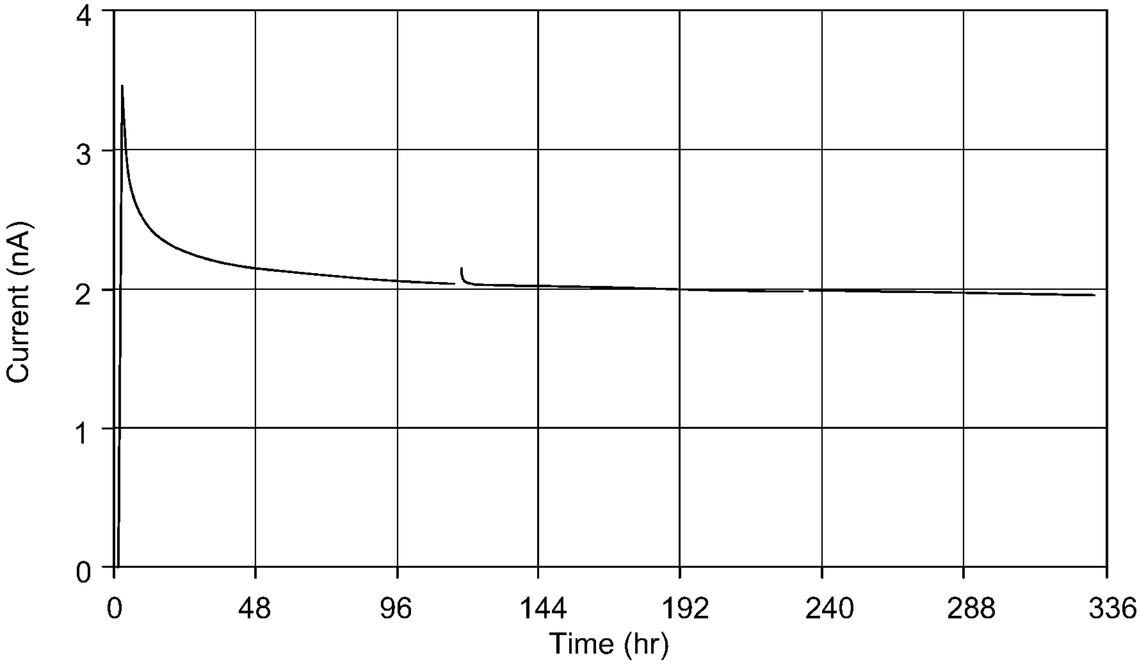
FIG. 15 shows an illustrative plot of the response of an electrode overcoated with Polymer 2 to a 5 mM lactate solution.

FIG. 15 shows an illustrative plot of the response of an electrode overcoated with Polymer 2 (Formulation 3) to a 5 mM lactate solution. Like Polymers 1A and 1B, Polymer 2 also did not afford a stable current response over time. There was a large decrease in response over the first 48 hours, followed by relatively stable performance thereafter. In addition, the sensitivity was well below a target value of about 1 nA/mM. Like Polymers 1A and 1B, Polymer 2 provided a stable current response in the presence of glucose analyte (data not shown).

Membrane Polymer 3: The third tested membrane polymer was polyvinylpyridine (PVP) crosslinked with PEGDGE400. This membrane polymer is designated as Polymer 3 herein. The membrane formulation (Formulation 4) contained 4.3 mL of PVP in 80:20 ethanol:HEPES buffer (100 mg/mL), 0.23 ml of PEGDGE400 in 80:20 ethanol:HEPES buffer (100 mg/mL), and 0.0132 mL of PDMS in ethanol (100 mg/mL).

Figure 16:
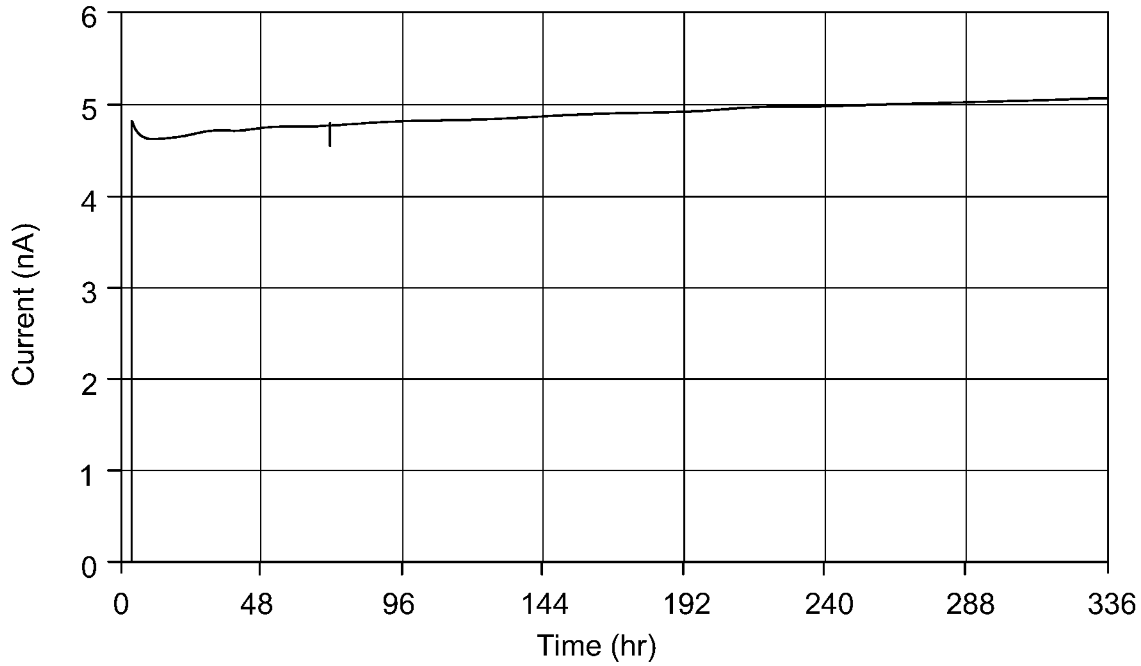
FIG. 16 shows an illustrative plot of the response of an electrode overcoated with Polymer 3 to a 5 mM lactate solution.
Figure 17:
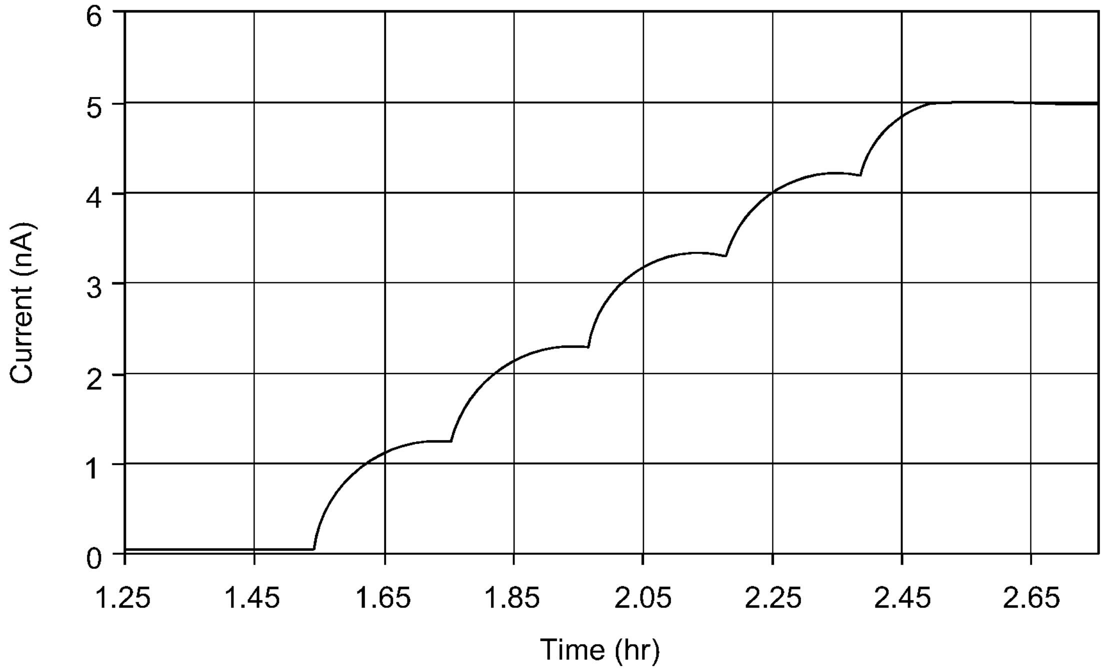
FIG. 17 shows an illustrative plot of the response of an electrode overcoated with Polymer 3 to lactate solutions having varying lactate concentrations.

FIG. 16 shows an illustrative plot of the response of an electrode overcoated with Polymer 3 (Formulation 4) to a 5 mM lactate solution. Unlike Polymer 2, which was crosslinked with a higher molecular weight variant of the same crosslinking agent, Polymer 3 surprisingly afforded a stable current response over time. Moreover, the current responded rapidly and achieved a stable current as increasing amounts of lactate were added in 1 mM increments (FIG. 17).

Membrane Polymer 4: The fourth tested membrane polymer was PVP containing 3-4 wt. % non-crosslinked PEG side chains, which was then crosslinked with PEGDGE1000. Thus, the tested membrane polymer contained both non-crosslinked PEG chains and crosslinking PEG1000 chains. This membrane polymer is designated as Polymer 4 herein. The membrane formulation (Formulation 5) contained 4.3 mL of the polymer in 80:20 ethanol:HEPES buffer (100 mg/mL), 0.025 mL of PEGDGE1000 in 80:20 ethanol:HEPES buffer (200 mg/mL), and 0.0132 mL of PDMS in ethanol (100 mg/mL).

Figure 18:
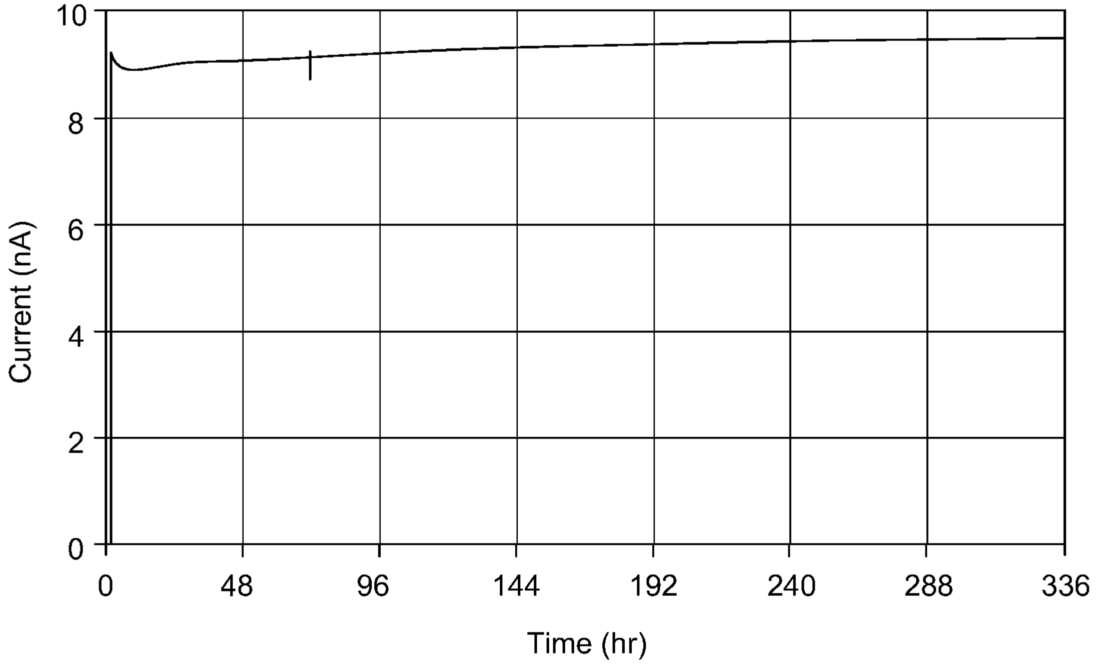
FIG. 18 shows an illustrative plot of the response of an electrode overcoated with Polymer 4 to a 5 mM lactate solution.
Figure 19:
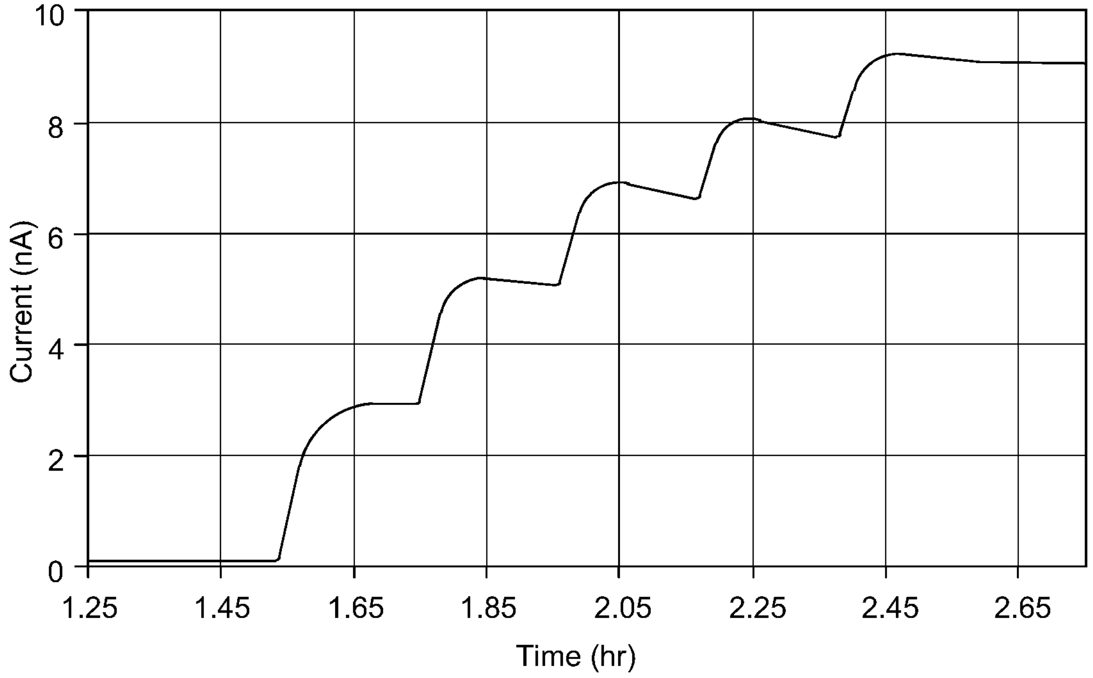
FIG. 19 shows an illustrative plot of the response of an electrode overcoated with Polymer 4 to lactate solutions having varying lactate concentrations.

FIG. 18 shows an illustrative plot of the response of an electrode overcoated with Polymer 4 (Formulation 5) to a 5 mM lactate solution. Unlike Polymers 2 and 3, Polymer 4 surprisingly afforded a stable current response over time. Moreover, the current responded rapidly and achieved a stable value as increasing amounts of lactate were added in 1 mM increments (FIG. 19).

Bilayer Membranes Comprising Polymers 2 and 1B or Polymers 2 and 1A: Formulation 3 (Polymer 2) was coated onto the electrode surface by repeated dip coating operations. Spray coating, screen printing, or similar processes may be alternately used to deposit the membrane. Formulation 2 (Polymer 1B) was then coated onto the deposited crosslinked PVP layer by repeated dip coating operations. There was a 10 minute wait time between successive dips. After all dipping operations were complete, the sensors were cured at 25° C. for 24 hours, followed by 48 hours at 56° C. in desiccated vials. As shown above, neither of these membrane polymers provided satisfactory performance when used alone.

Figure 20:
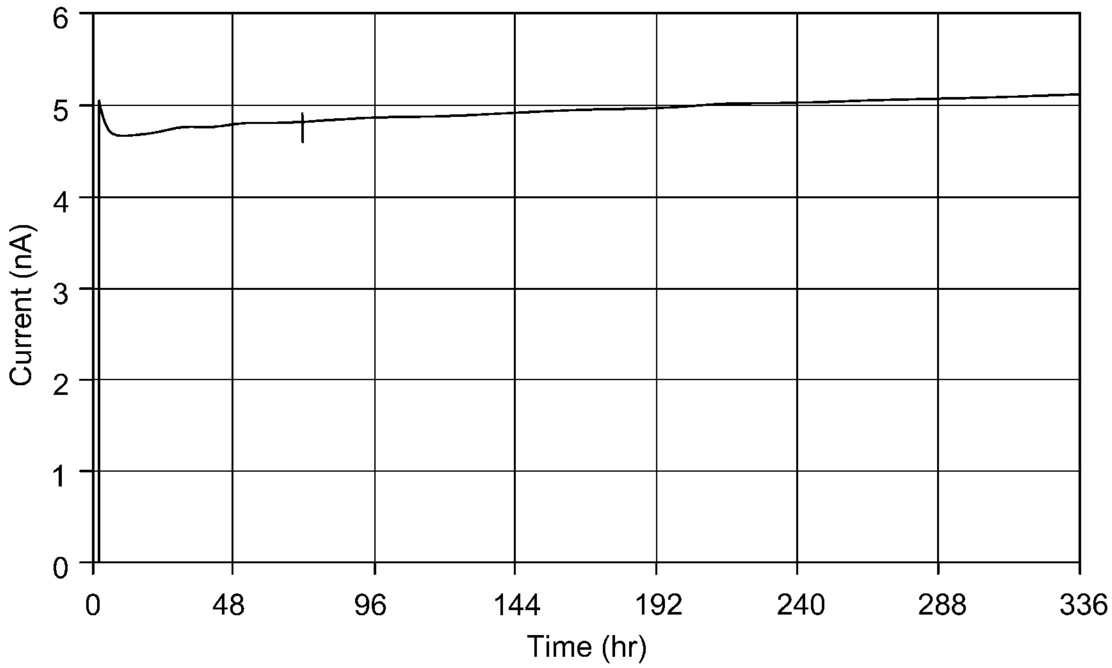
FIG. 20 shows an illustrative plot of the response of an electrode overcoated with a bilayer membrane comprising a lower layer of crosslinked PVP (Polymer 2) and an upper layer of crosslinked Polymer 1B to a 5 mM lactate solution.

FIG. 20 shows an illustrative plot of the response of an electrode overcoated with a bilayer membrane comprising a lower layer of crosslinked PVP (Polymer 2) and an upper layer of crosslinked Polymer 1B to a 5 mM lactate solution. Unlike either Polymer 1B or PVP crosslinked with the same crosslinking agent (Polymer 2), a bilayer membrane comprising these membrane polymers surprisingly afforded a stable current response over time at an acceptable level of sensitivity, even though neither polymer provided acceptable performance alone. The response data in FIG. 20 was for an electrode dipped twice in Formulation 3 (Polymer 2) and four times in Formulation 2 (Polymer 1B).

The amount (thickness) of each membrane polymer in the bilayer membrane may vary the sensor performance, as shown hereinafter for Polymer 2 and Polymer 1A. Thus, the Gly3-crosslinked variant of Polymer 1B (i.e., Polymer 1A) may similarly provide acceptable performance when combined in a bilayer membrane with Polymer 2, even though neither polymer provided acceptable performance alone.

Figure 21:
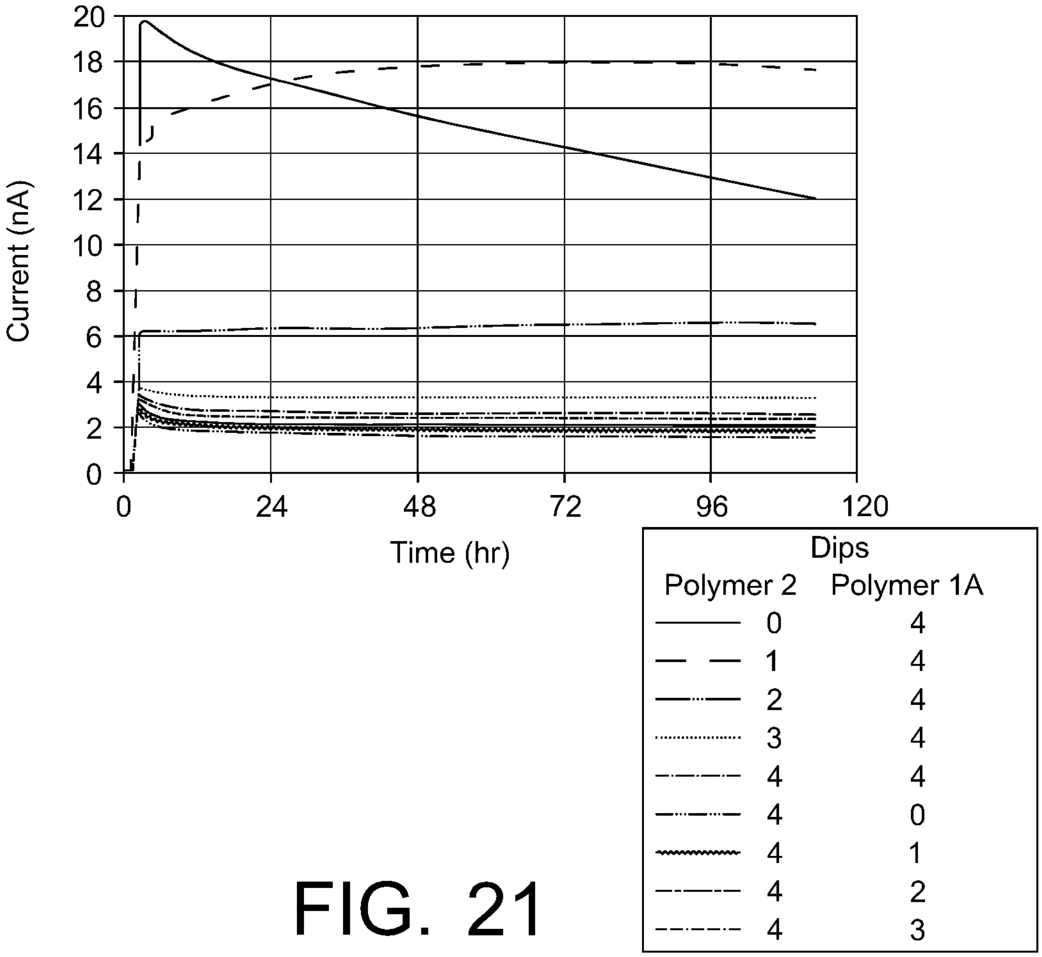
FIG. 21 shows an illustrative plot of the response of an electrode overcoated with a bilayer membrane comprising a lower layer of crosslinked PVP (Polymer 2) and an upper layer of crosslinked Polymer 1A to a 5 mM lactate solution, in which the electrode was dip coated a variable number of times with Formulation 1 and Formulation 3.

FIG. 21 shows an illustrative plot of the response of an electrode overcoated with a bilayer membrane comprising a lower layer of crosslinked PVP (Polymer 2) and an upper layer of crosslinked Polymer 1A to a 5 mM lactate solution, in which the electrode was dip coated a variable number of times with Formulation 1 (Polymer 1A) and Formulation 3 (Polymer 2). The crosslinker for PVP (Polymer 2) in this case remained PEGDGE1000, but the crosslinker for Polymer 1A was Gly3, which shows that this crosslinker can also be suitable for use in a bilayer membrane configuration. As shown in FIG. 21, dip coating the electrode twice in Formulation 3 and four times in Formulation 1 afforded a good balance of sensitivity and a stable current response. Altering the number of dip coating operations changed the thickness of each component of the bilayer membrane, as well as the mass ratio of the membrane polymers to each other. As shown in FIG. 21, if the PVP layer is too thin (0 or 1 Polymer 2 dips), the sensitivity is high but the response stability is poor, whereas if it is too thick (3 or more dips), the electrode exhibits low sensitivity and poor response stability in some cases.

Admixed Membrane Comprising Membrane Polymers 1B and 3: A combined membrane formulation (Formulation 6) was prepared by mixing 1.5 mL of PVP in 80:20 ethanol:HEPES buffer (100 mg/mL), 2.5 mL of the copolymer used to prepare Formulations 1A and 1B in 80:20 ethanol:HEPES buffer (140 mg/mL), 0.175 mL of PEGDGE400 in 80:20 ethanol:HEPES buffer (100 mg/mL), and 0.0132 mL of PDMS in ethanol (100 mg/mL). Thus, after crosslinking Formulation 6 contained Polymer 1B and Polymer 3, each of which is crosslinked with PEG400.

Figure 22:
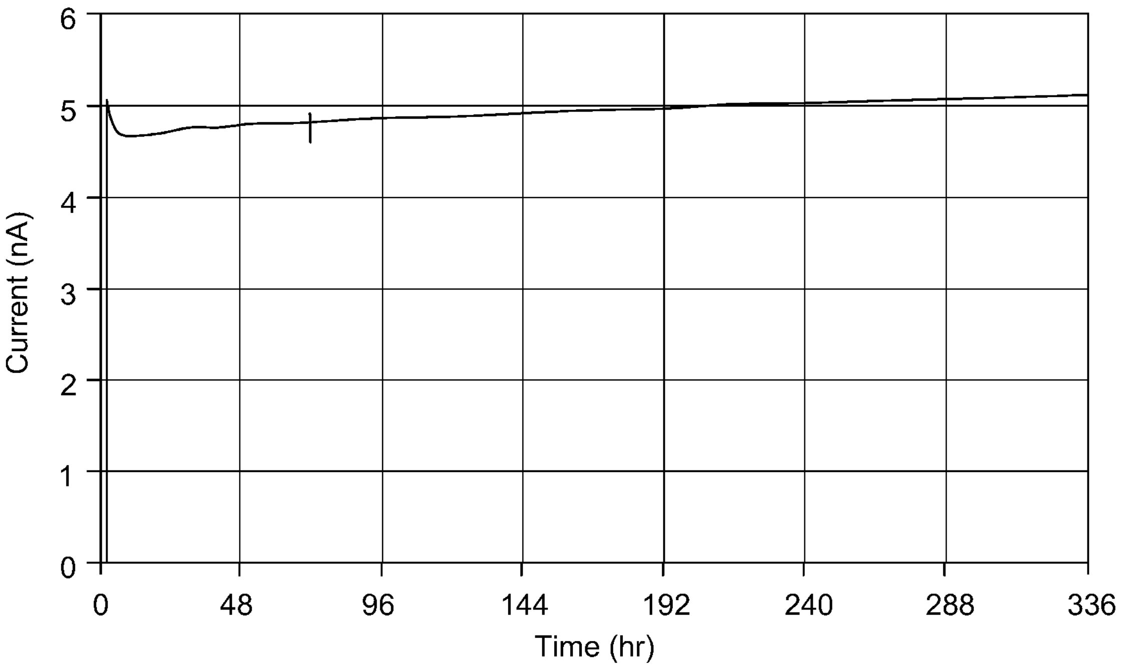
FIG. 22 shows an illustrative plot of the response of an electrode overcoated with an admixed membrane comprising crosslinked PVP (Polymer 2) and crosslinked Polymer 1B to a 5 mM lactate solution.
Figure 23:
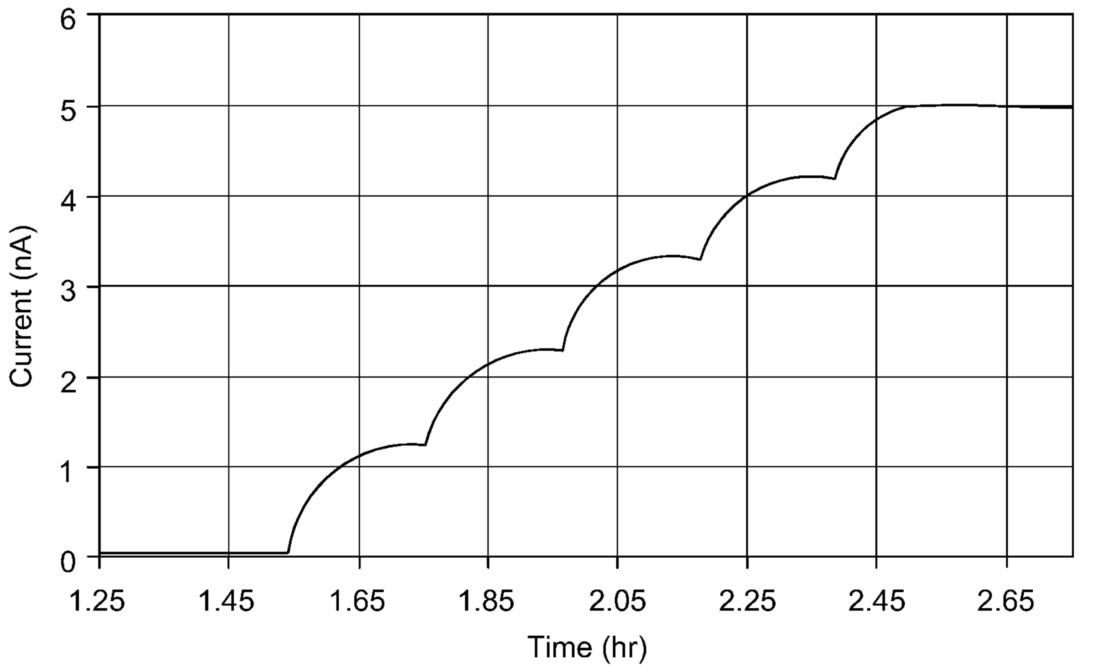
FIG. 23 shows an illustrative plot of the response of an electrode overcoated with an admixed membrane comprising crosslinked PVP (Polymer 2) and crosslinked Polymer 1B to varying lactate concentrations.

FIG. 22 shows an illustrative plot of the response of an electrode overcoated with an admixed membrane comprising crosslinked PVP (Polymer 3) and crosslinked Polymer 1B to a 5 mM lactate solution. Like a bilayer membrane containing one of the same components (Polymer 1B), the admixed membrane afforded a stable current response over time and an acceptable level of sensitivity. Moreover, the current responded rapidly and achieved a stable value as increasing amounts of lactate were added in 1 mM increments (FIG. 23).

Figure 24:
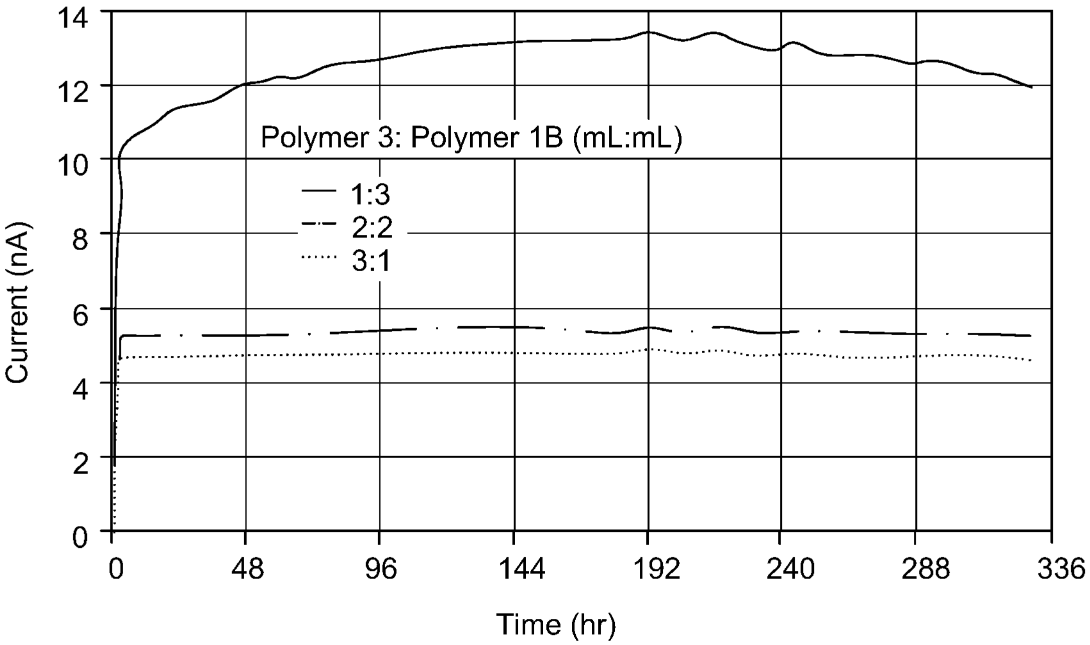
FIG. 24 shows an illustrative plot of the response an electrode overcoated with an admixed membrane comprising various ratios of crosslinked PVP (Polymer 2) and crosslinked Polymer 1B.

FIG. 24 shows an illustrative plot of the response a sensor overcoated with an admixed membrane comprising various ratios of crosslinked PVP (Polymer 3) and crosslinked Polymer 1B. As shown in FIG. 24, higher amounts of Polymer 1B increased the sensitivity but afforded poorer response stability.

Example 4: Performance of a Sensor Comprising Two Working Electrodes Overcoated with a Bilayer Mass Transport Limiting Membrane. For this example, a first working electrode containing glucose oxidase and a second working electrode containing lactate oxidase were overcoated with a bilayer membrane. The active area containing glucose oxidase was deposited using the glucose oxidase formulation as described in Example 1 (Table 1). The active area containing lactate oxidase was deposited using the lactate oxidase formulation as described in Example 3 (Table 6). Active area deposition and curing was performed as described in Example 1, except for depositing five spots each having an area of 0.01 $mm^2$ instead of the single spot having an area of 0.1 $mm^2$ in Example 1. Membrane polymer formulations corresponding to Formulation 2 (Polymer 1B) and Formulation 4 (Polymer 3) from Example 3 were employed for depositing the bilayer membrane in this example. Namely, Polymer 3 was deposited upon the second working electrode featuring lactate oxidase. Selective deposition upon the second working electrode was accomplished by a modified slot coating procedure. Curing was then performed for 24 hours at 25° C. Thereafter, the entire assembly (i.e., both working electrodes, the PVP coating upon the second working electrode, and the counter and reference electrodes) was dip coated in Formulation 2. Curing was again performed for 24 hours at 25° C., followed by baking at 56° C. in a desiccated environment for 48 hours. Thus, a homogeneous membrane was deposited upon the first working electrode (glucose-responsive) and a bilayer membrane was deposited upon the second working electrode (lactate-responsive). The crosslinked PVP (Polymer 3) was in contact with the lactate-responsive active area upon the second working electrode.

Figure 25:
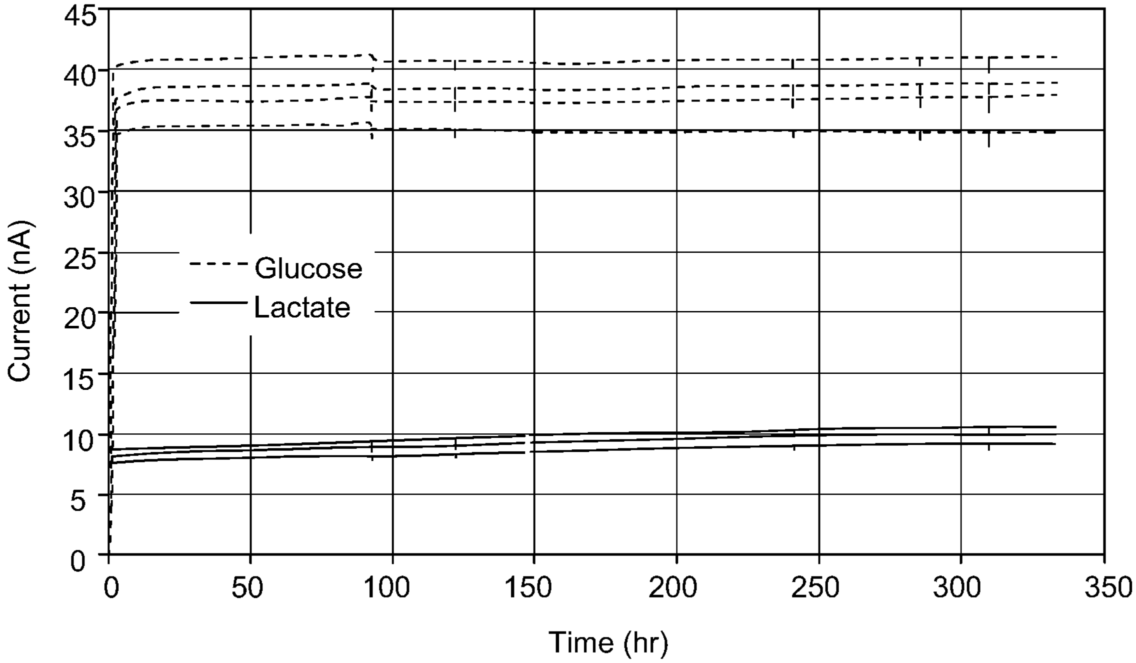
FIG. 25 shows an illustrative plot of the response of a sensor containing two working electrodes to a 30 mM glucose/5 mM lactate solution, in which the lactate-responsive working electrode is overcoated with a bilayer membrane and the glucose-responsive working electrode is overcoated with a homogeneous membrane.

The sensor was used to assay for glucose and lactate simultaneously in 100 mM PBS at 37° C. In a first experiment, the sensor was exposed for 2 weeks at 37° C. to a 100 mM PBS solution containing 30 mM glucose and 5 mM lactate. The sensor was held at +40 mV relative to Ag/AgCl for this test. FIG. 25 shows an illustrative plot of the sensor response for each working electrode upon exposure to 30 mM glucose and 5 mM lactate. As shown, the sensor response remained very steady over the observation period.

Figure 26:
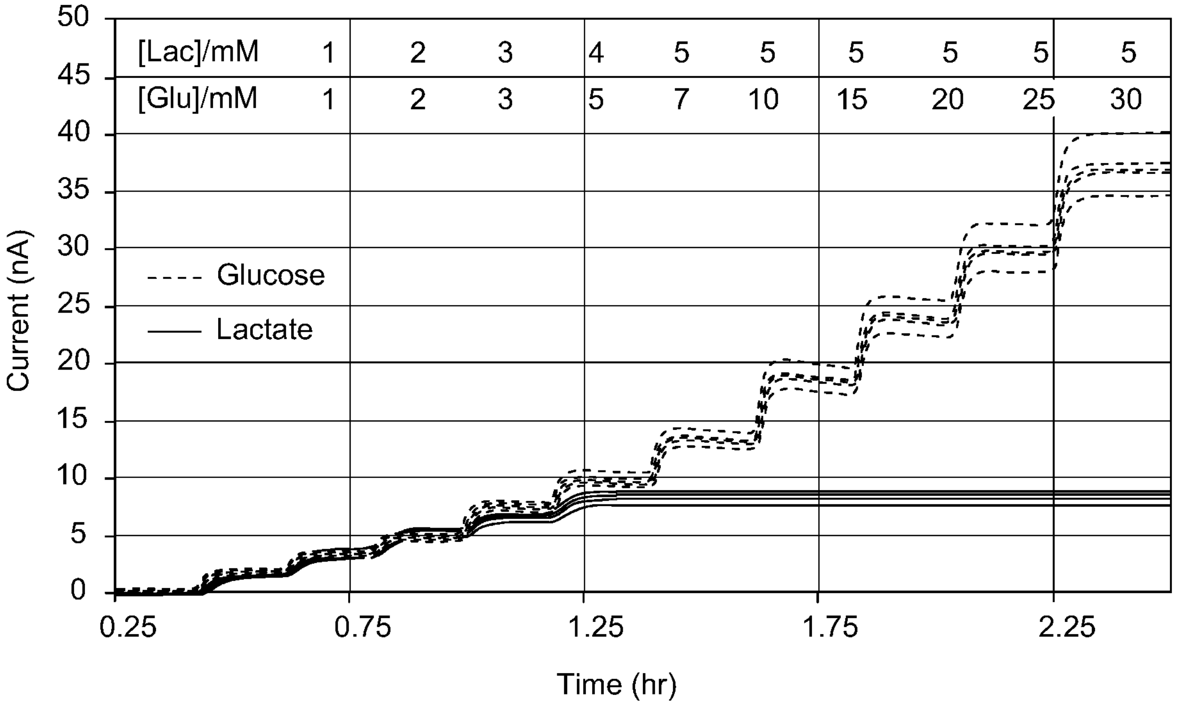
FIG. 26 shows an illustrative plot of the response of a sensor containing two working electrodes to solutions containing varying concentrations of glucose and lactate, in which the lactate-responsive working electrode is overcoated with a bilayer membrane and the glucose-responsive working electrode is overcoated with a homogeneous membrane.

Next, glucose and lactate were added incrementally to 100 mM PBS at 37° C. to determine the responsiveness of the sensor toward each analyte. The sensor was again held at +40 mV relative to Ag/AgCl for this test. Glucose was added over a concentration range of 0-30 mM, and lactate was added over a concentration range of 0-5 mM. FIG. 26 shows an illustrative plot of the sensor response to varying concentrations of glucose and lactate. As shown in FIG. 26, the sensor response was rapid for both analytes and remained stable at a given analyte concentration.

Example 5: Detection of Ketones Using an Analyte Sensor Having In Concert Interacting Diaphorase and β-Hydroxybutyrate Dehydrogenase. For this example, the membrane formulation shown in Table 7 below was coated onto a carbon working electrode. Deposition was performed to place six spots, each having an area of around 0.01 $mm^2$, upon the working electrode. Following deposition, the working electrode was cured overnight at 25° C. Thereafter, a PVP membrane was applied to the working electrode via dip coating using a coating solution formulated with 4 mL of 100 mg/mL PVP, 0.2 mL of 100 mg/mL PEGDGE400, and 0.0132 mL of 100 mg/mL PDMS. Membrane curing was performed for 24 hours at 25° C., followed by 48 hours at 56° C. in desiccated vials.

TABLE 7

β-Hydroxybutyrate Dehydrogenase (HBDH) in 10 mM MES Buffer at pH = 5.5

| Component | Concentration (mg/mL) |
|---|---|
| HBDH | 8 |
| Diaphorase | 4 |
| Albumin | 8 |
| $NAD^+$ | 8 |
| Formula 1 Polymer | 8 |
| PEGDGE400 | 4 |

Figure 27:
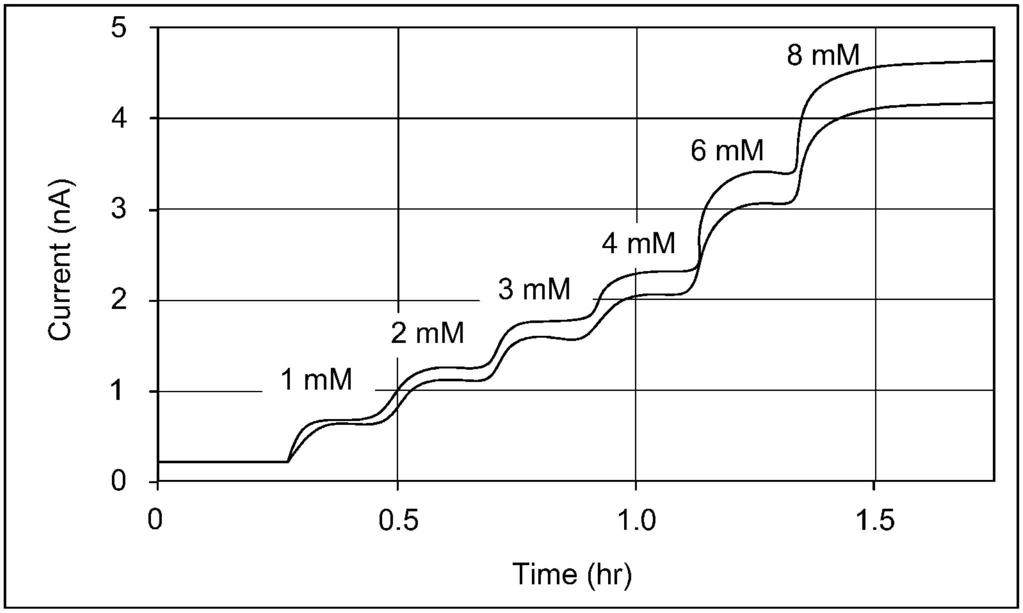
FIG. 27 shows four replicates of the response for an electrode containing diaphorase, $NAD^+$, and β-hydroxybutyrate dehydrogenase when exposed to varying β-hydroxybutyrate concentrations.
Figure 28:
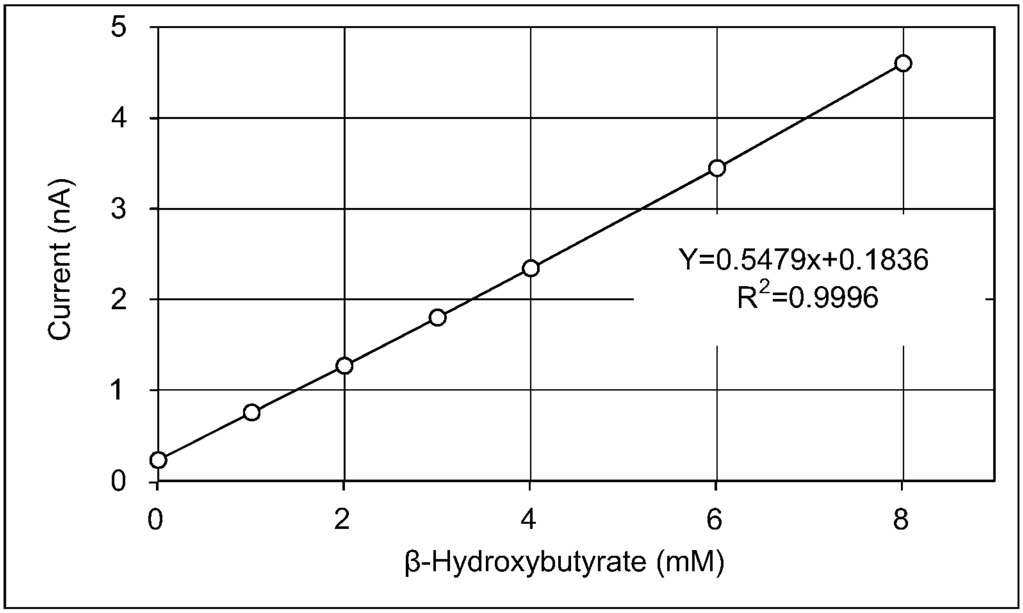
FIG. 28 shows an illustrative plot of average current response versus β-hydroxybutyrate concentration for the electrodes of FIG. 27.
Figure 29:
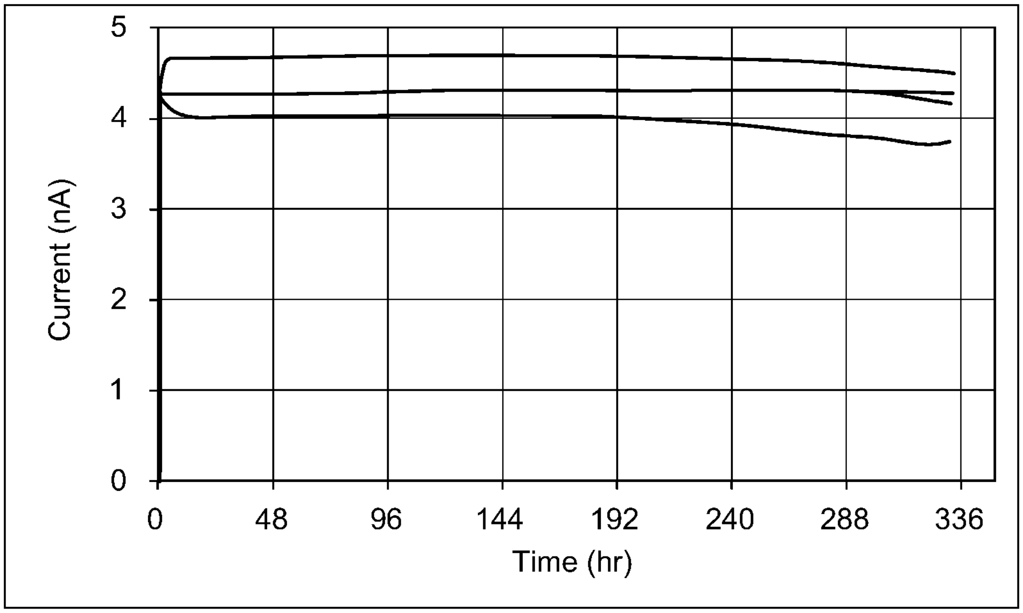
FIG. 29 shows an illustrative plot of current response for the electrodes of FIG. 27 when exposed to 8 mM of β-hydroxybutyrate in 100 mM PBS at 33° C. for 2 weeks.

Ketone analyses were conducted by immersing the electrode in 100 mM PBS buffer (pH=7.4) at 33° C. and introducing various amounts of β-hydroxybutyrate (0, 1, 2, 3, 4, 6 and 8 mM total β-hydroxybutyrate addition). FIG. 27 shows four replicates of the response for an electrode containing diaphorase, $NAD^+$, and β-hydroxybutyrate dehydrogenase when exposed to varying β-hydroxybutyrate concentrations. As shown, the current response increased over the course of several minutes following exposure to a new β-hydroxybutyrate concentration before stabilizing thereafter. FIG. 28 shows an illustrative plot of average current response versus β-hydroxybutyrate concentration for the electrodes of FIG. 27. The ketone sensors also exhibited a stable response over extended measurement times, as shown in FIG. 29. FIG. 29 shows an illustrative plot of current response for the electrodes of FIG. 27 when exposed to 8 mM of β-hydroxybutyrate in 100 mM PBS at 33° C. for 2 weeks. The mean signal loss over the measurement period was only 3.1%.

Example 6: Comparison of Lactate Sensor Response for Various Sensor Configurations. Two different lactate oxidase/polymer formulations for active area deposition and two different membrane polymer formulations for mass transport limiting membrane deposition were prepared to assay the performance of lactate-responsive sensors featuring various permutations of these formulations. Formulation details and the process used for preparing the analyte sensors are provided below. In general, the analyte sensors were prepared in a manner similar to that described above.

TABLE 8

Lactate Oxidase (LOX) in 10 mM HEPES Buffer at pH = 8 (Formulation A)

| Component | Concentration (mg/mL) |
|---|---|
| LOX | 24.6 |
| Formula 1 Polymer | 20.4 |
| PEGDGE400 | 7.5 |

TABLE 9

Lactate Oxidase (LOX) in 10 mM MES Buffer at pH = 5.5 (Formulation B)

| Component | Concentration (mg/mL) |
|---|---|
| LOX | 24.6 |
| Human Serum Albumin | 24.6 |
| Formula 1 Polymer | 9.2 |
| PEGDGE400 | 6.2 |

To deposit each active area, ~20 nL of each solution was deposited upon a carbon working electrode to form 6 discrete spots, each having an area of approximately 0.01 $mm^2$. Formulation A was dispensed 4 times and Formulation B was dispensed 6 times to form the spots. Following deposition, the working electrode was cured overnight at 25° C. Formulation A corresponds to that used for depositing the active area of glucose-responsive analyte sensors, except substituting lactate oxidase for glucose oxidase.

Formulations for Mass Transport Limiting Membrane Deposition: Membrane polymer formulations were prepared in aqueous solution formulations specified in Tables 10 and 11 below.

TABLE 10

Polyvinylpyridine-co-Styrene Formulation in 80:20 Ethanol:HEPES Buffer-Gly3 Crosslinked (Formulation C)

| Component | Concentration (mg/mL) |
|---|---|
| Polyvinylpyridine-co-styrene polymer | 111.7 |
| Gly3 crosslinker | 7.0 |
| polydimethylsiloxane | 0.3 |

TABLE 11

Polyvinylpyridine Formulation in 80:20 Ethanol:HEPES Buffer-PEGDGE400 Crosslinked (Formulation D)

| Component | Concentration (mg/mL) |
|---|---|
| Polyvinylpyridine | 94.6 |
| PEGDGE400 crosslinker | 5.1 |
| polydimethylsiloxane | 0.3 |

Dip coating was used to deposit a mass transport limiting membrane upon each active area prepared as above. Formulation C was deposited using 4 dips, and Formulation D was deposited using 4 dips. A wait time of about 10 minutes between dips was used. Following the completion of dip coating, the membranes were cured for 24 hours at 25° C., followed by 48 hours at 56° C. in desiccated vials. Spray coating, screen printing, or similar processes may be alternately used to deposit the mass transport limiting membrane. Formulation C corresponds to that used for depositing a mass transport limiting membrane within glucose-responsive analyte sensors.

Lactate-responsive analyte sensors were prepared using the deposition conditions specified above. All possible combinations of active area and mass transport limiting membrane were prepared, with 8 sensors being fabricated for each possible combination. After fabrication, each sensor was exposed to a 5 mM lactate solution in 100 mM phosphate buffered saline (PBS) at 37° C. for 190 hours, with the working potential being held at +40 mV relative to Ag/AgCl. The tested combinations of active areas and mass transport limiting membranes are specified in Table 12. Testing results are shown in FIG. 30.

TABLE 12

| Sensor Group | Active Area | Mass Transport Limiting Membrane | Result |
|---|---|---|---|
| 1 | Formulation A | Formulation C | Poor sensitivity |
| 2 | Formulation A | Formulation D | Poor sensitivity |
| 3 | Formulation B | Formulation C | Variable sensitivity, decreasing signal intensity over time |
| 4 | Formulation B | Formulation D | High sensitivity, stable signal intensity over time |

Figure 30:
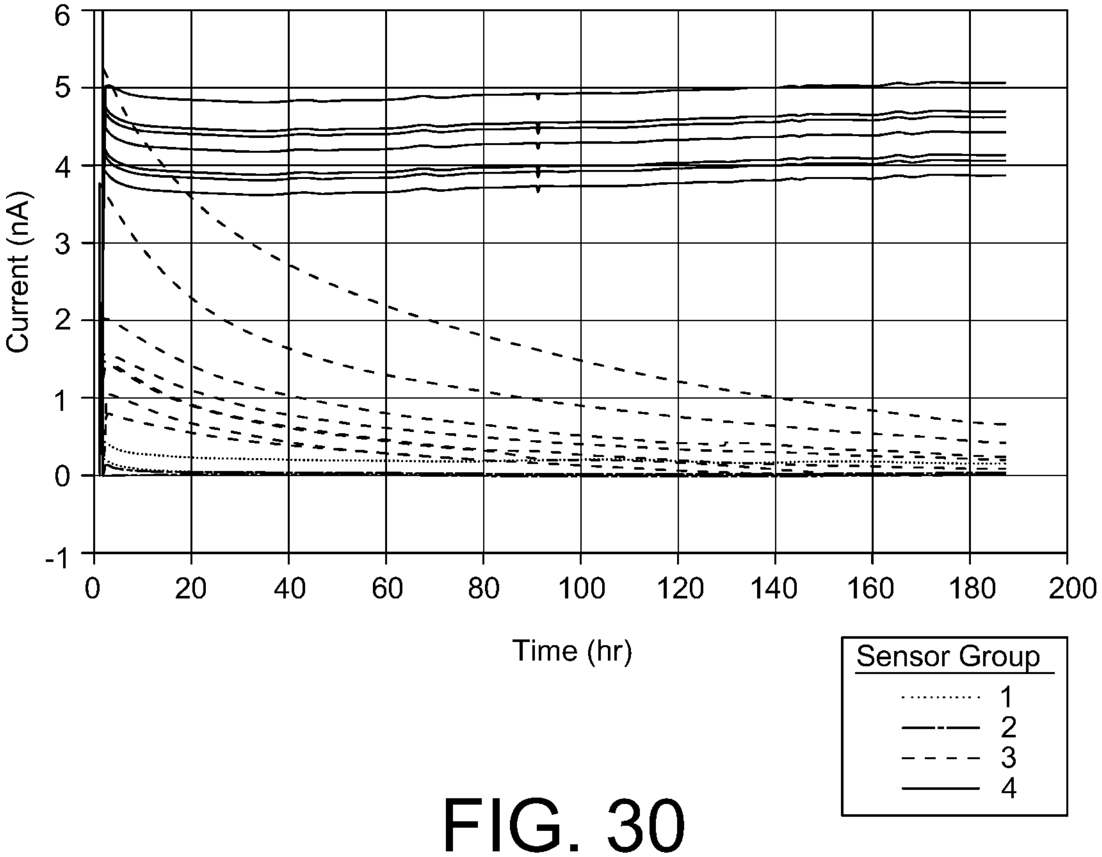
FIG. 30 shows an illustrative plot of sensor performance for Groups 1-4 in Example 6.

As shown in FIG. 30, lactate-responsive analyte sensors having active areas and mass transport limiting membranes formulated similarly to those used successfully in glucose-responsive analyte sensors (Group 1) afforded poor performance when exposed to lactate. As shown, the signal intensity was under 0.5 nA for all of the tested samples, which is undesirably low for a viable lactate-responsive sensor. The signal intensity was even poorer when polyvinylpyridine and a different crosslinking agent were substituted for the polyvinylpyridine-co-styrene and Gly3 crosslinker in Formulation C (Group 2).

Incorporation of human serum albumin considerably improved the sensor performance, as further shown in FIG. 30. Sample Group 3, for example, exhibited considerably higher signal intensities than were realized for any of the Group 1 or Group 2 samples. However, there was considerably variability in the initial signal intensity among this group of samples (>4 nA variance). Moreover, there was a steady decrease in the signal intensity from the initially observed maximum signal intensity. The response variability and the poor signal stability over time likewise makes the combination of this sample group unlikely to be suitable for a viable lactate-responsive analyte sensor.

Surprisingly, the combination of a human serum albumin-containing active area and a mass transport limiting membrane comprising crosslinked polyvinylpyridine homopolymer (Group 4) produced an acceptable combination of high signal intensity and extended signal stability over time. As shown in FIG. 30, all of the replicate sensors of Group 4 had initial signal intensities clustered within 1 nA of each other between 4 nA and 5 nA. This level of signal intensity and variability is within the range over which a commercially viable lactate-responsive analyte sensor might be developed. Moreover, the signal intensity only varied a few tenths of a nA or less over 190 hours of signal observation, which is again within a range that may be suitable for development of a commercially viable sensor.

Figure 31:
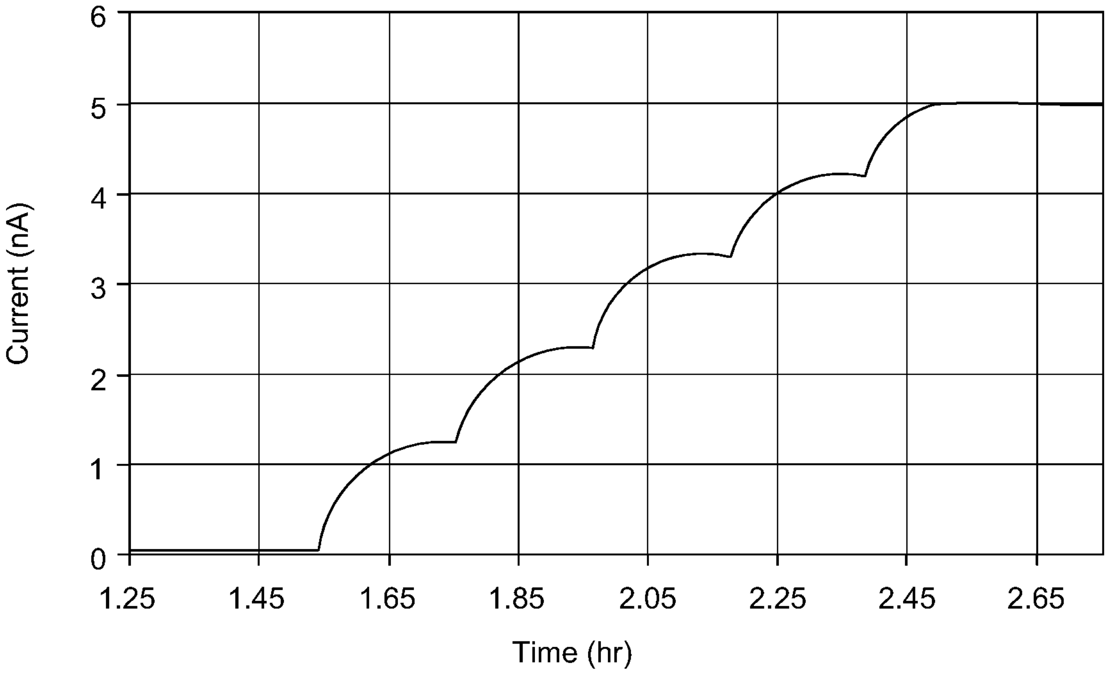
FIG. 31 shows an illustrative plot of the response of a Group 1 analyte sensor from Example 6 to lactate solutions having varying lactate concentrations.

As shown in FIG. 31, the observed current for the Group 4 sensors responded rapidly and achieved a stable value as increasing amounts of lactate were added in 1 mM increments to a PBS solution initially not containing lactate.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Analyte Sensor Ignition Lock

Vehicle fail safes, such as ignition locks, are sometimes used to prevent an operator from operating a vehicle when impaired or otherwise not in a condition to safely operate the vehicle. Operating the vehicle while impaired could potentially present significant dangers to the operator and the public. One common type of ignition lock is designed to prevent drunk driving and, more specifically, to prevent individuals from operating a vehicle while intoxicated through alcohol use. Such lock devices connect a breath-alcohol analyzer or optical sensor to the vehicle's ignition system, and the driver must successfully pass a blood alcohol level test before the vehicle can be started.

Intoxication is one type of impairment or condition that an operator may experience that renders the operator unfit or unable to operate a vehicle. However, other impairments and conditions can also afflict an operator and should also be monitored closely to ensure the operator does not operate a vehicle while impaired. For example, an operator with diabetes and driving while hypoglycemic (i.e., low blood sugar) could potentially undergo light-headedness, confusion, headache, loss of consciousness, seizures, and delayed reflexes, any of which could endanger his/her own life and those in the vehicle or in the vicinity of the vehicle.

Analyte monitoring systems, have been developed to facilitate long-term monitoring of analytes in bodily fluid (e.g., blood). Some analyte monitoring systems are designed to detect and monitor levels of blood glucose, which can be helpful in treating diabetic conditions. Other analyte monitoring systems, however, are designed to detect and monitor other analytes present in an operator's bodily fluid, and abnormal analyte levels detected in an operator may be indicative that the operator is currently unfit to safely operate a vehicle.

The following discussion describes an analyte monitoring and vehicle control system used to prevent operation of a vehicle when operator analyte levels cross a predetermined threshold. Having the sensor control device 102 (FIG. 1) properly deployed allows a user to intelligently track and monitor bodily fluid analyte levels and trends. When some analyte levels surpass certain thresholds, physical or cognitive impairment may ensue that renders a user unfit to safely operate a vehicle. In such instances, the user should take appropriate action to bring analyte levels back into safe ranges prior to attempting to operate a vehicle. In some cases, however, a user may feel perfectly fine to operate a vehicle but nonetheless have unsafe analyte levels that could suddenly trigger the onset of a dangerous physical impairment. In such cases, it may be advantageous to have a failsafe system in place that prevents or warns the user from operating a vehicle and potentially placing self and/or others in danger.

Figure 32:
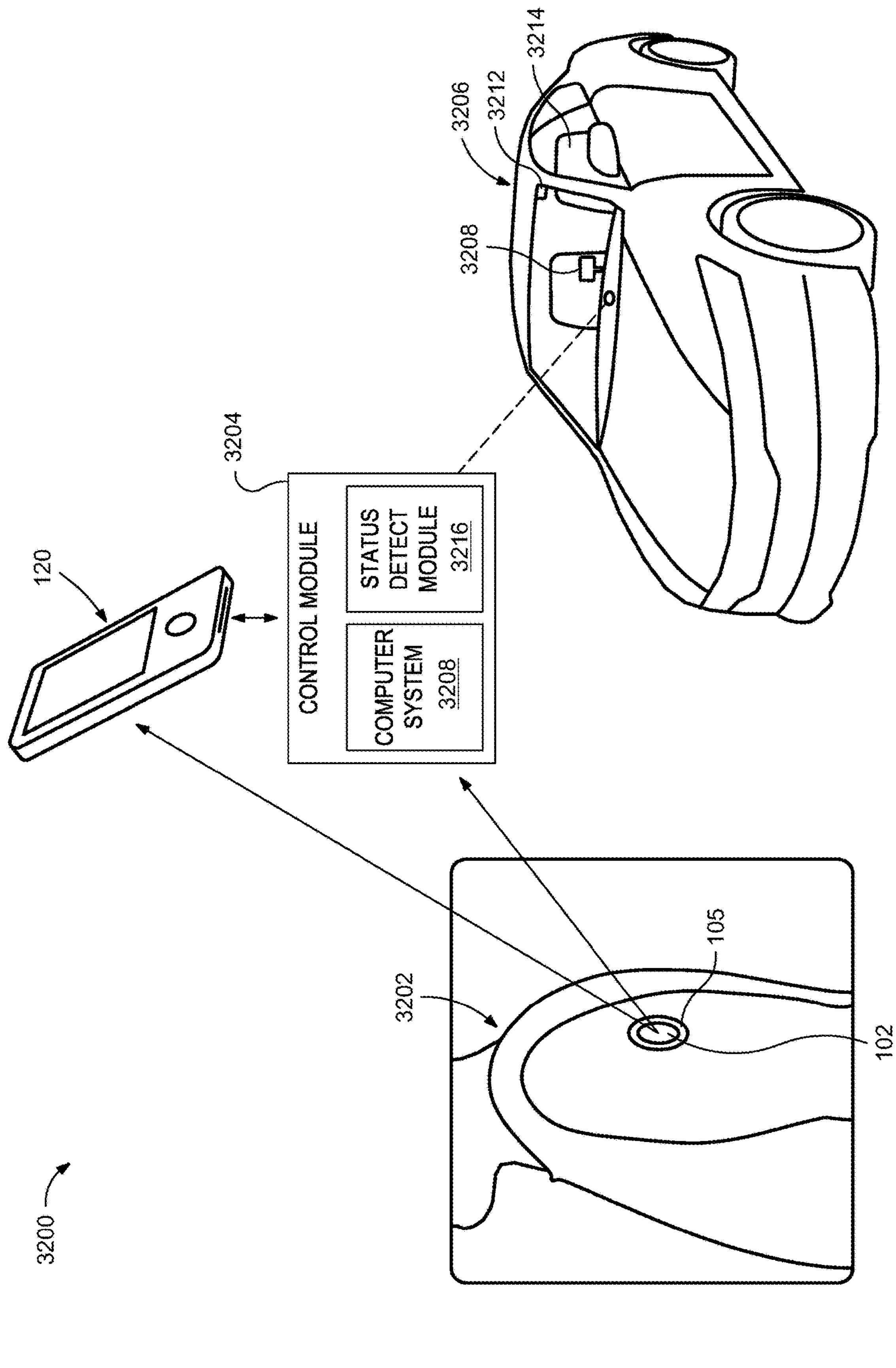
FIG. 32 is a schematic diagram of an example analyte monitoring and vehicle control system, according to one or more embodiments of the present disclosure.

FIG. 32 is a schematic diagram of an example analyte monitoring and vehicle control system 3200, according to one or more embodiments of the present disclosure. As illustrated, the analyte monitoring and vehicle control system 3200 (hereafter "the system 3200) includes the sensor control device 102, which may be deployed on a user or "operator" 3202 and otherwise delivered to a target monitoring location on the body of the operator 3202, such as the back of an arm. As discussed above, the sensor control device 102 includes the sensor 104 (FIG. 1), and when properly deployed, the sensor 104 is positioned transcutaneously within the skin to detect and monitor analytes present within a bodily fluid of the operator 3202. The adhesive patch 105 (FIG. 1) applied to the bottom of the sensor control device 102 adheres to the skin to secure the sensor control device 102 in place during operation.

While the system 3200 is described herein as including the on-body sensor control device 102 to detect and report analyte levels, the system 3200 may alternatively incorporate an ex vivo analyte sensor (e.g., a self-monitoring blood glucose "SMBG" meter), without departing from the scope of the disclosure. Accordingly, the term "sensor control device" should be interpreted herein to include not only on-body sensor systems, as generally described above, but also traditional, hand-held sensor systems.

As illustrated, the system 3200 may further include the reader device 120, and the sensor control device 102 may be in communication with the reader device 120 via a local communication path or link to provide analyte concentration data automatically, periodically, or as desired by the operator 3202. The reader device 120 may be in communication with a control module 3204, which is in communication with the electrical system of a vehicle 3206 and powered by the vehicle battery or otherwise powered by a separate battery. In such embodiments, data transmitted to the reader device 120 from the sensor control device 102 may be subsequently transmitted by the reader device 120 to the control module 3204 for processing. In other embodiments, however, the sensor control device 102 may communicate directly with the control module 3204 via any wireless communication protocol, such as BLUETOOTH®. In such embodiments, the reader device 120 may or may not be necessary in the system 3200.

In the illustrated embodiment, the vehicle 3206 is depicted as an automobile. As used herein, however, the term "vehicle" is used broadly and is meant to include any kind of transportation vehicle that can be operated by a human user or "operator," but can also include autonomous vehicles used to transport humans. Examples of the vehicle 3206 include, but are not limited to, any type of automobile, truck, sport utility vehicle, aircraft, watercraft, spacecraft, and or any other means of transportation, or combinations thereof.

The control module 3204 may include a communications interface to communicate information to/from the sensor control device 102 and/or the reader device 120. In the case of an exemplary BLUETOOTH®-enabled sensor control device 102 and/or reader device 120, a pairing mode may be entered into when the sensor control device 102 approaches the vehicle 3206. Upon pairing, the control module 3204 may be programmed and configured to automatically detect the presence of and establish communication with the sensor control device 102 and/or the reader device 120. For example, when the operator 3202 approaches or enters the vehicle 3206, the control module 3204 may automatically detect the presence of the sensor control device 102 and enable communication therebetween or with the reader device 120.

In some embodiments, the control module 3204 may be in communication with a vehicle user interface 3208 included in the vehicle 3206, such as an infotainment system, a touchscreen display, or an information display. In such embodiments, the control module 3204 may visually communicate with the operator 3202 via the vehicle user interface 3208 and may also be able to audibly communicate with the operator 3202 via the audio speakers included in the vehicle 3206. In other embodiments, however, the control module 3204 may be configured to communicate with the reader device 120 to be able to communicate with the operator 3202.

As illustrated, the control module 3204 may be or otherwise include a computer system 3210 configured and otherwise programmed to control various operations and/or systems of the vehicle 3206 based on real-time measured analyte levels of the operator 3202 as obtained by the sensor control device 102. Operation of the vehicle 3206 is controlled, disabled, or modified by either disabling one or more critical systems of the vehicle 3206 or by activating warning systems in the vehicle 3206. When the real-time measured analyte levels of the operator 3202 are within a predetermined safe range, then it may be considered safe for the operator 3202 to operate the vehicle 3206. When the real-time measured analyte levels of the operator 3202 fall outside the predetermined safe range or cross a predetermined threshold, however, the computer system 3210 may then be programmed to control, disable, or modify operation of the vehicle 3206.

In some embodiments, for example, the computer system 3210 may be configured to disable various critical vehicle systems when detected analyte levels of the operator 3202 fall outside of a predetermined range or otherwise cross a predetermined threshold, thus progressively and safely disabling operation of the vehicle when identifying the operator 3202 as impaired for safe operation of the vehicle 3206. Critical vehicle systems of the vehicle 3206 that may be disabled include the ignition system (e.g., energy switching/control system), the transmission system (or gear box), the fuel system, energy supply system (e.g., a battery, capacitor, conversion/reaction cell, etc.). When elevated or lowered (unsafe) analyte levels are detected, the computer system 3210 may prevent the critical vehicle systems from functioning or operating. Consequently, the operator 3202 will be unable to start or operate the vehicle 3206, thereby preventing the operator 3202 from placing themselves and/or others in danger.

In other embodiments, or in addition thereto, the computer system 3210 may be configured to activate various non-critical vehicle systems when detected analyte levels of the operator 3202 surpass or cross a predetermined threshold. Non-critical vehicle systems that may be activated include, for example, the vehicle horn, the vehicle lights, or an audible warning system installed in the vehicle 3206. In such embodiments, activation of the non-critical vehicle systems may alert law enforcement and others (e.g., operators of adjacent vehicles, bystanders, pedestrians, etc.) of an operator 3202 that may be driving in an impaired condition, thus allowing law enforcement to quickly address any issues related thereto and placing others on notice of a potentially dangerous situation.

In yet other embodiments, or in addition thereto, the computer system 3210 may be configured to automatically place a phone call to one or more emergency contacts when analyte levels of the operator 3202 fall outside of a predetermined safe operating range or otherwise cross a predetermined threshold. In such embodiments, the computer system 3210 may operate through the reader device 120 (e.g., a cellular phone) or a cellular or satellite communication system incorporated into the vehicle 3206 (e.g., OnStar®). In other embodiments, or in addition thereto, the computer system 3210 may be configured to automatically send a message (e.g., text or SMS message, email, etc.) to an emergency contact when analyte levels of the operator 3202 fall outside of a predetermined safe operating range or otherwise cross a predetermined threshold. Example emergency contacts include, but are not limited to, a spouse, a parent, medical personnel (e.g., a doctor), a hospital, 911, or any combination thereof.

In some embodiments, the system 3200 may further include one or more proximity sensors 3212 configured to detect the presence of the operator 3202 and, more particularly, the sensor control device 102. In such embodiments, the proximity sensor(s) 3212 may be configured to monitor the general area of the driver's seat 3214 within the vehicle 3206. If the sensor control device 102 is detected within the area of the driver's seat 3214 by the proximity sensor(s) 3212, that may provide a positive indication that the operator 3202 is in the driver's seat 3214 and potentially attempting to operate the vehicle 3206. In such cases, a signal may be sent to the control module 3204 alerting the computer system 3210 that the operator 3202 is in the vehicle 3206 and potentially attempting to operate the vehicle 3206. If the real-time measured analyte levels of the operator 3202 are within a predetermined safe range or below a predetermined level, then the computer system 3210 may allow the operator 3202 to operate the vehicle 3206. When the real-time measured analyte levels of the operator 3202 fall outside the predetermined safe range or cross a predetermined threshold, however, the computer system 3210 may control, disable, or modify operation of the vehicle 3206, as generally described above. As will be appreciated, the proximity sensor(s) 3212 may be advantageous in preventing operation of the vehicle 3206 only when the impaired operator 3202 is in the driver's seat 3214 and ready to operate the vehicle 3206. Consequently, a user wearing the sensor control device 102 is able to ride as a passenger in the vehicle 3206 in any state without affecting operation of the control module 3204 or the vehicle 3206.

In some embodiments, the control module 3204 may further include a vehicle status detection module 3216 configured to detect the current status of the vehicle 3206, including whether the vehicle 3206 is currently moving or is stationary. In addition, the vehicle status detection module 3216 may be configured to determine whether or not the motor in the vehicle 3206 is currently operating or is stopped. In one or more embodiments, the vehicle status detection module 3216 may provide a status signal to the control module 3204, and the control module 3204 can then use the status signal to determine what vehicle operations should be activated or disabled when the real-time measured analyte levels of the operator 3202 fall outside the predetermined safe range or cross a predetermined threshold. For example, when the status signal indicates that the vehicle 3206 is stationary, the control module 3204 can disable the vehicle fuel system, transmission system, ignition system, or any combination thereof. In contrast, when the status signal indicates that the vehicle 3206 is moving, the control module 3204 can activate the vehicle horn, flash the vehicle lights, or activate an audible warning to the operator 3202 and/or those around the operator 3202 that the operator 3202 is impaired.

In some embodiments, once the operator 3202 enters the vehicle 3206 or when the control module 3204 pairs with the sensor control device 102 and/or the reader device 120, an app may be launched on the reader device 120 or the vehicle user interface 3208, and a digital dashboard may appear on the reader device 120 and/or the vehicle user interface 3208 that depicts current analyte levels, trend, historical data, and projected analyte levels. If the current analyte levels fall outside of a predetermined safe operating range, however, the computer system 3210 may be programmed to disable one or more critical vehicle systems to prevent the operator 3202 from operating the vehicle 3206. In such embodiments, a visual or audible alert may be issued by the control module 3204 to inform the operator 3202 as to why the vehicle 3206 is not starting. More particularly, a visual alert (e.g., a written message) may be generated and displayed on the reader device 120 or the vehicle user interface 3208, or an audible alert (e.g., a vocal message) may be transmitted through the speakers in the reader device 120 or the vehicle 3206.

If not done automatically, the operator 3202 may be prompted to obtain a current analyte level upon pairing the sensor control device 102 with the control module 3204. In some cases, the vehicle 3206 may be prevented from being operated until a current analyte level is obtained. If the current analyte levels are within safe limits, the computer system 3210 may allow operation of the vehicle 3206. In some aspects, and unless done automatically, the control module 3204 may prompt the operator 3202 to obtain additional current analyte levels after operating the vehicle 3206 for a predetermined period of time (e.g., after 1 hour, 2 hours, 5 hours, etc.).

In some embodiments, the control module 3204 may be configured to issue visual or audible recommendations or coaching to the operator 3202 that may help bring measured analyte levels back into safe ranges. In such embodiments, such visual or audible recommendations may prompt the user to take some action that could result in bringing analyte levels back into safe ranges. Moreover, in some embodiments, the operator 3202 may be able to communicate with the control module 3204 verbally by issuing verbal responses or commands. This may prove advantageous in helping prevent distracted operation of the vehicle 3206.

In some embodiments, settings of the control module 3204 may be customized by the operator 3202 to allow the user to make informed decisions once unsafe analyte levels have been detected and a visual or audible alert has been issued by the control module 3204. More specifically, in at least one embodiment, the control module 3204 may include a bypass feature that the operator 3202 might enable to allow the operator 3202 to operate the vehicle 3206 even when unsafe analyte levels have been measured. In such embodiments, the operator 3202 may operate the vehicle 3206 by acknowledging that the operator 3202 might be operating the vehicle 3206 in an impaired or unsafe health state.

In some embodiments, the computer system 3210 may be configured or otherwise programmed to calculate a predicted timeline when analyte levels of the operator 3202 may depart from a predetermined safe range or otherwise cross a predetermined threshold. In such embodiments, the control module 3204 may be configured to issue visual or audible alerts to the operator 3202 indicating approximately how much time the operator 3202 has before unsafe analyte levels may be reached and a potential unsafe medical condition may ensue. Multiple alerts may be provided to indicate when the operator has specific time increments remaining before unsafe analyte levels are reached. For example, visual or audible alerts may be issued when unsafe analyte levels will be reached within an hour, within a half hour, within 10 minutes, within 5 minutes, within 1 minute, and any time increment therebetween. Furthermore, a visual or audible alert may be issued once the analyte levels of the operator reach an unsafe level or cross a predetermined threshold.

In some embodiments, if unsafe analyte levels are measured while the operator 3202 is operating the vehicle 3206, the control module 3204 may be configured to issue one or more alerts (visual or audible) warning the operator 3202 of the unsafe analyte levels. In some cases, the volume of the stereo in the vehicle 3206 may be automatically lowered to enable the operator 3202 to hear an audible alert. In such embodiments, the control module 3204 may be configured to suggest one or more corrective actions to the operator 3202. Example corrective actions include, but are not limited to, slowing and stopping the vehicle 3206, locating and driving to a nearby convenience store or pharmacy, and locating a nearby hospital or medical facility. If the vehicle 3206 is an autonomous vehicle, and the current analyte levels place the operator 3202 in potentially dangerous conditions, the control module 3204 may automatically direct the vehicle 3206 to a medical facility for treatment. Alternatively, or in addition thereto, the control module 3204 may progressively reduce or restrict the speed of the vehicle 3206 when unsafe analyte levels are detected, thus forcing the operator 3202 to come to a stop and remedy the issue before continuing to operate the vehicle 3206.

The system 3200 may be useful in several different scenarios to protect the operator 3202 and/or those around the operator 3202 while driving. In some applications, the system 3200 may be incorporated voluntarily by the operator to detect impairment in real-time. In other applications, the system 3200 may be required by the owner of the vehicle 3206 to detect impairment of the operator 3202. In such applications, the owner of the vehicle 3206 may be a transport or trucking company. In yet other applications, the system 3200 may be legally imposed on the operator 3202 to detect impairment.

Embodiments disclosed herein include:

K. An analyte monitoring and vehicle control system that includes a sensor control device having a sensor that detects and monitors one or more analytes present within a body of an operator, and a control module in communication with the sensor control device and an electrical system of a vehicle, the control module including a computer system programmed to receive and process data provided by the sensor control device, wherein operation of the vehicle is controlled or disabled by the computer system when a real-time measured analyte level of the operator crosses a predetermined safe threshold.

L. A method that includes detecting and monitoring one or more analytes present within a body of an operator with a sensor control device having a sensor, receiving and processes data provided by the sensor control device with a control module in communication with the sensor control device and an electrical system of a vehicle; and controlling or disabling operation of the vehicle with a computer system of the control module when a real-time measured analyte level of the operator crosses a predetermined safe threshold.

Each of embodiments K and L may have one or more of the following additional elements in any combination: Element 1: wherein the sensor control device is coupled to the operator and the sensor is transcutaneously positioned beneath skin of the operator to detect and monitor the analytes present within a bodily fluid of the operator. Element 2: wherein the sensor control device comprises an ex vivo analyte sensor. Element 3: further comprising a reader device that receives the data from the sensor control device and transmits the data to the control module. Element 4: wherein the vehicle comprises a transportation vehicle selected from the group consisting of an automobile, an autonomous vehicle, a truck, a sport utility vehicle, an aircraft, a watercraft, a spacecraft, or any combination thereof. Element 5: wherein sensor control device pairs with the control module for communication upon the operator approaching the vehicle. Element 6: further comprising a vehicle user interface included in the vehicle and in communication with the control module. Element 7: wherein operation of the vehicle is disabled by disabling one or more critical systems of the vehicle, the critical systems being selected from the group consisting of an ignition system, a transmission system, a fuel system, and an energy supply system. Element 8: wherein operation of the vehicle is controlled by at least one of activating one or more non-critical systems of the vehicle, calling or sending a message to one or more emergency contacts, and progressively reducing a speed of the vehicle. Element 9: further comprising one or more proximity sensors installed on the vehicle to monitor an area of a driver's seat of the vehicle and detect a presence of the operator. Element 10: wherein the control module further includes a vehicle status detection module that detects the current status of the vehicle. Element 11: wherein the control module generates visual or audible alerts perceivable by the operator when the real-time measured analyte level of the operator falls outside of the predetermined safe threshold. Element 12: wherein the visual or audible alerts are generated at specific time increments before unsafe analyte levels are reached. Element 13: wherein the visual or audible alerts comprise one or more suggested corrective actions communicated to the operator. Element 14: wherein the control module includes a bypass feature allowing the operator to operate the vehicle when the real-time measured analyte level of the operator crosses the predetermined threshold.

Element 15: further comprising receiving the data from the sensor control device and transmitting the data to the control module with a reader device in communication with the sensor control device and the control module. Element 16: wherein disabling operation of the vehicle comprises disabling one or more critical systems of the vehicle, the critical systems being selected from the group consisting of an ignition system, a transmission system, a fuel system, and an energy supply system. Element 17: wherein controlling operation of the vehicle comprises at least one of activating one or more non-critical systems of the vehicle, calling or sending a message to one or more emergency contacts, and progressively reducing a speed of the vehicle. Element 18: further comprising monitoring an area of a driver's seat of the vehicle and detecting a presence of the operator with one or more proximity sensors installed on the vehicle. Element 19: further comprising detecting the current status of the vehicle with a vehicle status detection module included in the control module. Element 20: further comprising generating visual or audible alerts perceivable by the operator with the control module when the real-time measured analyte level of the operator crosses the predetermined threshold.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is:

1. A sensor control device for detecting glucose and ketones in vivo, the sensor control device comprising:

(a) a sensor comprising:

a substrate with a first face and a second face;

a reference electrode;

a first working electrode, wherein a ketones-responsive active area is disposed upon a surface of the first working electrode;

a second working electrode, wherein a glucose-responsive active area is disposed upon a surface of the second working electrode, wherein the electrodes are electrically isolated from one another by a dielectric material; and a mass transport limiting membrane overcoating the ketones-responsive active area and the glucose-responsive active area, the mass transport limiting membrane providing variable analyte permeability at each of the ketones-responsive active area and the glucose-responsive active area;

wherein the mass transport limiting membrane overcoating at least the ketones-responsive active area comprises a multi-component membrane; and wherein the sensor is configured to be partially inserted into a user's skin such that a distal portion of the sensor is in contact with an interstitial fluid to detect glucose and ketones in vivo; and (b) sensor electronics.

2. The sensor control device of claim 1, wherein the first and second working electrodes are independently disposed on the first and second faces of the substrate.

3. The sensor control device of claim 1, wherein the first working electrode and the second working electrode are located on opposite faces of the substrate, and wherein the ketones-responsive active area and the glucose-responsive active area are laterally spaced apart.

4. The sensor control device of claim 1, wherein the first working electrode and the second working electrode are each located on the first face or the second face of the substrate, and wherein the ketones-responsive active area and the glucose-responsive active area are vertically spaced apart.

5. The sensor control device of claim 3, further comprising a counter electrode.

6. The sensor control device of claim 5, wherein the reference electrode and the counter electrode are located on opposite faces of the substrate.

7. The sensor control device of claim 4, further comprising a counter electrode.

8. The sensor control device of claim 7, wherein the reference electrode and the counter electrode are each located on the first or second face of the substrate.

9. The sensor control device of claim 1, wherein the ketones-responsive active area comprises a first polymer and an enzyme system comprising nicotinamide adenine dinucleotide (NAD) and at least two enzymes that facilitate detection of ketones.

10. The sensor control device of claim 9, wherein the glucose-responsive active area comprises a second polymer and a glucose-responsive enzyme.

11. The sensor control device of claim 1, wherein the multi-component membrane disposed upon the ketone-responsive active area comprises two or more different membrane polymers.

12. The sensor control device of claim 11, wherein the multi-component membrane disposed upon the ketone-responsive active area comprises at least a bilayer membrane.

13. The sensor control device of claim 11, wherein the mass transport limiting membrane has a thickness over the ketones-responsive active area that differs from a thickness of the mass transport limiting membrane over the glucose-responsive active area.

14. The sensor control device of claim 11, wherein the mass transport limiting membrane has a composition over the ketones-responsive active area that differs from a composition of the mass transport limiting membrane over the glucose-responsive active area.

15. The sensor control device of claim 14, wherein:

the mass transport limiting membrane comprises a first portion overcoating the ketones-responsive active area and a second portion overcoating the glucose-responsive active area; wherein the first portion comprises a first membrane polymer and a second membrane polymer that differ from each other; and wherein the second portion comprises the first membrane polymer or the second membrane polymer.

16. The sensor control device of claim 15, wherein the first membrane polymer comprises a crosslinked polyvinylpyridine homopolymer or copolymer.

17. The sensor control device of claim 16, wherein the second membrane polymer comprises a crosslinked polyvinylpyridine-co-styrene polymer.

18. The sensor control device of claim 14, wherein the ketones-responsive and glucose-responsive active areas each comprises at least one sensing spot, and the ketones-responsive and glucose-responsive active areas each range in size from about 0.01 $mm^2$ to about 1 $mm^2$.

19. The sensor control device of claim 9, wherein the enzyme system comprises β-hydroxybutyrate dehydrogenase and diaphorase.

20. The sensor control device of claim 10, wherein the glucose-responsive enzyme comprises glucose oxidase.

21. The sensor control device of claim 9, wherein the ketones-responsive active area comprises a first electron transfer agent.

22. The sensor control device of claim 10, wherein the glucose-responsive active area comprises a second electron transfer agent.

23. The sensor control device of claim 1, wherein the first working electrode is configured to independently generate a first signal indicative of β-hydroxybutyrate concentration, and wherein the second working electrode is configured to independently generate a second signal indicative of glucose concentration.

24. The sensor control device of claim 23, wherein the first signal and second signal are measured simultaneously via a first channel and a second channel, respectively.

25. The sensor control device of claim 23, wherein the sensor electronics are configured to determine a ketone concentration and glucose concentration based on the first and second signals using a calibration curve for each analyte.

26. An analyte sensing system for detecting glucose and ketones in vivo comprising the sensor control device of claim 1.

27. The analyte sensing system of claim 26, further comprising a reader device.

* * * * *